United States Patent [19]
Wilfong et al.

[11] Patent Number: 5,643,375
[45] Date of Patent: Jul. 1, 1997

[54] METHOD FOR FORMING MULTILAYERED BARRIER STRUCTURES

[75] Inventors: Debra L. Wilfong, Lake Elmo; Richard J. Rolando, Oakdale, both of Minn.

[73] Assignee: Minnesota Mining and Manufacturing Company, St. Paul, Minn.

[21] Appl. No.: 366,817

[22] Filed: Dec. 30, 1994

Related U.S. Application Data

[60] Division of Ser. No. 141,211, Oct. 20, 1993, Pat. No. 5,407,713, which is a continuation-in-part of Ser. No. 967,975, Oct. 28, 1992, abandoned, which is a continuation-in-part of Ser. No. 810,001, Dec. 18, 1991, abandoned.

[51] Int. Cl.$^6$ .................................................. B29C 47/00
[52] U.S. Cl. ........................ 156/244.24; 156/244.11; 156/272.2; 264/211.12; 264/211.13
[58] Field of Search ................. 156/244.11, 244.24, 156/272.2; 264/211.12, 211.13

[56] References Cited

U.S. PATENT DOCUMENTS

| | | | |
|---|---|---|---|
| 3,524,795 | 8/1970 | Peterson | 161/165 |
| 4,003,874 | 1/1977 | Ide et al. | 260/42.18 |
| 4,064,296 | 12/1977 | Bornstein et al. | 428/35 |
| 4,217,161 | 8/1980 | Yamada et al. | 156/242 |
| 4,239,826 | 12/1980 | Knott, II et al. | 428/35 |
| 4,254,169 | 3/1981 | Schroeder | 428/35 |
| 4,376,799 | 3/1983 | Tusim | 428/213 |
| 4,401,536 | 8/1983 | Lundell et al. | 204/159.2 |
| 4,407,897 | 10/1983 | Farrell et al. | 428/516 |
| 4,511,610 | 4/1985 | Yazaki et al. | 428/35 |
| 4,561,920 | 12/1985 | Foster | 156/244.11 |
| 4,726,984 | 2/1988 | Shah | 428/216 |
| 4,786,561 | 11/1988 | Fong | 428/502 |
| 4,826,493 | 5/1989 | Martini et al. | 604/327 |
| 4,880,592 | 11/1989 | Martini et al. | 264/514 |
| 4,906,495 | 3/1990 | Martini et al. | 264/36.7 |
| 4,931,230 | 6/1990 | Krueger et al. | 264/6 |
| 4,950,549 | 8/1990 | Rolando et al. | 428/500 |
| 4,983,171 | 1/1991 | Schirmer | 604/332 |
| 5,009,648 | 4/1991 | Aronoff et al. | 604/332 |
| 5,407,713 | 4/1995 | Wilfong et al. | 428/34.1 |

FOREIGN PATENT DOCUMENTS

| | | |
|---|---|---|
| 0248545 | 12/1987 | European Pat. Off. . |
| 0297741 | 4/1989 | European Pat. Off. . |
| 0405793 | 6/1990 | European Pat. Off. . |
| 0433060 | 12/1990 | European Pat. Off. . |
| 0444340 | 4/1991 | European Pat. Off. . |
| 0431475A2 | 6/1991 | European Pat. Off. . |
| 62-74648 | 4/1987 | Japan . |
| 1393693 | 5/1975 | United Kingdom . |
| 2138431 | 4/1983 | United Kingdom . |
| 2246741 | 12/1992 | United Kingdom . |

OTHER PUBLICATIONS

Evalca Technical Bulletin No. 140, Evalca Co. of EVAL America, Lyle, IL.

(List continued on next page.)

*Primary Examiner*—Kathleen Choi
*Attorney, Agent, or Firm*—Gary L. Griswold; Walter N. Kirn; F. Andrew Ubel

[57] ABSTRACT

Multilayered barrier structures comprising a gas barrier layer of a non-chlorine containing organic polymer which is substantially impermeable to oxygen gas and a moisture barrier layer of a mesophase propylene-based material are provided. These structures are environmentally compatible and radiation resistant, and exhibit one or more additional properties, including gas barrier properties, moisture barrier properties, toughness, heat sealability, softness, and quietness during wrinkling. Also provided are methods of preparing and using such multilayered barrier structures, and articles, such as films, pouches, and tubings, formed from these structures, as well as multilayer barrier structures with additional graft layers affixed thereto through the application of a dose of ionizing radiation.

20 Claims, 18 Drawing Sheets

OTHER PUBLICATIONS

"On the Existence of Near-range Order in Isotactic Polypropylenes", Robert L. Miller, *Polymer One*, 135 (1960).

G. Natta et al., "Structure and Properties of Isotactic Polypropylene", *Del Nuovo Cimento*, Suppl. A1, vol. XV, Serie X, No. 1, pp. 40–51 (1960).

Report No. 4364, "Manufacture of Superfine Organic Fibers", V. A. Wente et al., Naval Research Labs, published May 25, 1954.

Mathews, *Polymer Mixing Technology*, Chap. 3, Applied Science Publishers, Essex, England, 1982.

V. A. Wente et al., "Superfine Thermoplastic Fibers", 48, *Industrial Engineering Chemistry*, 1342 (1956).

METHOD FOR FORMING MULTILAYERED BARRIER STRUCTURES

CROSS-REFERENCE TO RELATED APPLICATION

This application is a divisional application of U.S. application Ser. No. 08/141,211, filed Oct. 20, 1993 now issued U.S. Pat. No. 5,407,713 which is a continuation-in-part of U.S. application Ser. No. 07/967,975 filed Oct. 28, 1992, now abandoned, which was a continuation-in-part of U.S. application Ser. No. 07/810,001 filed Dec. 18, 1991, now abandoned.

FIELD OF THE INVENTION

This invention relates to multilayered barrier structures exhibiting one or more properties, including gas barrier properties, moisture barrier properties, radiation resistance, toughness, heat sealability, quietness during wrinkling, and environmental compatibility. The invention also relates to methods of preparing and using such multilayered barrier structures, as well as to articles formed from such structures, and to multilayered barrier structures with additional graft layers affixed thereto.

BACKGROUND OF THE INVENTION

Multilayered structures which are both substantially impervious to gases and/or moisture are well known in the medical and food packaging industries. However, current structures suffer from a variety of problems, including environmental incompatibility, rapid deterioration after exposure to sterilizing radiation, lack of toughness, ineffective heat sealability, and an embarrassing tendency for personal care articles manufactured from these structures, such as ostomy pouches, to make noise due to wrinkling during use.

Currently, poly(vinylidene chloride) (PVDC) is used as one of the materials of choice for the gas barrier component of barrier films. For ostomy applications, a film of PVDC sandwiched between opposing layers of low density polyethylene (LDPE) is widely used, with PVDC functioning as the gas barrier, and LDPE as the moisture barrier. Also, polyvinyl chloride (PVC) can be used in the moisture barrier layer, or other layers, of such a structure. However, disposal of these chlorine-containing materials presents a number of environmental concerns, especially relating to incineration of these materials after use in hospitals or otherwise.

Both PVDC and PVC are viewed as hazardous to the environment and to personal health. Incineration of PVDC/PVC results in release of hydrochloric acid (HCl), providing the major portion of HCl in incinerator flue gases. Also, PVDC/PVC is suspected of contributing to polychlorinated dibenzodioxin and furan toxins formed during incineration. Levels of these toxins are up to three times greater in medical infectious waste as compared to municipal waste streams. See e-g., Staff Report, "Proposed Dioxius Control Measure for Medical Waste Incinerators", State of Calif., Air Resources Board, Stationary Source Division, pp. 1–40 (May 25, 1990); Medical Waste Policy Committee, "Perspectives on Medical Waste", A Report of the Nelson A. Rockefeller Institute of Government, State University of New York (Jun., 1989). In addition to incineration concerns exposure to di-2-ethylhexylphthalate (DEHP), a common plasticizer utilized with PVDC and PVC, may present a number of health-related concerns, including reduced blood platelet efficacy, and potential links to liver cancer. See e.g., Allwood, M. C., "The release of phthalate ester plasticizer from intravenous administration sets into fat emulsion", 29 *International Journal of Pharmacology*, 233–6 (1986).

Examples of barrier structures incorporating such hazardous chlorine-containing materials can be found in various U.S. Patents, such as U.S. Pat. No. 3,524,795, which discloses a layered packaging material with a gas barrier layer comprised of various vinyl chlorine-containing polymers, and U.S. Pat. No. 4,786,561, which discloses a heat-shrinkable barrier film of an oriented polyolefin film coated on one side with a vinylidene chloride copolymer. In addition, numerous other patent documents, including U.S. Pat. Nos. 5,009,648, 4,983,171, 4,906,495, 4,880,592, 4,826,493; British Patent Application No. GB 2138431; and European Patent Application No. EP 0433060; all disclose multilayered films which utilize chlorine-containing polymers for the construction of ostomy pouches and other personal care articles.

Crystalline polypropylene provides excellent protection from moisture and is often a material of choice for barrier structures, and for medical articles manufactured therefrom. In addition, crystalline polypropylene exhibits a number of other desirable properties, such as non-toxicity, chemical resistance and inertness to drugs and liquid media used with drugs, as well as its low cost and ease of processing by means of extrusion, molding, and the like. However, a disadvantage of crystalline polypropylene is its inherent inability to be heat sealed to other materials. Thus, medical articles, such as barrier structures, or packaging for medical articles, often cannot be effectively heat-sealed in the manufacture and/or assembly of the components of the article. Furthermore, similar problems may also occur in the packaging of pharmaceuticals or medical articles in an effort to protect them from undesired exposure to environmental contaminants, including pathogenic organisms.

Even after manufacture and assembly, such barrier structures and/or medical articles often require additional protection beyond secure heat sealing and package processing. Accordingly, such materials should be sterilized at the time of production, and thereafter maintained in a sterile condition during storage. While not all structures or articles require sterilization prior to usage, structural components which are resistant to radiation are more versatile for uses in medical articles and packaging than components unable to maintain structural integrity after irradiation. Thus, the most desirable material for a barrier structure, medical article, or the packaging formed therefrom, is one which possesses resistance to the structurally demanding forms of sterilization, such as by gamma or electron-beam radiation, even if current usages of the structure or articles do not require such sterilization.

A preferred method of sterilization uses gamma radiation, such as radioactive cobalt 60, since it can be performed on packages sealed by heat or other methods, insuring total and reliable sterility of the contents. In addition, electron beam radiation can also be utilized to sterilize barrier structures, medical articles, and/or their packaging materials. Furthermore, electron beam radiation can also be used to graft additional layers, such as adhesion promoting layers, onto polymer films and other articles. See e.g., U.S. Pat. No. 4,950,549.

Unfortunately, a further disadvantage of crystalline polypropylene is that gamma-irradiation or electron-beam irradiation causes degradation of its structural integrity (e.g., causing embrittlement, discoloration, and thermal sensitivity). Thus, barrier films incorporating crystalline polypropylene in moisture barrier layers, or other layers, and the articles or packaging materials formed therefrom, are incapable of maintaining their structural integrity for a useful period of time after exposure to ionizing radiation.

Examples of barrier structures and/or the articles formed from these structures which incorporate crystalline polypropylene are shown in numerous U.S. and foreign patents, including U.S. Pat. No. 4,217,161 and U.S. Pat. No. 4,511, 610, which disclose multilayered plastic vessels or containers, and processes for making such containers. The films comprising these vessels or containers include an inner gas barrier layer and outer moisture barrier layers of a crystalline polyolefin, preferably crystalline polypropylene or crystalline polypropylene/ethylene copolymers.

U.S. Pat. No. 4,239,826 and U.S. Pat. No. 4,254,169, both disclose multi-layer barrier films with a core gas barrier layer of a vinyl alcohol polymer or copolymer between opposing layers of a polyolefin blended with a chemically-modified polyolefin containing functional groups added thereto. Examples of chemically-modified polyolefins include vinyl acetate-vinyl alcohol copolymers, vinyl alcohol-ethylene vinyl acetate terpolymers, or high density polyethylene with an unsaturated fused-ring carboxylic acid grafted thereto. In addition, the films can contain additional outer layers overlying the modified polyolefin layers of polyolefin polymers or copolymers, such as high, medium and low density polyethylene, polypropylene, ethylene vinyl acetate copolymers, ethylene acrylic acid copolymers, nylons, or blends thereof.

Other exemplary patents include, Japanese Patent Application No. Sho 60[1085]-217190, published Apr. 6, 1987, which discloses a plastic laminate comprised of a polyvinyl alcohol gas barrier layer, with a plastic, olefin-containing, vapor barrier layer laminated thereto. Also, U.S. Pat. No. 4,064,296 discloses a heat shrinkable, multilayer film having a gas barrier layer and outer moisture barrier layers of oriented olefin polymers, which have been crosslinked through exposure to ionizing radiation. In addition, U.S. Pat. No. 4,407,897 discloses a multi-layer polymeric structure with a drying agent incorporated therein, and with outer moisture barrier layers of polymers such as polyethylene, polypropylene, or blends thereof.

Attempts have been made to overcome degradation problems associated with crystalline polypropylene. For example, mesomorphous polypropylene, as described in U.S. Pat. No. 4,931,230, and articles manufactured from mesomorphous polypropylene, such as described in U.S. Pat. No. 4,950,549, provide resistance to sterilizing irradiation. By controlling the method of preparing mesomorphous polypropylene, through the quenching of such polypropylene after hot-melt extrusion, the material or articles formed therefrom substantially maintain their structural integrity after exposure to ionizing taxation at dosages sufficient to degrade crystalline polypropylene.

Unfortunately, single-layer packaging films and the like made from crystalline polypropylene, or even mesomorphous polypropylene, are susceptible to tearing and puncturing which would disrupt the structural integrity of a manufactured component or packaging film after assembly. Thus, the usefulness of a sterilized medical article would be compromised by a puncture or tear in a polypropylene package. In addition, single-layer crystalline polypropylene cannot be effectively heat sealed against another material. Furthermore, even though mesomorphous polypropylene provides better heat, sealability than crystalline polypropylene, in certain instances it still cannot provide a sufficient heat seal to manufacture a multi-component medical article, or to provide an effective radiation-sterilized package.

In an effort to overcome these deficiencies, polymer blends of mesomorphous polypropylene and a polymer compatible with such polypropylene, as described in European Patent Application No. 0 405 793 (assigned to the same assignee as for this application) have been developed. These polymer blends exhibit enhanced physical properties, such as heat sealability and tear strength, while maintaining the radiation resistance associated with mesomorphous polypropylene.

Though mesomorphous polypropylene, or blends thereof, may be radiation resistant, the materials comprising the gas barrier layer of barrier films typically are not. For example, as described in Evalca Technical Bulletin No. 140 (available from Evalca Co., of EVAL America, located in Lyle, Ill.), typical gas barrier polymers, such as ethylene vinyl alcohol (EVOH) rapidly degrade after exposure to ionizing radiation. Furthermore, the polymeric adhesive layers often employed in such barrier films would also be expected to rapidly degrade after exposure to ionizing radiation.

To date, no barrier film exists which combines radiation resistance with environmental compatibility. Furthermore, there are no such barrier films which likewise exhibit one or more good packaging or component articleproperties, such as heat sealability, toughness, softness, and quietness.

SUMMARY OF THE INVENTION

There is a need for an environmentally compatible multilayer barrier film capable of maintaining its structural integrity for a useful period of time after exposure to ionizing radiation at a dosage sufficient to sterilize such a film, as well as for articles manufactured therefrom. Further, there is a need for such a film with one or more additional layers grafted thereto to modify the properties of the films, such as adhesion promotion. Preferably such films would also be tough, heat sealable, soft and/or quiet.

The present invention overcomes the deficiencies of previous barrier films and related articles by providing multi-layered barrier structures which are both environmentally compatible and resistant to sterilization via ionizing radiation, and which display barrier properties to gases such as $O_2$, $CO_2$, $H_2S$, and odors, as well as to moisture. In addition, these multilayered barrier films exhibit one or more other desirable properties, including superior toughness, heat sealability, quietness and softness, as well as enhanced or modified properties when additional layers are grafted thereto through the application of a dose of ionizing radiation.

In particular, the present invention provides a multilayered barrier structure having a gas barrier layer of a non-chlorine containing organic polymer which is substantially impermeable to oxygen gas, and a moisture barrier layer of a mesophase propylene-based material. Preferably, the gas barrier layer exhibits a permeability to oxygen gas of less than 100 $cc/m^2/d$-atm at 25° C. and 0% relative humidity. Since the multilayered barrier structures are chlorine-free, they can be disposed of via incineration without presenting a threat to the environment or personal safety.

The mesophase propylene-based materials of the moisture barrier layer can comprise mesomorphous polypropylene, mesopolymer blends, and/or mesocopolymers. In this regard, the present invention can provide multilayered barrier structures wherein the moisture barrier layer comprises mesomorphous polypropylene homopolymer, or a mesopolymer blend of mesomorphous polypropylene and at least one second polymer. Preferably, the second polymer is a compatible polymer which synergistically increases one or more of the physical properties, such as toughness, heat sealability, softness, and/or quietness, of the multilayered barrier structure.

In another aspect, the present invention also can provide multilayered barrier structures wherein the moisture barrier layer comprises a mesocopolymer. Like the mesomorphous polypropylene and mesopolymer blends of the present invention mesocopolymers can provide moisture barrier layer(s) of the multilayered barrier structure of the present invention that are tougher, softer, quieter, and/or more heat sealable than a corresponding copolymer with crystalline propylene therein.

The present invention also provides a method for preparing a multilayered barrier structure by coextruding a propylene-based material along with a non-chlorine containing organic polymer which is substantially impermeable to oxygen gas, to form a multilayered extrudate, and quenching the extrudate immediately after extruding to provide a multilayered barrier structure with a core layer of the non-chlorine containing organic polymer and at least one layer of a mesophase propylene-based material adjacent thereto.

In addition, the present invention provides a multilayered barrier structure for use as a barrier film. Specifically, a method of interposing a multilayered barrier film, including a gas barrier layer of a non-chlorine containing organic polymer, and at least one moisture barrier layer of a mesophase propylene-based material, between a protected environment and an external environment, such that gases and moisture cannot substantially pass therethrough, is provided.

Furthermore, the present invention also provides various articles formed from the multilayered barrier structures of the present invention, including, ostomy pouches, incontinence products, tapes, tubings, transdermal drug-delivery patches and packaging for medical and/or food products. Although the desired applications for these multilayered barrier structures are in a film form, the multilayered constructions could also be used for applications requiring rigid and semi-rigid structures, such as for medical containers, as well as for flexible structures, such as tubings and tapes.

In yet another aspect, the present invention provides a multilayered barrier structure having a gas barrier layer of a non-chlorine containing organic polymer which is substantially impermeable to oxygen gas, a moisture barrier layer of a mesophase propylene-based material, and a graft layer affixed to at least a portion of the multilayered structure by a dosage of ionizing radiation. Preferably, the graft layer enhances one or more properties of the multilayered structure, including surface adhesion, coefficient of friction, oxygen permeability, moisture permeability, or combinations thereof.

Also, the present invention also provides a method for preparing a multilayered barrier structure by coextruding a propylene-based material along with a non-chlorine containing organic polymer which is substantially impermeable to oxygen gas, to form a multilayered extrudate, quenching the extrudate immediately after extruding to provide a multilayered barrier structure with a core layer of the non-chlorine containing organic polymer and at least one layer of a mesophase propylene-based material proximate the core layer, and grafting a graft layer to at least a portion of the multilayered structure through exposure to a dosage of ionizing radiation.

Further, the present invention also provides radiation resistant articles formed from the multilayered barrier structures of the present invention having gas barrier layer of a non-chlorine containing organic polymer which is substantially impermeable to oxygen gas, at least one moisture barrier layer of a mesophase propylene-based material, and a graft layer affixed to at least a portion of the multilayered structure by a dosage of ionizing radiation.

For an additional appreciation of the scope of the present invention, a more detailed description of the invention follows, with reference to the drawings.

Definitions

For the purposes of this invention the definition of "polymer" includes a homopolymer, a copolymer, or an oligomer, as well as any mixtures or blends of one or more homopolymers, and/or one or more copolymers, and/or one or more oligomers.

The term "copolymer" refers to a polymeric material produced by the polymerization of two or more dissimilar monomers, either with or without another functional group, such as maleic anhydride, grafted thereto, as well as to a homopolymer with a functional group grafted thereto. Thus, the term "copolymer" includes, without limitation, random copolymers, block copolymers, sequential copolymers, and graft copolymers.

"Propylene-based material" refers to propylene monomer, or polypropylene polymer.

The term "moiety" refers to any substance which can be combined with a propylene-based material to form a copolymer, and includes, without limitation, a monomer, a polymer, or a molecule.

"Mesophase propylene-based material", refers to a propylene-based material, in the ordered, mesophase form, which is neither amorphous, nor so ordered as to constitute the isotactic I crystalline form (e.g., crystalline polypropylene) as described by G. Natta et al., "Structure and Properties of Isotactic Polypropylene", *Del Nuovo Cimento*, Suppl. A1, Vol. XV, Series X, No. 1, 1960, pp. 40–51, the disclosure of which is herein incorporated by reference. A mesophase propylene-based material is formed by quenching a propylene-based material from the melt state, as defined below, and includes, without limitation, mesomorphous polypropylene, mesopolymer blends, and/or mesocopolymers, as those terms are defined below.

"Quenching", refers to the process of immediately and rapidly cooling propylene-based material from the melt state such that mesophase propylene-based material is obtained.

As used herein, "a non-chlorine containing organic polymer which is substantially impermeable to oxygen gas" refers to polymeric materials which are essentially free from chlorine, and which have oxygen transmission rates of less than about 150 cc/m$^2$/day-atmosphere at 25° C. and 0% relative humidity.

"Olefin polymers" or "polyolefins", refers to polymers of the unsaturated hydrocarbons of the general formula $C_nH_{2n}$, including copolymers of olefins with other monomers such as ethylene with vinyl acetate.

"Mesomorphous polypropylene" (mPP) refers to the polypropylene homopolymer in the mesophase form.

The term "mesopolymer blend" refers to a mixture of mesomorphous polypropylene with at least one additional polymer (hereinafter a "second polymer").

The term "mesocopolymer" refers to a copolymer of a propylene-based material and a discernable amount of at least one moiety that is quenched from the melt state to form a copolymer in the mesophase form.

The "Rule of Mixtures" refers to a means for determining the hypothetical values for a given physical property of a blend of two or more polymers. The hypothetical value represents the summation of the proportional contribution of the actual values of the physical property from each of the constituent polymers, based on the weight percents of the constituent polymers incorporated into the blend. Under the "Rule of Mixtures", the value for a given physical property (property "X") of a blend of two polymers (polymers A & B) can be calculated according to the following formula: Hypothetical value of property "X" for a blend of polymers A & B=(Weight percent of polymer A in the blend)×(actual value of property "X" for polymer A)+(Weight percent of polymer B in the blend B)×(actual value of property "X" for polymer B).

A "compatible polymer" refers to any second polymer which when combined with mesomorphous polypropylene, forms a mesopolymer blend wherein at least one weight fraction of the mesopolymer blend has a more desirable physical property than would be expected under the Rule of Mixtures.

A "graft layer" refers to any additional layer affixed to at least a portion of the multilayered barrier structures of the present invention by grafting a compound or compounds to the surface of the barrier structures through the application of a dosage of ionizing radiation, preferably a dosage of electron beam radiation. For example, an graft layer of acrylic acid and/or dimethylacrylamide can be grafted to at least a portion of the surface of the multilayered barrier structures of the present invention through the exposure of such compound(s) and barrier structures to a dosage of electron beam radiation between about 5 kGy (0.5 Mrad) and about 200 kGy (20 Mrad). In such an instance, the grafted acrylic acid and/or dimethylacrylamide layer would form a surface adhesion layer that promotes the adhesion of other materials to the modified surface of the multilayered barrier structure.

A "tempering additive" refers to any polymer, which when combined into one or more layers of a mutilayered barrier structure according to the present invention, functions to modify the film properties, such as Young's modulus, fracture strain, and/or the frequency in Hertz (Hz) of sound emitted from a multilayered barrier structure when wrinkled, such that a soft, tough, and/or quiet multilayered barrier structure is obtained.

The "structural integrity" of a multilayered structure can be measured by the percent elongation to break of that structure. With respect to radiation resistance of such structures, percent elongation to break is used to measure the extent of degradation or embrittlement of these structures after irradiation. A substantially constant percent elongation at break over several months after irradiation is indicative of substantial maintenance of structural integrity of a multilayered structure over that period after irradiation.

BRIEF DESCRIPTION OF THE DRAWINGS

The invention may be further illustrated by reference to the accompanying Drawing wherein.

DETAILED DESCRIPTION OF EMBODIMENTS OF THE INVENTION

Multilayered Barrier Structures

Figure 1:
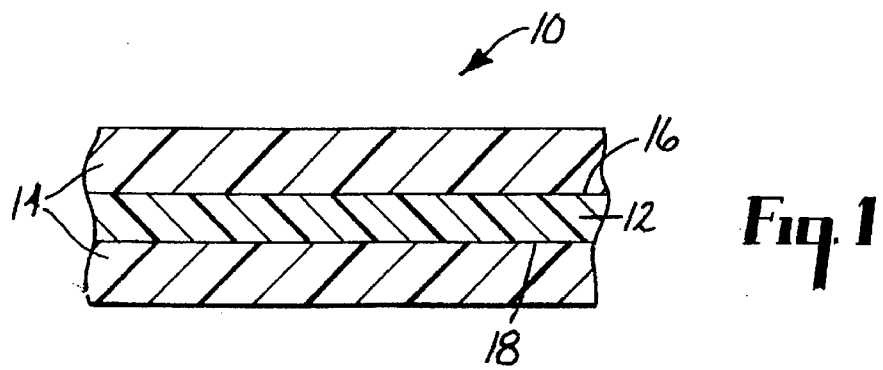
FIG. 1 is a cross-sectional illustration of a first embodiment of a multilayered barrier structure according to the present invention.
Figure 2:
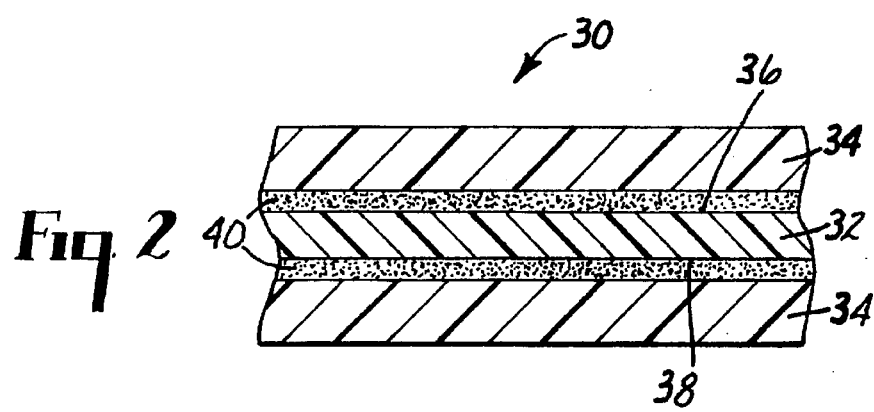
FIG. 2 is a Cross-sectional illustration of a second embodiment of a multilayered barrier structure according to the present invention.

FIGS. 1 and 2 show cross-sectional views of two embodiments of multilayered barrier structures 10,30 according to the present invention. FIG. 1 shows a first embodiment. The multilayered barrier structure 10 comprises a gas barrier layer 12, with a moisture barrier layer 14 contacting opposing sides 16,18 of the gas barrier layer 12. While it is preferable that the multilayered barrier structure 10 include moisture barrier layers 14 on each of the opposing sides 16,18 of the gas barrier layer 12, it will be appreciated that in certain applications, that the multilayered barrier structure 10 need only include a single moisture barrier layer 14 on one of the opposing sides 16,18 of the gas barrier layer 12.

FIG. 2 shows a second embodiment of a multilayered barrier structure 30 having a gas barrier layer 32 and opposing moisture barrier layers 34 proximate the opposing sides 36,38 of the gas barrier layer 32. In addition, this embodiment includes an optional adhesive layer 40 contacting the opposing sides 36,38 of the gas barrier layer 32, in between the gas barrier layer 32 and moisture barrier layers 34. Thus, the second embodiment contemplates a five layered barrier structure, comprising a central gas barrier layer 32, with adhesive layers 40 on each of the opposing sides 36,38 of the gas barrier layer 32, and a moisture barrier layer 34 contacted with each of the two adhesive layers 40. However, it will be appreciated that any multilayered barrier structure 10,30 with two or more layers, which includes at least one gas barrier layer 12,32, and at least one moisture barrier layer 14,34, is considered to fall within the scope of the present invention.

Throughout the remaining description of the embodiments of the invention, primary reference will be had to the embodiment illustrated in FIG. 1, unless otherwise indicated. However, it will be appreciated that this description also applies to the embodiment illustrated in FIG. 2.

Gas Barrier Layer

The gas barrier layer 12 of the multilayered structure 10 is comprised of a non-chlorine containing organic polymer which is substantially impermeable to oxygen gas. Preferably, the non-chlorine containing organic polymer exhibits a permeability to oxygen ($O_2$) gas of less than 100 $cc/m^2$/day-atmosphere (hereinafter expressed as "$cc/m^2$/di-atm"), more preferably less than 30 $cc/m^2$/d-atm, and most preferably less than 5 cc-25 $\mu/m^2$/d-atm, where the permeability measurements are taken at 25° C. and zero percent (0%) relative humidity. It will also be appreciated that the $O_2$ permeability measurements are expressed for a multilayered barrier structure with a gas barrier layer thickness of 25μ (microns). Accordingly, appropriate adjustment of the permeability values must be made, depending upon the thickness of the gas barrier employed in a structure, as well as the number of gas barrier layers utilized therein. In either case the values should be normalized to a total gas barrier layer thickness of 25 μ. All values were normalized to standard gas barrier layer thickness of 25μ by multiplying the oxygen transmission rate value by the ratio of barrier layer thickness to 25 μ. In addition to substantial impermeability to $O_2$ gas, it will further be appreciated that the gas barrier layer 12 also exhibits barrier properties to $CO_2$, $N_2$ and $H_2S$ gases, as well as to other gases and odors.

Non-limiting examples of non-chlorine containing organic polymers in accordance with the present invention include vinyl alcohol containing polymers, such as ethylene vinyl alcohol copolymer (EVOH) and polyvinyl alcohol (PVOH), polyacrylonitrile, polystyrene, polyester, and nylon, either alone, or blended with each other, or another polymer. Preferably, the non-chlorine containing organic polymer comprises a vinyl alcohol containing polymer such as EVOH or PVOH, with EVOH being particularly preferred. Also, the gas barrier layer 12 should preferably be comprised of substantially pure EVOH, most preferably comprising 99% or more EVOH. However, it also within the scope of the present invention to utilize blends of EVOH with other polymers, such as ethylene vinyl acetate copolymer.

Moisture Barrier Layer

The barrier properties of the gas barrier layer 12 of the multilayered barrier structure 10 are reduced in high moisture conditions. Accordingly, a moisture barrier layer 14 in accordance with the principles of the present invention is contacted with at least one side 16,18 of the gas barrier layer 12 to provide moisture protection for the gas barrier layer 12.

The moisture barrier layer 14 is comprised of a mesophase propylene-based material, such as mesomorphous polypropylene, mesopolymer blends, and/or mesocopolymers. Incorporation of the moisture barrier layer 14 comprised of mesomorphous polypropylene homopolymer, mesopolymer blends containing mesomorphous polypropylene, and/or mesocopolymers, into the multilayered barrier structure 10 according to the present invention unexpectedly enhances the overall properties of the multilayered barrier structure 10. In addition, by combining mesomorphous polypropylene with selected second polymers (i.e., compatible polymers) according to the present invention, mesopolymer blends may be obtained which exhibit enhanced properties over what would be expected of such blends under the Rule of Mixtures, as defined above. Furthermore, mesocopolymers used in the moisture barrier layer 14 also exhibit enhanced properties over that of copolymers incorporating the same moieties with propylene in a crystalline form. When these mesopolymer blends and/or mesocopolymers are incorporated into the multilayered barrier structure 10 via the moisture barrier layers 14, the overall properties of the multilayered barrier structure 10 is likewise enhanced.

For example, as described in European Patent Application No. 0 405 793, published Jan. 2, 1991, the disclosure of which is herein incorporated by reference, polymer blends of mesomorphous polypropylene and a "compatible" polymer exhibit increased resistance to the degrading effects of ionizing radiation, including gamma and electron-beam radiation, which are typically employed to sterilize packaging materials and medical articles. Furthermore, the mesopolymer blends may exhibit other desirable properties attributable to the compatible polymers, as that term is defined herein, such as increased toughness, heat sealability, softness, and quietness, depending upon the particular compatible polymer combined in the mesopolymer blend.

Surprisingly, utilization of mesomorphous polypropylene, mesocopolymers, and/or mesopolymer blends, such as those disclosed in European Patent Application No. 0 405 793, in the moisture barrier layer(s) 14 unexpectedly imparts increased radiation resistance to the overall multilayered barrier structure 10, including the gas barrier layer 12 and optional adhesive layers 40, and enhances other overall properties of the multilayered barrier structure 10 of the present invention, such as toughness, heat sealability, softness and/or quietness. See also, Applicants' copending and co-filed U.S. Patent Applications, Attorney Docket Nos. 47990U.S.A.2A U.S. Ser. No. 07/809,956, now abandoned) and 47990U.S.A.1B U.S. Ser. No. 07/967,837, now abandoned) (Rolando et al.) and 47991U.S.A.1A U.S. Ser. No. 07/809,959, now abandoned) and 47991U.S.A.8B U.S. Ser. No. 07/968,037, now abandoned) (Wilfong et al.). Also, the mesopolymer blends employed in the present invention need not be limited to combinations of mesomorphous polypropylene with compatible polymers, as that term is defined herein. Instead, any of one or more second polymers which can be combined with polypropylene, melt extruded, and quenched, such that the resulting mesopolymer blend includes mesomorphous polypropylene is considered to be within the scope of the present invention. However, it is preferable that the second polymer enhance the physical properties or characteristics of the mesopolymer blend when combined with mesomorphous polypropylene.

Non-limiting examples of second polymers include polybutylene (PB) polybutylene copolymers; atactic polypropylene resins available from Himont U.S.A. Inc., of Wilmington, Del.; polypropylene-ethylene copolymers; ethylene vinyl acetate copolymer (EVA); acid modified EVA; anhydride modified EVA; acid/anhydride modified EVA; ethylene acrylic acid copolymer (EAA); acid modified ethylene acrylate; anhydride modified ethylene acrylate; poly (4-methyl pentene); polyethylene, polyethylene copolymers, low density polyethylene (LDPE), linear low density polyethylene (LLDPE), high density polyethylene (HDPE); and acid/anhydride modified polypropylenes. Particularly preferred second polymers include polybutylene, EVA, and EAA. It will be appreciated that this list of second polymers is not exhaustive of second polymers which can be combined with mesomorphous polypropylene to form the mesopolymer blends utilized in certain embodiments of the moisture barrier layer(s) 14 of the multilayered barrier structure 10 of the present invention. See, e.g., Applicants' copending and co-filed U.S. patent application Ser. No. 07/809,959 (now abandoned) Attorney Docket No. 47991U.S.A.1A, assigned to the Assignee of the present invention, the disclosure of which is herein incorporated by reference.

As noted above, the moisture barrier layer(s) 14 may be formed solely of mesomorphous polypropylene. However, in other embodiments, a moisture barrier layer 14 comprised of a mesopolymer blend of mesomorphous polypropylene and one or more second polymer will be preferred. In such embodiments, the optimum weight fraction of the second polymer with the mesomorphous polypropylene depends upon the intended use and desired properties for the moisture barrier layer 14, and the final multilayered barrier structure 10 formed therefrom. Generally, when a mesopolymer blend is to be employed, it is desirable to add as much second polymer as possible to provide the needed strength, heat sealability, softness, quietness, and/or other desirable properties, without compromising the radiation resistance provided by the mesomorphous polypropylene of the mesopolymer blend.

However, when utilizing a mesopolymer blend, it is within the scope of this invention to add a discernibly minimal amount of the second polymer to the mesomorphous polypropylene to provide a mesopolymer blend, and resulting moisture barrier layer 14, quenched to preserve the mesomorphous polypropylene, having excellent resistance to sterilizing radiation, and better physical properties, such as heat sealability and toughness, than when the mesomorphous polypropylene homopolymer is utilized alone.

Optionally, as little as one percent (1%) by weight of the second polymer to the weight of the mesopolymer blend, quenched to preserve mesomorphous polypropylene, can form an acceptable mesopolymer blend utilized to form the moisture barrier layer(s) 14, and resulting multilayered structure 10, of the present invention. Such a mesopolymer blend can prove acceptable for certain medical applications requiring superior radiation resistance, and can also exhibit other desirable barrier and/or packaging properties.

It is also within the scope of the present invention to add a discernibly minimal amount of polypropylene to the second polymer to provide a mesopolymer blend, quenched to preserve mesomorphous polypropylene, wherein the moisture barrier layer 14, and resulting multilayered barrier structure 10, exhibits excellent barrier and/or packaging properties, and acceptable radiation resistance. Thus, when a mesopolymer blend is called for, optionally, as much as ninety-nine percent (99%) by weight of the second polymer to the weight of the mesopolymer blend, may form an acceptable mesopolymer blend according to the present invention.

It is desirable that the weight fraction range of the second polymer is from about five percent (5%) to about ninety-five percent (95%) by weight, and more desirably from about ten percent (10%) to about ninety percent (90%) by weight of the mesopolymer blend.

Preferably, when it is desirable to balance the best properties of the mesomorphous polypropylene and the second polymer in the mesopolymer blend, the weight fraction of the second polymer should range from about twenty percent (20%) to about eighty percent (80%) by weight, more preferably from about twenty-five percent (25%) to about seventy-five percent (75%) by weight of the mesopolymer blend, and most preferably from about forty percent (40%) to about sixty percent (60%) by weight of the mesopolymer blend.

Previously, it was unknown for copolymers of propylene-based materials with other moieties to form a mesophase form upon quenching. However, it has now been surprisingly discovered that these mesocopolymers provide many, if not all, of the same advantages as mesomorphous polypropylene and mesopolymer blends, such as increased resistance to ionizing radiation, toughness, softness, heat sealability and/or quietness. Accordingly, mesocopolymers can be used to form the moisture barrier layer(s) 14, and/or optional adhesive layer(s) 40, of the multilayered barrier structure 10 of the present invention.

Any moiety, or combination of moieties, can be used in conjunction with a propylene-based material to form the mesocopolymers according to the present invention. See, e.g., Applicants' copending and cofiled U.S. patent application, Attorney Docket Nos. 47990U.S.A.2A 07/809,956, now abandoned and 47990U.S.A.1B U.S. Ser. No. 07/967,837 now abandoned, assigned to the Assignee of the present invention, the disclosure of which is herein incorporated by reference. For example, the propylene-based material can comprise propylene monomer and the moiety of a different monomer other than propylene, such as ethylene or butylene, that when polymerized, melt extruded, and quenched, from a mesocopolymer within the scope of the present invention.

The mesocopolymers according to the present invention generally fall within three classes. The first class of copolymer comprises a mesocopolymer wherein the other moiety comprises a monomer, such as ethylene or butylene, that is inserted between propylene monomers in a copolymer chain. Accordingly, class one copolymers according to the present invention include, without limitation, random, sequential, and block copolymers. A commercially available example of such a copolymer, which when quenched forms a mesocopolymer according to the present invention, is Petrothane™ resin No. PP7300-KF (Quantum Chemical, Inc.).

The second class of copolymers according to the present invention, which when quenched can provide the mesocopolymers of the above described class one copolymers, with another moiety grafted to the copolymer chain. For example, the other moiety can comprise a functional group, such as maleic anhydride or acrylic acid, grafted to the copolymer chain, to provide enhanced melt flow rates, as well as other properties. See, e.g., U.S. Pat. No. 4,003,874, and British Patent No. 1,393,693, the disclosures of which are herein incorporated by reference. A commercially available example of such a copolymer is Plexar™ 420 (Quantum Chemical, Inc.).

The third, and final, general class of copolymers according to the present invention, which when quenched can provide the mesocopolymers, comprise a polypropylene homopolymer with a moiety, such as maleic anhydride or acrylic acid, grafted to the polymer chain. A commercially available example of such a copolymer is Admer™ QF551A (Mitsui Plastics, Inc.).

In a preferred embodiment, the mesocopolymer comprises a class one copolymer of propylene monomer with a discernable amount of at least one other monomer. Preferably, the propylene monomer will comprise from about 1% to about 99%, more preferably from about 50% to about 99%, and most preferably from about 91% to about 99% by weight of the mesocopolymer, with the remainder of the mesocopolymer comprising the other monomer, or monomers. The monomers to be combined with propylene to form the mesocopolymers according to the present invention can include any monomer that would polymerize with propylene in the presence of a suitable catalyst, including ethylene, butylene, pentene, methylpentene, and the like. Preferred monomers include ethylene and butylene, with ethylene being particularly preferred.

In a particularly preferred embodiment, the mesocopolymer according to the present invention comprises a copolymer of an ethylene monomer with a propylene monomer, that is quenched to provide the mesophase form of the copolymer. Preferably, the ethylene monomer comprises from about 1% to about 25%, more preferably from about 1% to about 20%, and most preferably from about 1% to about 10% by weight mesocopolymer, with the remaining monomer comprising propylene.

The mesocopolymer of the present invention can also be formed when the copolymer is blended in polypropylene homopolymer at from about one percent to about ninety nine percent by weight. A commercially available example of such a mixture is Shell resin FC05N, an ethylene-propylene copolymer mixed at a level of 14 percent by weight to 86 percent by weight of a polypropylene homopolymer. As with the copolymer alone, the blend of copolymer and homopolymer must be quenched immediately after extrusion to provide a mesocopolymer according to the present invention.

Optional Adhesive Layers

As noted above, the multilayered barrier structure 30 according to the present invention may also include optional adhesive layers 40, as illustrated in FIG. 2, interposed between the moisture barrier layer(s) 34 and the gas barrier layer 32. The adhesive layers 40 serve to adhere the gas barrier layer 32 and moisture barrier layers 34 together, when the selected materials comprising those layers are not naturally compatible, and therefore, not able to adhere to one another after coextrusion. For example, when the gas barrier layer 32 is comprised of EVOH copolymer, and the moisture barrier layers 34 are comprised of a mesopolymer blend of mesomorphous polypropylene and polybutylene, adhesive layers 40 are required to adhere the layers into a unitary, multilayered barrier structure 30 according to the present invention.

When an adhesive layer 40 is employed, the adhesive layer 40 should be comprised of materials which provide structural integrity to the multilayered barrier structure 30 of the present invention, without substantially affecting the barrier properties of the gas barrier layer 32 and moisture barrier layers 34. In this regard, it will be preferred to use a mesocopolymer in the adhesive layer 40, since adhesive mesocopolymers exhibit the same advantageous properties as the mesomorphous polypropylene, mesopolymer blends, and/or mesocopolymers comprising the moisture barrier layer 34 of the multilayered barrier structure 30 of the present invention.

It will be appreciated that adhesion between the gas barrier layer 12 and moisture barrier layer(s) 14 can always be achieved by utilizing a blend of polymer in either, or both, of these layers, wherein at least one of the polymers employed is a constituent polymer of both the gas barrier 12 and moisture barrier 14 layers. For example, in a structure such as illustrated in FIG. 1, by using mesomorphous polypropylene (mPP) in the moisture barrier layer(s) 14 and a blend of EVOH and mPP in the gas barrier layer 12, the mPP appearing in both layers will result in a natural adhesion between the moisture barrier layer(s) 14 and gas barrier layer 12, such that the need for an additional adhesive layer(s) 40 will be eliminated. However, it will also be appreciated that utilization of blends of polymers in the gas barrier layer 12 may result in a reduction in the barrier properties of the multilayered barrier structure 10.

Non-limiting examples of adhesive layers 40 according to the present invention include functionalized polyolefins, such as anhydride modified polypropylenes, acid modified polyolefins, acid/anhydride modified polyolefins, or other similar adhesive polymers, copolymers or blends, such as ethylene vinyl acetate copolymer (EVA). Examples of preferred adhesive polymers include Admer™ QF551A, a polypropylene graft copolymer adhesive (Mitsui Plastics, Inc.), and Plexar™ 420, a propylene/ethylene copolymer adhesive (Quantum Chemical Corp.).

It will be appreciated that the adhesive layers 40 can comprise functionalized derivatives of mesocopolymers that exhibit many or all of the advantageous properties, such as radiation resistance, and increased toughness, heat-sealability, softness and/or quietness, as well as providing sufficient adhesion to affix the moisture barrier layer 34 and gas barrier layer 32 together. For example, it is within the scope of the present invention for functionalized adhesive copolymers, such as Admer™ and Plexar™ to comprise the moisture barrier layer 14 of the present invention, quenched to preserve the mesophase form of the mesocopolymer after hot melt extrusion. In such an embodiment, the adhesive moisture barrier layer 14 could be affixed to other layers or surfaces to provide for specialized multilayered barrier structures 10 according to the present invention 10. For example, an adhesive moisture barrier layer 14 could have a woven or nonwoven layer affixed thereto, to provide a more comfortable surface against a wearers skin when the multilayered barrier structure 10 is incorporated into an ostomy pouch or the like. However, it will also be appreciated that any adhesive which is compatible with the gas barrier layers 12 and moisture barrier layers 14 according to the present invention, is considered to fall within the scope of the present invention.

Tempering Additives

As noted above, utilization of mesophase propylene-based materials, such as mesomorphous polypropylene, mesopolymer blends, and/or mesocopolymers, in the moisture barrier layer 14 of the multilayered barrier structure 10 can result in a softer and/or quieter structure than a comparable structure containing crystalline polypropylene. It has also been discovered that incorporation of a tempering additive, as that term is defined herein, into one or more of the layers of the multilayered barrier structure 10 results in a structure which is quieter when wrinkled or rustled, and/or which is softer in terms of compliability and drape, than the corresponding structure lacking in the tempering additive. Non-limiting examples of tempering additives include ethylene copolymers, such as ethylene vinyl acetate copolymer (EVA) and ethylene acrylic acid copolymer (EAA), polybutylene, polybutylene copolymers, or combinations thereof. Preferred tempering additives include EVA, EAA, polybutylene, and combinations thereof.

In a preferred embodiment, an effective amount of the tempering additive is incorporated into the moisture barrier layer 14, either as the second polymer of the mesopolymer blend, or as an optional additive with the mesomorphous polypropylene, mesopolymer blend, and/or mesocopolymer of the moisture barrier layer 14. For example, the moisture barrier layer 14 of the present invention can comprise a mesopolymer blend with EVA copolymer incorporated therein. Incorporation of EVA copolymer into the moisture barrier layer 14 of the multilayered barrier structure 10 according to the present invention results in a multilayered barrier structure 10 which is substantially quieter (as measured by frequency of sound emitted in Hertz) when wrinkled or rustled, than a comparable structure containing crystalline polypropylene and/or crystalline copolymers. Furthermore, incorporation of EVA copolymer into the moisture barrier layer 14, or other layers of the multilayered barrier structure 10, can lower the modulus (Young's Modulus) of the moisture barrier layer 12, resulting in a softer multilayered barrier structure 10.

Other Additives

Totally optionally, to provide specific additional properties to the multilayered barrier structure 10 of the present invention, the moisture barrier layer(s) 14, the gas barrier layer 12, and/or the adhesive layers 40, may also contain conventional additives such as antistatic materials, pigments, dyes, fillers, plasticizers, ultraviolet absorbers, quenching agents such as mineral oil, and the like. However, the mesophase propylene-based materials, including the mesomorphous polypropylene, mesopolymer blends, and/or mesocopolymers, of the moisture barrier layer 14 do not require any stabilizers, anti-oxidants or the like to enable the mesophase propylene-based materials, and accordingly, the resulting moisture barrier layer 14 and multilayered barrier structure 10, to withstand the effects of ionizing radiation, and still substantially maintain the structural integrity of the multilayered barrier structure 10 for a useful period of time after irradiation.

Properties of Multilayered Barrier Structures

In general, non-chlorine containing organic polymers, such as the preferred EVOH copolymer comprising the gas barrier layer 12 of the multilayered barrier structure 10 of the present invention, rapidly degrade after being exposed to ionizing radiation, such as gamma or electron-beam radiation. Furthermore, the penetrating nature of ionizing radiation would be expected to cause such a degradation of non-chlorine containing organic polymers, even when layered within a multilayered structure or film. Surprisingly, incorporation of a gas barrier layer 32 and optional adhesive layers 40, in conjunction with one or more moisture barrier layers 34, into a multilayered barrier structure 30 according to the present invention, results in a multilayered barrier structure 30 with increased resistance to ionizing radiation. Specifically, even after ionizing radiation dosages from about 1 kGy (0.1 Mrad) to 200 kGy (20.0 Mrad), the multilayered barrier structure 30 degrades at a substantially slower rate than a comparable structure with moisture barrier layers lacking mesomorphous polypropylene, mesopolymer blends, and/or mesocopolymers.

In addition to increased radiation resistance, the combination of a moisture barrier layer 14 and a gas barrier layer 12 into a multilayered barrier structure 10 according to the present invention synergistically increases the softness (i.e, decreases the stiffness, as measured by the Young's Modulus and the yield stress), the toughness (as measured by the fracture strain), and the quietness (as measured in Hertz (Hz) of sound emitted), of the multilayered barrier structure 10 above that which would be expected under the Rule of Mixtures, as that term is defined above. In addition, this synergistic effect on the softness, toughness, and/or quietness of the multilayered barrier structure 10 can be further enhanced when a tempering additive, as that term is defined above, is incorporated into the moisture barrier layer 14 of the multilayered barrier structure 10. Also, when using a moisture barrier layer 14 formed from mesopolymer blends according to the present invention, the multilayered barrier structures 10 can exhibit enhanced properties which are, at least in part, characteristic of the second polymers used in the mesopolymer blends of the moisture barrier layers 14. For example, use of polybutylene along with mesomorphous polypropylene in a mesopolymer blend comprising the moisture barrier layers 14 enhances the heat sealability and toughness of the overall multilayered barrier structure 10.

Furthermore, the radiation resistance provided by mesophase propylene-based materials, such as mesomorphous polypropylene, mesopolymer blends, and/or mesocopolymers, serves to maintain these enhanced characteristics for a useful period of time after ionizing irradiation at sterilization dosages. Thus, the multilayered barrier structure 10 of the present invention can withstand ionizing radiation, such as gamma radiation, which is employed to sterilize the structure or an article formed therefrom. Generally, it is desirable that the dosage of gamma radiation be in the range from about 1 kGy (0.1 Mrad) to about 200 kGy (20 Mrad), and preferably in the range from about 10 kGy (1 Mrad) to about 60 kGy (6 Mrad) for sterilization of medical articles.

Importantly, the elimination of chlorine-containing compounds as components of the gas barrier layer 12, moisture barrier layers 14, optional adhesive layers 40, or as additives to these layers, provides an environmentally compatible, multilayered barrier structure 10, which can be disposed of, such as through incineration, without endangering humans. Thus, various environmental hazards associated with the disposal of typical barrier materials, such as poly(vinylidene chloride) (PVDC) and poly(vinyl chloride) (PVC), can be avoided. In particular, materials such as PVDC and PVC release hazardous substances, such as hydrochloric acid (HCl), polychlorinated dibenzodioxin, and furan toxins during incineration. In contrast, the materials comprising the multilayered barrier structure 10, according to the present invention are broken down to environmentally compatible water and carbon dioxide during incineration.

Methods of Preparation

The process of blending known mixtures of polymers is well known to those skilled in the art. See e.g., Mathews, *Polymer Mixing Technology*, Chapter 3 (Applied Science Publishers, Essex, England, 1982), the disclosure of which is herein incorporated by reference. In the case of the present invention, the method of blending involves the use of an extruder by feeding the polymers (in the proper weight percentages, and where need be, after being dry-blended or compounded together) through a heated coextrusion process. Thus when a mesopolymer blend is to be employed, polypropylene and the second polymer are first dry blended together prior to being melt extruded as the moisture barrier layer 14. Furthermore, the non-chlorine containing organic polymer of the gas barrier layer 12, and functionalized polyolefin of the optional adhesive layer 40, are heated and coextruded with the moisture barrier layer 14 to form the multilayered barrier structure 10 according to the present invention.

Coextrusion is a polymer processing method for bringing diverse polymeric materials together to form unitary layered structures, such as films, sheets, fibers, and tubing. This allows for unique combinations of materials, and for structures with multiple functions, such as, barrier characteristics, radiation resistance, and heat sealability. By combining coextrusion with blown film processing, film structures can be made which have no inherent waste and much lower capital investment over flat film coextrusion. However, flat film processing techniques provide an excellent method for making the multilayered barrier structures 10,30 according to the present invention.

Component polymer or copolymer materials according to the present invention can be coextruded from the melt state in any shape which can be rapidly cooled to obtain a multilayered barrier structure 10 with a moisture barrier layer 14 which includes mesophase propylene-based materials. The shape and/or thickness of the coextruded structure will be dependent upon the efficiency of the particular extrusion equipment employed and the quenching systems utilized. Generally, films and tubes are the preferred coextruded structures. Only under appropriate, low temperature conditions (i.e., below 60° C.), can multilayered barrier structures 10 be uniaxially, biaxially or multiaxially oriented to further enhance their barrier and physical properties without losing the mesophase form of polypropylene or mesocopolymers in the moisture barrier layer(s) 14.

To obtain multilayered barrier structures 10 with a moisture barrier layer 14 having mesophase propylene-based materials, such as mesomorphous polypropylene, mesopolymer blends, and/or mesocopolymers, the coextruded structures must be quenched in a manner such that the mesophase form of polypropylene and/or mesocopolymer is obtained. Miller, "On the Existence of Near-Range Order in Isotactic Polypropylenes", in *Polymer, One*, 135 (1960), and U.S. Pat. No. 4,931,230, both of the disclosures of which are herein incorporated by reference, disclose suitable methods known to those skilled in the art for the preparation of mesophase form of polypropylene.

As described by these publications, various known methods of quenching as soon as possible, and preferably, immediately after extrusion, can be used to obtain a mesomorphous polypropylene homopolymer, mesopolymer blend, and/or mesocopoly having the mesophase form of polypropylene and/or mesocopolymer therein. Quenching methods include plunging the coextruded structure into a cold liquid, for example, an ice water bath (i.e., quench bath), spraying the coextruded structure with a liquid, such as water, hitting the film with a stream of cold air, and/or running the coextruded structure over a cooled roll, quench roll, or drum.

The coextruded multilayered barrier structure 10 of the present invention is preferably quenched immediately after extrusion by contact with a quench roll, or by being plunged into a quench bath. For a film thickness of from about 6μ to about 625μ, where a quench roll is used, roll temperature is maintained at a temperature below about 38° C., preferably below about 24° C., and the coextrudate is generally in contact with the quench roll until solidified. The quench roll should be positioned relatively close to the coextruder die, the distance being dependent on the roll temperature, the extrusion rate, the film thickness, and the roll speed. Generally, the distance from the die to the quench roll is about 0.25 cm to 5 cm. Where a quench bath is used, the bath temperature is preferably maintained at a temperature below about 4° C. The bath should be positioned relatively close to the die, generally from about 0.25 cm to 13 cm from the die to the quench bath.

As noted above, the coextruded multilayered barrier structure 10 according to the present invention should not be subjected to any treatment, such as orientation or stretching, at temperatures above 60° C. Specifically, the employment of such treatment techniques at temperatures above 60° C. would transform the mesophase form of propylene-based materials in the moisture barrier layer 14 of the multilayered structure 10 to predominantly undesired crystalline form of propylene-based materials.

Usefulness of the Invention

In a preferred construction, the multilayered barrier structure 10 according to the present invention comprises a five-layer barrier film 30 such as illustrated in FIG. 2, with a core gas barrier layer 32 of EVOH copolymer, two intermediate adhesive layers 40 of a functionalized polyolefin, and two outer moisture barrier layers 34 comprised of a mesophase propylene-based materials, such as mesomorphous polypropylene homopolymer, a mesopolymer blend of mesomorphous polypropylene and polybutylene, EVA copolymer, EAA copolymer, a mesocopolymer, or combinations of any of these polymers or copolymers.

Multilayered barrier films 10 according to the present invention will be especially useful in ostomy pouch applications, Where security from odor, integrity of the device, and integrity of the underlying materials are requirements. Multilayered barrier films 10 can be die cut and heat sealed with conventional equipment, and are compatible with current attachment systems and ostomy pouch manufacturing practices. Since the multilayered barrier films 10 are moisture resistant both inside and out, the resulting ostomy pouch is capable of being worn during swimming and showering. Optionally, with incorporation of a polymeric tempering additive, such as EVA copolymer, EAA copolymer, polybutylene, polybutylene copolymers, or combinations thereof, into various layers of the barrier film 10, the resulting ostomy pouch can be quieter when wrinkled or rustled during the movements of a wearer of such a pouch. In addition, other useful articles such as tapes, tubings, containers, transdermal drug-delivery patches and various packaging materials can also be formed from the multilayered barrier film 10 of the present invention. Thus, the multilayered barrier film 10 of the present invention is useful to form or cover a protective environment from an external environment, such that moisture and/or gases cannot substantially pass through to a degradable product contained therein, or a surface covered thereby. For example, the multilayered barrier film 10 can be used to contain a food product or a pharmaceutical product in a protected environment, to which moisture and/or gases from the external environment cannot substantially pass into. Similarly, the multilayered barrier film 10 can comprise a transdermal drug delivery patch, or medical tape, or an ostomy pouch, which protects the body of a mammal, or the waste products generated by the mammal, from degradation due to exposure to moisture and/or gases in the external environment.

Other Layers and Modifications

Articles formed from the multilayered barrier structures 10,30 need not be limited to three-layered and five-layered examples illustrated in FIGS. 1 and 2. In addition, these multilayered barrier structures 10,30 can be further modified for specialty applications by adding additional layers thereto. For example, a specialty ostomy pouch comprising a multilayered barrier structure 10 of the present invention could be formed by laminating a fabric backing of a woven or nonwoven material (not shown) to a surface of the ostomy pouch. This fabric backing would act to provide a soft layer against a wearer's skin, and thus make the ostomy pouch more comfortable and non-clinging.

A fabric backing could be applied to the multilayered barrier structure 10 of the present invention in a number of different ways. For example, a layer of a nonwoven material, formed from a polymer such as polypropylene, could be affixed to the multilayered barrier structure 10 of the present invention by an intervening adhesive layer. Preferably, such an adhesive layer would comprise a functionalized mesocopolymer according to the present invention. In addition, a fabric backing could be affixed to the multilayered barrier structure 10 by running both layers through hot rollers or nips, that would heat seal the fabric and barrier layers together. In such a heat sealing operation, it would be preferred to maintain the hot rollers at sufficient temperature to provide an effective heat seal between the layers without substantially affecting the mesophase form of the mesomorphous polypropylene, mesopolymer blends, and/or mesocopolymers of the moisture barrier layer(s) 14 of the multilayered barrier structure 10.

As an alternative, a fabric backing could be applied to the multilayered barrier structure 10 of the present invention by affixing a web of melt blown microfibers thereto. For example, melt blown polymer microfibers could be hot melt extruded from a die into a high velocity air stream, and onto a surface of the multilayered barrier structure 10 according to the present invention. See, e.g., Report No. 4364 of the Naval Research Laboratories, published May 25, 1954, entitled "Manufacture of Superfine Organic Fibers", by V. A. Wente et al., and V. W. Wente et al., "Superfine Thermoplastic Fibers", 48, *Industrial Engineering Chemistry*, 1342 (1956), both of the disclosures of which are herein incorporated by reference. In a preferred embodiment, the melt blown microfiber web affixed to at least one side of the multilayered barrier structure 10 could be formed of mesomorphous polypropylene, mesopolymer blends, and/or mesocopolymers, by quenching the hot blown microfibers immediately after extrusion. For example, the microfibers could be quenched by spraying the fibers with a liquid such as water, or by collecting the fibers on the multilayered barrier structure 10 that is in contact with a cooled collector drum or roll.

In addition, the outer surfaces of the multilayered barrier structure of the present invention may also desirably have one or more graft layers affixed thereto to enhance other properties such as surface adhesion, oxygen and/or moisture permeability, coefficient of friction, or other properties desirable to those skilled in the art. For example, not be way of limitation, surface adhesion is desirable in order to provide the application of primers and other coatings that would not otherwise adhere well to the structures of the present invention.

Preferably, a graft layer, such as a surface adhesion layer, is grafted to the outer surfaces of the multilayered barrier structures 10 by electron beam radiation at dosages of from about 5 kGy (0.5 Mrad) to about 200 kGy (20 Mrad), and preferably at about 50 kGy (5 Mrad), according the procedures provided in U.S. Pat. No. 4,950,549, the disclosure of which is herein incorporated by reference. Non-limiting examples of compounds that can be grafted to the multilayered structures of the present invention to form a surface adhesion layer include acrylic acid (AA), dimethylacrylamide (DMA), N-vinyl-2-pyrrolidone (NVP), and a copolymer of NVP and trimethylolpropane-triacrylate (NVP/TMPTA). Other potential compounds that can also be used as a graft layer include glycidyl acrylate, hydroxyethyl acrylate, hydroxymethyl acrylate, 2-vinyl pyridine, sulfoethyl methacrylate, diisopropylacrylamide, or N,N-diethylamino acrylate. Particularly preferred grafting compounds used to form a surface adhesion layer on a least a portion of the multilayered structures according to the present invention include AA (Aldrich Chemical Co., Milwaukee, Wis.) and DMA (Chem Services, Inc., Westchester, Pa.).

The following non-limiting examples are provided to further illustrate the invention.

EXAMPLES 114 4 AND 6, AND COMPARISON EXAMPLES 5 AND 7–10

Ten, five-layered coextruded barrier films were made using a flat film process consisting of 3 extruders, a 5-layer Cloeren™ feedblock (Cloeren Company, Orange, Tex.), and a single manifold film extrusion die. The barrier films were generally coextruded at a film thickness of about 75 μ, with each moisture barrier layer (hereinafter layer "A") being about 30μ thick, each adhesive layer (hereinafter layer "B") being about 4μ thick, and the gas barrier layer (hereinafter layer "C") being about 8μ thick. The construction of the five-layered barrier films corresponded to the multilayered structure illustrated in FIG. 2 herein.

Layer A comprised mixtures by weight of polypropylene resin (hereinafter "PP") (PP3576; Fina Oil and Chemical Co.; melt index=9 g/10 min.), and polybutylene resin (hereinafter "PB") (PB400; Shell Chemical Co.; melt index= 20 g/10 min.). Layer B comprised a polypropylene based adhesive layer of Admer™ QF551A resin (Mitsui Plastics, Inc.; melt index=5.7 g/10 min.) Layer C was made of an ethylene-vinyl alcohol copolymer (hereinafter "EVOH") (EVAL™, E105 Evalca Co; melt index =5.5 g/10 min.)

The PP/PB mixtures were dry blended before being melted and coextruded. Film extrusion conditions for Examples 1–4 and 6, and Comparison Examples 5 and 7–10 are given in Table 1. Table 2 lists specific film constructions for layer A of the Example and Comparison Example films and their casting roll (quench) temperatures. The temperature of the quench roll for Examples 1–4 was maintained at 10° C., and at −1° C. for Example 6, in order to control the mesomorphous structure of the polypropylene in the polymer blend. The multilayered films were coextruded onto a quench roll spaced 2.54 cm from the extrusion die. The films were in contact with the quench roll for about 2 seconds and were coextruded at a rate of about 17 meters per minutes (mpm). The adhesive layer and barrier layer constructions were kept constant across all of the Examples and Comparison Examples.

Thickness of each layer in the multilayered barrier films of Examples 1–4 and 6, and Comparison Examples 5 and 7–10 was determined via optical microscopy from film cross-sections. Samples of each of the Example films were cut and trimmed, and then embedded in 3M Scotchcast™ Brand electrical resin No. 8 (3M, st. Paul, Minn.). The films were then cut into cross-sections using a microtome. Specimens were placed on a glass slide in immersion oil with a cover slip placed on top. Layer thicknesses were then determined via transmitted bright field optical microscopy. Values for the moisture barrier layer thicknesses (designated as layers 1A and 2A), adhesive layer thicknesses (designated as layers 1B and 2B), core gas barrier. layer thickness (designated as layer C), and total film thickness are shown in Table 3.

TABLE 1

Film extrusion conditions for Examples 1–4 and 6, and for Comparison Examples 5 and 7–10.

| Layer | Melt Temperature (°C.) | Screw Speed (RPM) | Die Temperature (°C.) |
|---|---|---|---|
| A | 221 | 59 | 232 |
| B | 232 | 18 | 232 |
| C | 237 | 20 | 232 |

TABLE 2

Weight percentage ratio of polypropylene (PP) to polybutylene (PB), and casting (quench) roll temperatures layer A of Examples 1–4 and 6, and Comparison Examples 5 and 7–10.

| Example Number | Ratio PP:PB (wt %) | Casting Roll Temperature (°C.) |
|---|---|---|
| Ex. 1 | 100/0 | 10 |
| Ex. 2 | 80/20 | 10 |
| Ex. 3 | 50/50 | 10 |
| Ex. 4 | 20/80 | 10 |
| Comp. Ex. 5 | 0/100 | 10 |
| Ex. 6 | 50/50 | −1 |
| Comp. Ex. 7 | 100/0 | 66 |
| Comp. Ex. 8 | 80/20 | 66 |
| Comp. Ex. 9 | 50/50 | 66 |
| Comp. Ex. 10 | 50/50 | 66 |

TABLE 3

Moisture barrier layer thicknesses (1A and 2A), adhesive layer thicknesses (1B and 2B), gas barrier layer thickness (C), and total film thickness in microns (μ), for Examples 1–4 and 6, and for Comparison Examples 5 and 7–10.

| Example | Layer 1A (μ) | Layer 1B (μ) | Layer C (μ) | Layer 2B (μ) | Layer 2A (μ) | Film Thickness Total |
|---|---|---|---|---|---|---|
| Ex. 1 | 37 | 5 | 11 | 2 | 40 | 95 |
| Ex. 2 | 38 | 4 | 12 | 5 | 39 | 97 |
| Ex. 3 | 37 | 3 | 8 | 4 | 35 | 87 |
| Ex. 4 | 32 | 3 | 11 | 3 | 39 | 86 |
| Comp. Ex. 5 | 37 | 2 | 14 | 5 | 40 | 98 |
| Ex. 6 | 35 | 2 | 10 | 3 | 35 | 85 |
| Comp. Ex. 7 | 38 | 5 | 12 | 3 | 37 | 94 |
| Comp. Ex. 8 | 31 | 5 | 11 | 5 | 30 | 81 |
| Comp. Ex. 9 | 26 | 4 | 12 | 7 | 31 | 80 |
| Comp. Ex. 10 | 27 | 5 | 12 | 5 | 34 | 82 |

Figure 12:
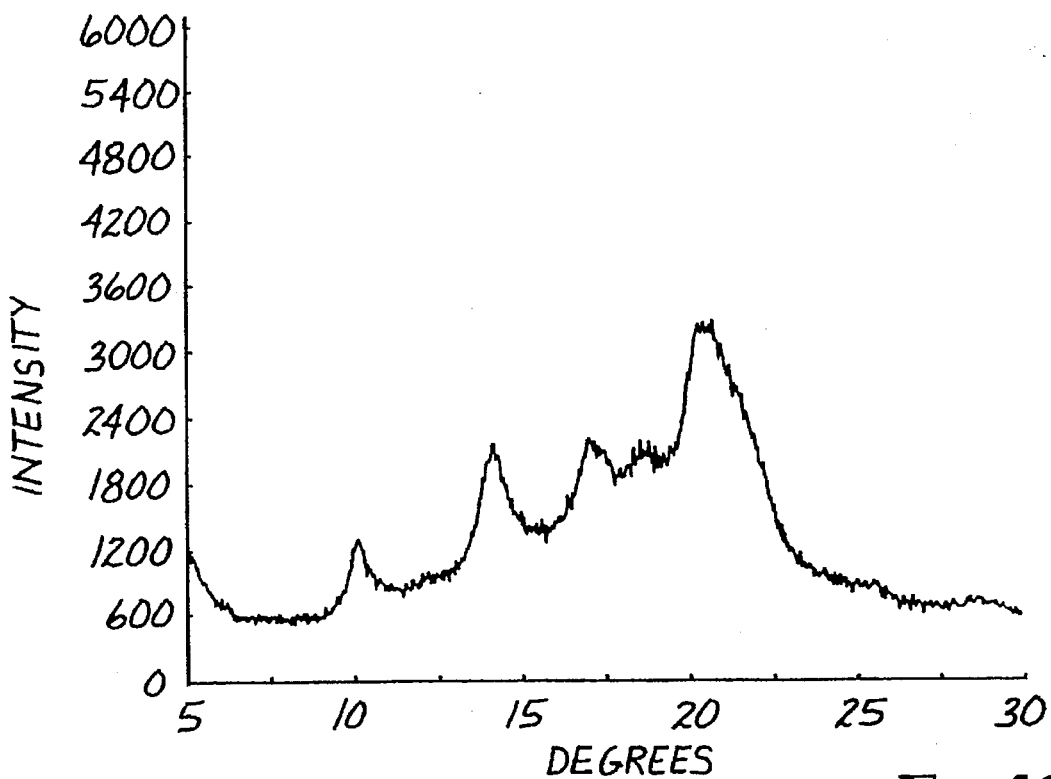
FIG. 12 is another wide-angle x-ray diffraction pattern of a 50/50 blend by weight of crystalline polypropylene with polybutylene.
Figure 3:
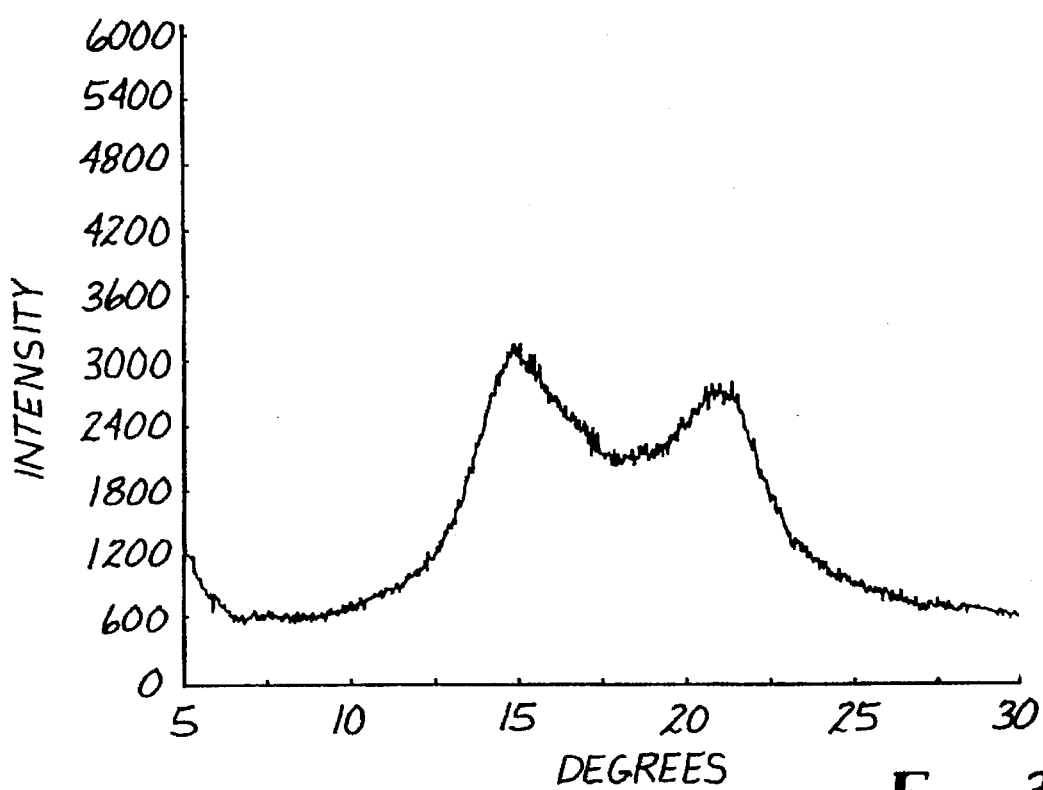
FIG. 3 is the wide-angle x-ray diffraction pattern of mesomorphous polypropylene.
Figure 4:
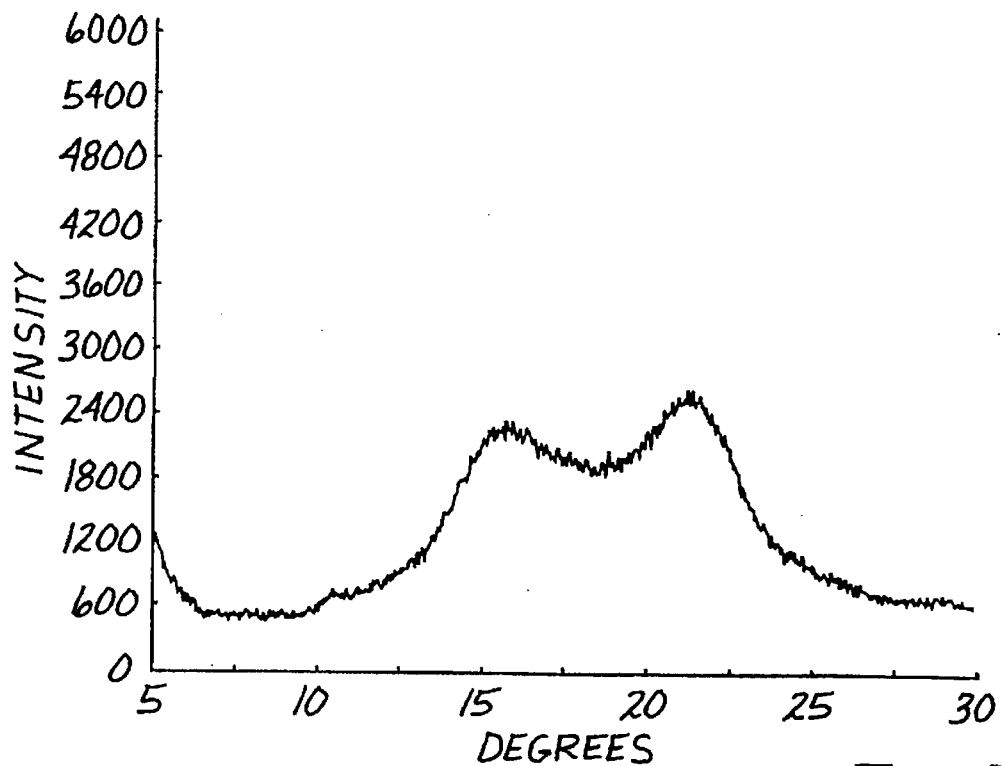
FIG. 4 is the wide-angle x-ray diffraction pattern of an 80/20 mesopolymer blend by weight of mesomorphous polypropylene with polybutylene.
Figure 5:
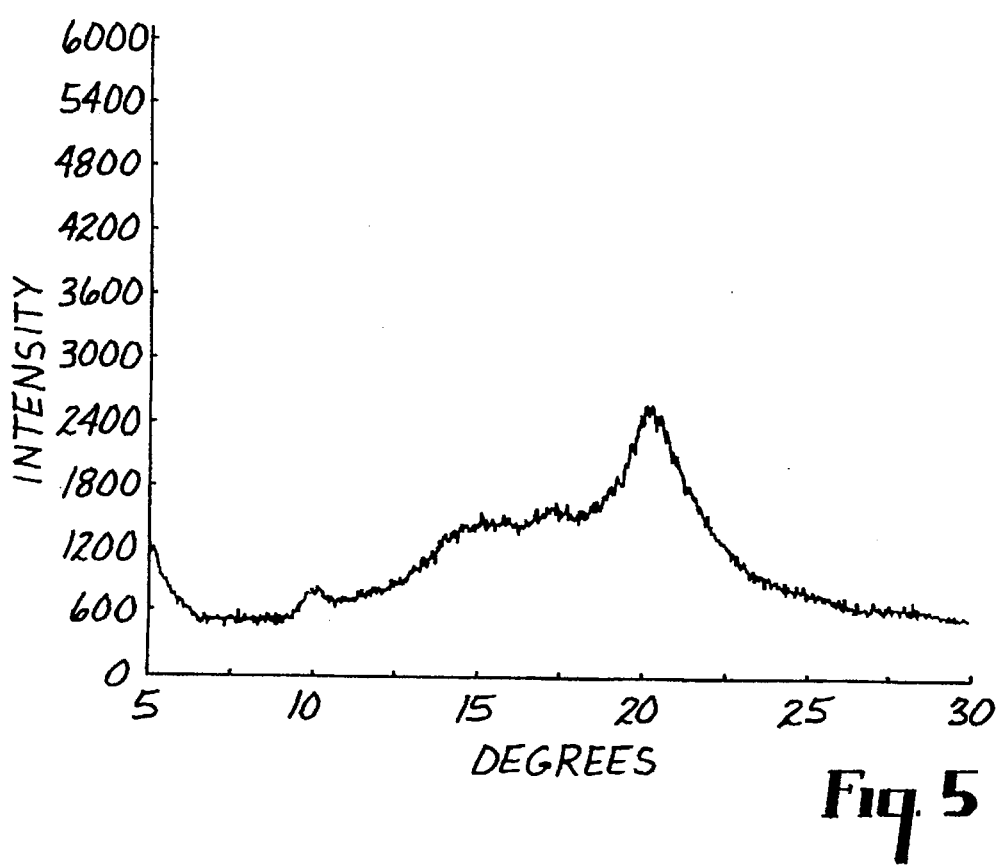
FIG. 5 is the wide-angle x-ray diffraction pattern of a 50/50 mesopolymer blend by weight of mesomorphous polypropylene with polybutylene.
Figure 6:
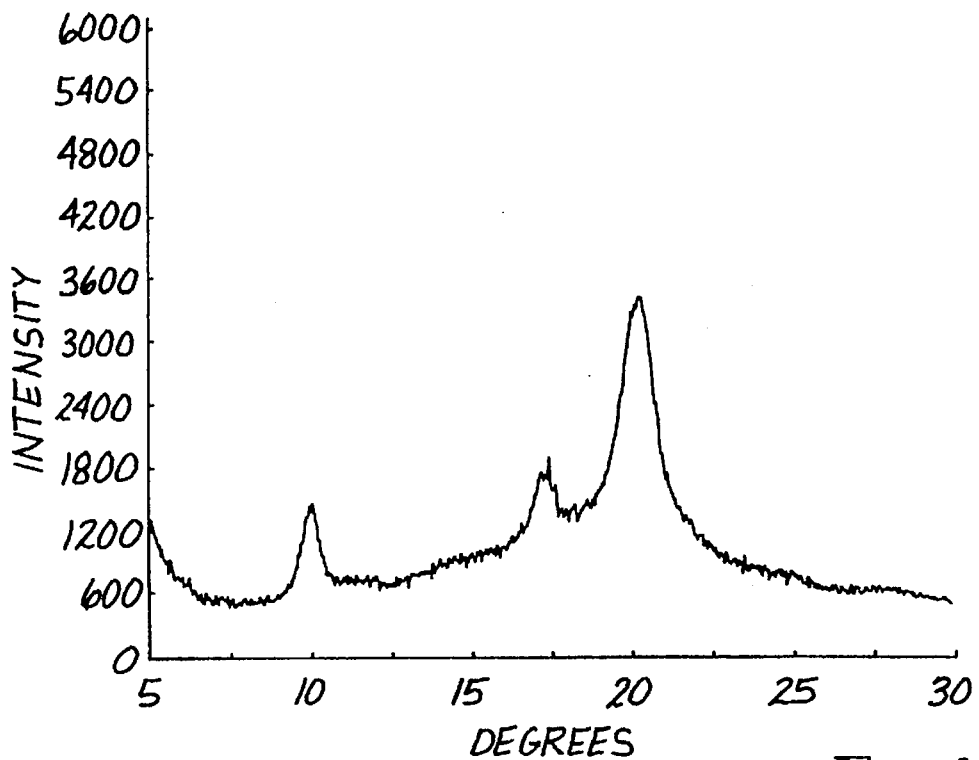
FIG. 6 is the wide-angle x-ray diffraction pattern of a 20/80 mesopolymer blend by weight of mesomorphous polypropylene with polybutylene.
Figure 7:
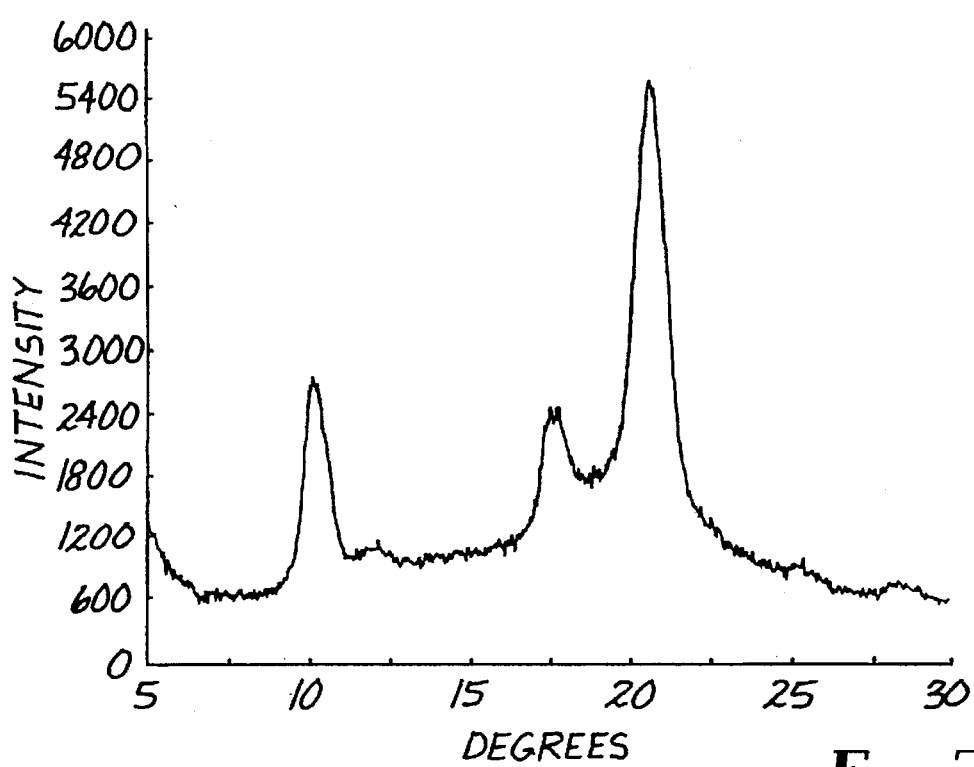
FIG. 7 is the wide-angle x-ray diffraction pattern of polybutylene.
Figure 8:
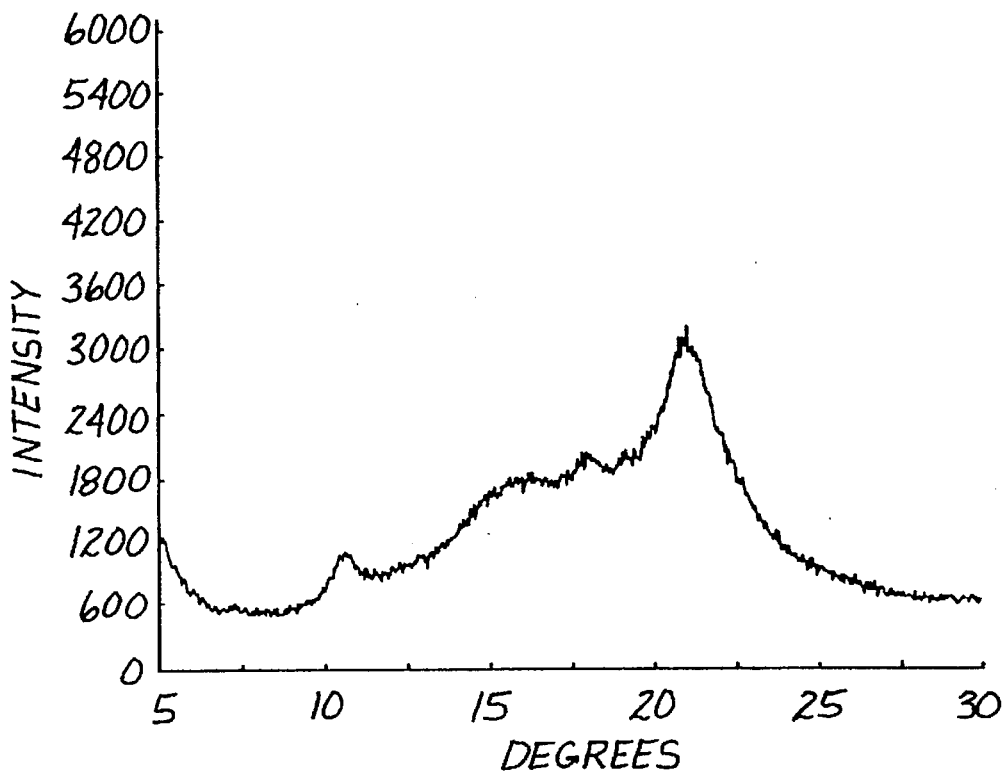
FIG. 8 is the wide-angle x-ray diffraction pattern of a 50/50 mesopolymer blend by weight of mesomorphous polypropylene with polybutylene.
Figure 9:
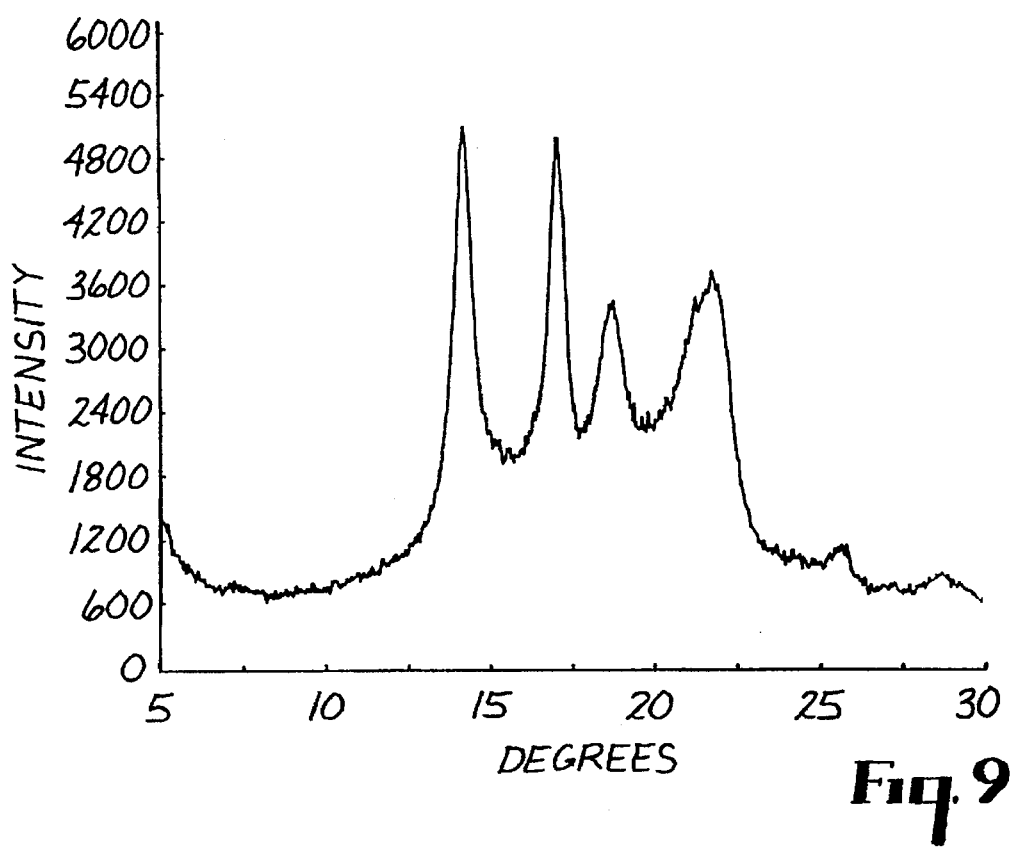
FIG. 9 is the wide-angle x-ray diffraction pattern of crystalline polypropylene.
Figure 10:
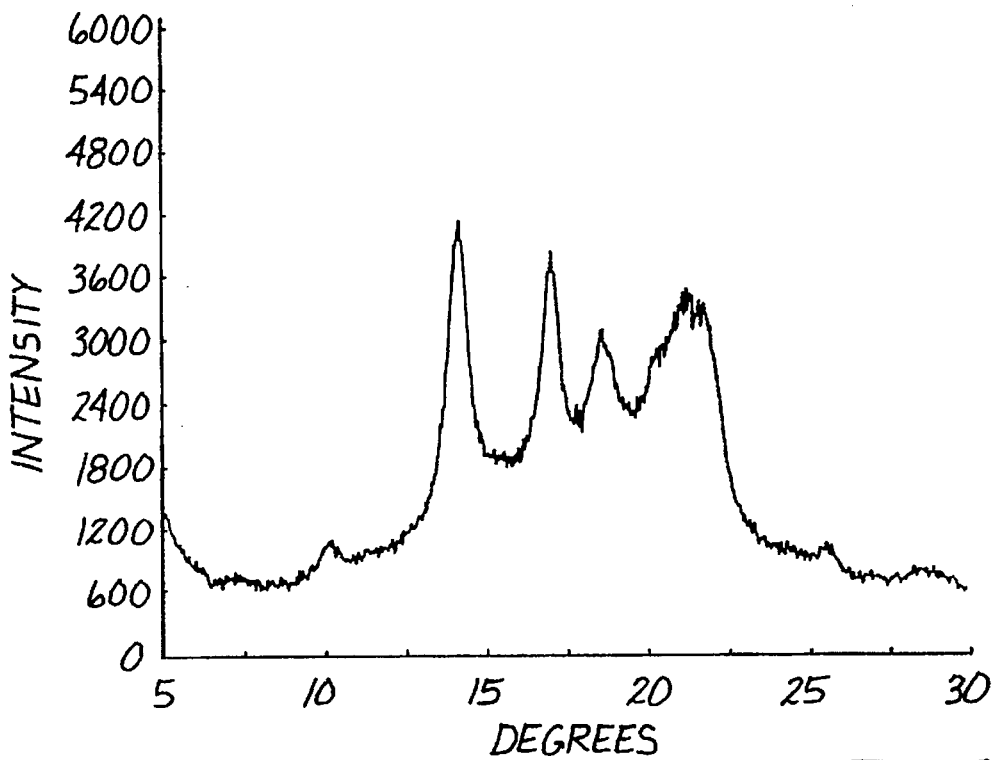
FIG. 10 is the wide-angle x-ray diffraction pattern of an 80/20 blend by weight of crystalline polypropylene with polybutylene.
Figure 11:
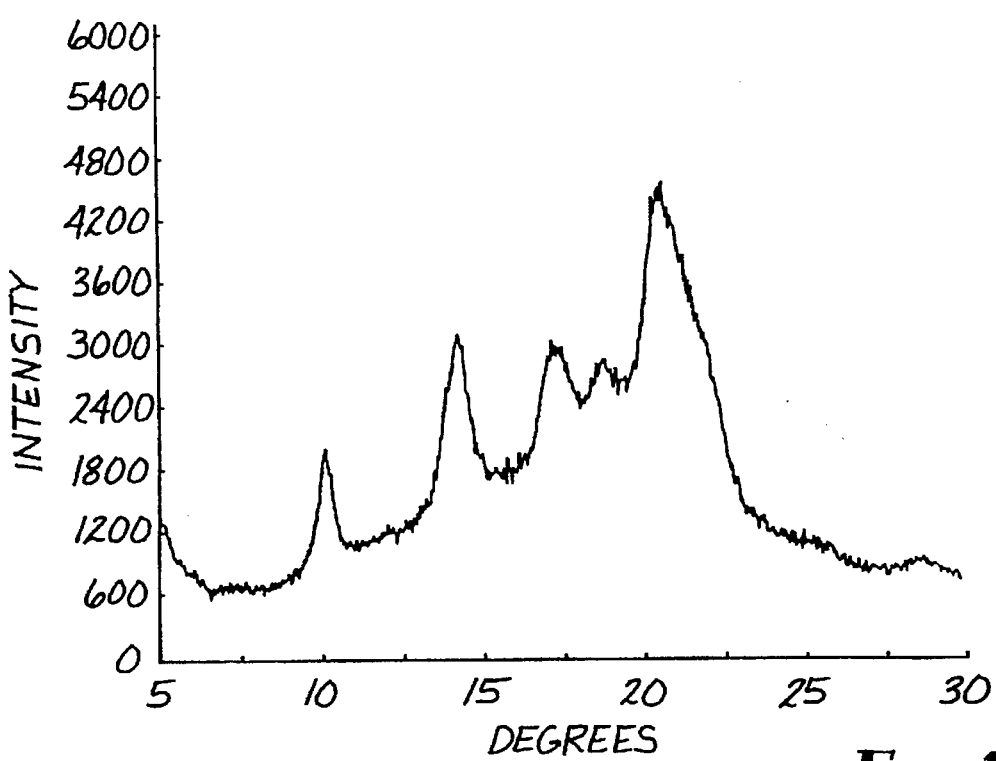
FIG. 11 is the wide-angle x-ray diffraction pattern of a 50/50 blend by weight of crystalline polypropylene with polybutylene.

The crystalline structure, or mesomorphous structure, for each of the multilayered barrier films of Examples 1–4 and 6, and for Comparison Examples 5 and 7–10 was determined by wide-angle x-ray diffraction (WAXD). Graphical illustrations of the WAXD scans for each of the Example and Comparison Example films are shown in FIGS. 3 through 12 herein. The mesophase form (i.e., mesomorphous polypropylene) is clearly shown in FIGS. 3–6 and 8. FIG. 7 shows the sharp peaks associated with crystalline polybutylene, while the very sharp peaks in the WAXD scan shown in FIGS. 10–12 are due to the crystalline phases of both polypropylene and polybutylene. The WAXD data for polypropylene present in the Example and Comparison Example films is summarized in Table 4.

TABLE 4

Structure of the polypropylene homopolymer and polymer blends of Examples 1-4 and 6, and for Comparison Examples 5 and 7-10, as determined by WAXD.

| Example Number | Ratio PP/PB (wt %) | WAXD PP | Casting Roll Temperature (°C.) |
|---|---|---|---|
| Ex. 1 | 100/0 | Mesomorphous | 10 |
| Ex. 2 | 80/20 | Mesomorphous | 10 |
| Ex. 3 | 50/50 | Mesomorphous | 10 |
| Ex. 4 | 20/80 | Mesomorphous | 10 |
| Comp. Ex. 5 | 0/100 | na | 10 |
| Ex. 6 | 50/50 | Mesomorphous | -1 |
| Comp. Ex. 7 | 100/0 | Crystalline | 66 |
| Comp. Ex. 8 | 80/20 | Crystalline | 66 |
| Comp. Ex. 9 | 50/50 | Crystalline | 66 |
| Comp. Ex. 10 | 50/50 | Crystalline | 66 |

Figure 13:
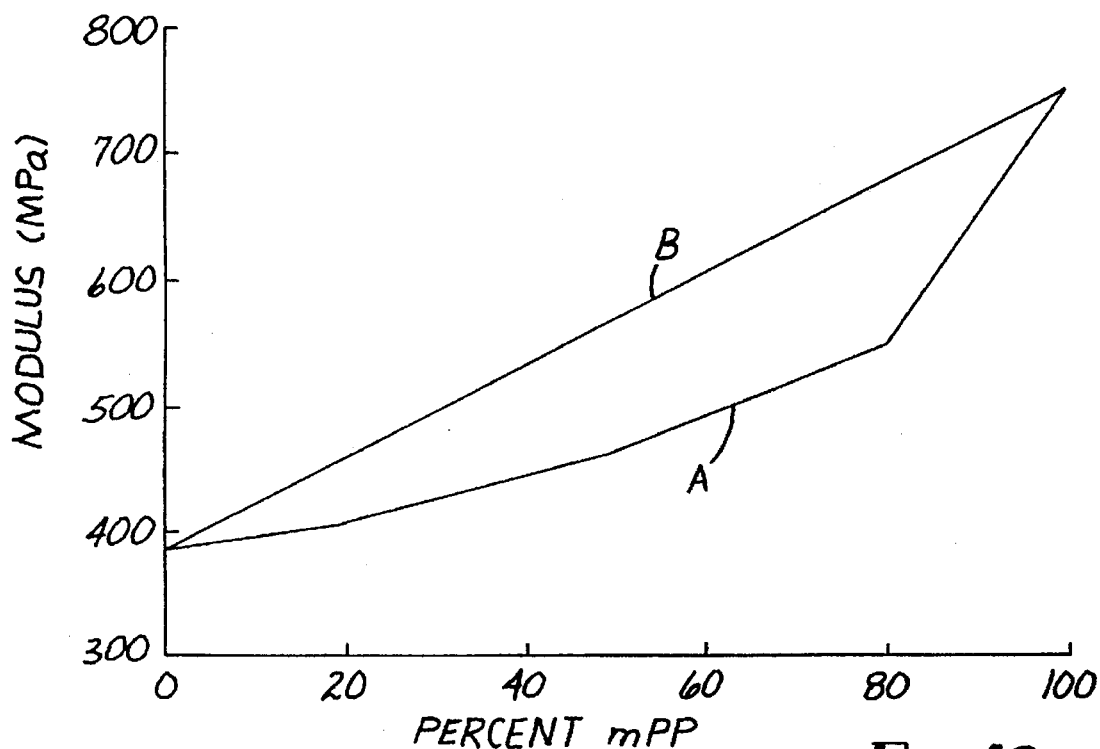
FIG. 13 is a graph comparing Young's modulus of the multilayered barrier structures of Examples 1–4 and Comparison Example 5 (line A) with hypothetical linear values for Examples 1–4 and Comparison Example 5 (line B)
Figure 14:
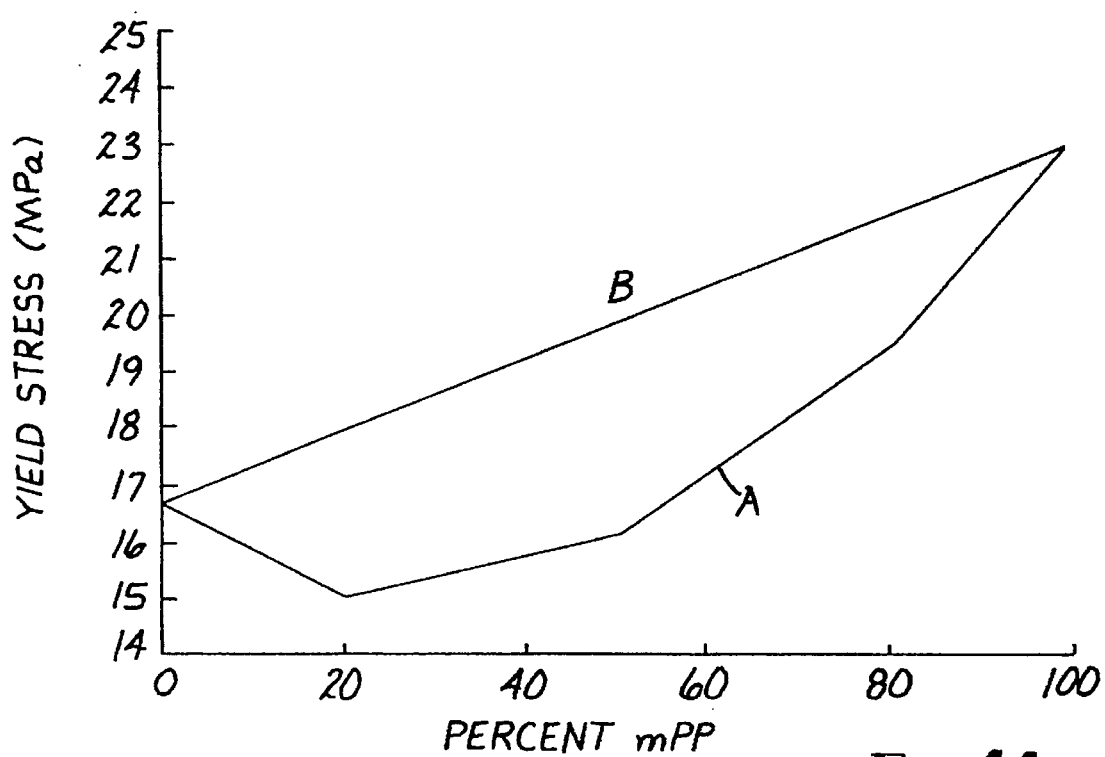
FIG. 14 is a graph comparing the yield stress of the multilayered barrier structures of Examples 1–4 and Comparison Example 5 (line A) with hypothetical linear values for Examples 1–4 and Comparison Example 5 (line B)

The tensile properties for the barrier films of Examples 1-4 and 6 and Comparison Examples 5 and 7-10 were determined on an Instron™ 1122 machine using 5 cm×2.5 cm samples of the Example and Comparison Example multilayered barrier films. Each sample was deformed at a strain rate of one thousand percent (1000%) per minute (sample gauge length of 5 cms and a crosshead speed of 51 cms per minute) using ASTM D882-88 procedures. In each case, at least three samples of each of the Example and Comparison Example films were measured for each value reported. Modulus values were calculated by taking modulus values determined using the Instron™ Model 1122 with the load cell amplifier switch set in the "IN" position and multiplying by two. When set in the "IN" position, a dampening of the recorder per servo occurs which (as demonstrated in subsequent analysis) can be corrected by multiplying by two. Effect of mesomorphous polypropylene (mPP) composition on modulus (Young's Modulus, as measured in Mega Pascals (MPa)) is shown in FIG. 13 (line A). As mPP concentration is reduced (or PB concentration in the mesopolymer blend is increased) the multilayered barrier film becomes less stiff (i.e., softer). As can be seen in FIG. 13, the modulus values for the mesopolymer blends are lower than would be expected from the Rule of Mixtures, as defined herein, and illustrated at line B. This synergy in softness is further reflected in the yield stress results as shown in FIG. 14. As with FIG. 13, the actual yield stress values illustrated by line A are considerably less than those which would be predicted under the Rule of Mixtures illustrated at line B. Furthermore, quenched (casting roll temperature of 10° C. or less) multilayered barrier films containing mPP in the outer layer blend were found to be 24 to 30% less stiff than similar compositions with crystalline PP (casting roll temperature at 66° C.), as shown in Table 5.

TABLE 5

Young's Modulus in Mega Pascals (MPa) of the multilayered barrier films of Examples 1-4 and 6, and Comparison Examples 5 and 7-10.

| Example Number | Ratio PP/PB (wt %) | Modulus (MPa) | Casting Roll Temperature |
|---|---|---|---|
| Ex. 1 | 100/0 | 752 | 10 |
| Ex. 2 | 80/20 | 546 | 10 |
| Ex. 3 | 50/50 | 462 | 10 |

TABLE 5-continued

Young's Modulus in Mega Pascals (MPa) of the multilayered barrier films of Examples 1-4 and 6, and Comparison Examples 5 and 7-10.

| Example Number | Ratio PP/PB (wt %) | Modulus (MPa) | Casting Roll Temperature |
|---|---|---|---|
| Ex. 4 | 20/80 | 406 | 10 |
| Comp. Ex. 5 | 0/100 | 386 | 10 |
| Ex. 6 | 50/50 | 452 | -1 |
| Comp. Ex. 7 | 100/0 | 984 | 66 |
| Comp. Ex. 8 | 80/20 | 780 | 66 |
| Comp. Ex. 9 | 50/50 | 622 | 66 |
| Comp. Ex. 10 | 50/50 | 600 | 66 |

Resistance to permeation of oxygen and moisture vapor was measured for the multilayered barrier films of Examples 1-4 and 6. Oxygen transmission rate ($O_2TR$) was determined using an Ox-Tran™ 1000H machine (Mocon, Inc., Minneapolis, Minn.). $O_2TR$ was collected at 25° C. and zero percent (0%) relative humidity. A square sample of each multilayer film was placed in the testing cell of the Ox-Tran™ oxygen permeability tester. Two samples of each film were tested in adjacent cells. Since the Ox-Tran™ 1000H machine has ten test cells, up to five films could be examined at any one time.

Each cell was purged for at least 24 hours with a "carrier" gas of nitrogen containing 1-3% hydrogen prior to testing, to remove any residual oxygen in the sample, cell and system. After purging was completed, a sample of the gases in each cell was tested for residual oxygen content or oxygen "leak rate". The leak rate value determined at each cell was used as the cell's residual oxygen baseline.

Next, each cell was conditioned for another 24 hours by passing 100% oxygen over one side of the sample. Oxygen on the other side of the sample was measured after this conditioning period. This total oxygen content included the amount of oxygen which permeated through the film plus any residual oxygen in the system. To obtain oxygen transmission rate through the film, the leak rate value was subtracted from the total oxygen measured.

Oxygen transmission rate data was collected for each film at 25° C. and 0% relative humidity. The values reported are the average of rates determined for two samples. Since oxygen transmission rate is inversely proportional to thickness, all values were normalized to a standard gas barrier layer thickness of 25µ by multiplying the oxygen transmission rate value by the ratio of barrier layer thickness (as reported in Table 3 herein) to 25µ.

Moisture vapor transmission rate (MVTR) for the Example films was determined using a Permatran™-W6 (Mocon, Inc., Minneapolis, Minn.). MVTR data was collected at 38.6° C. and one-hundred percent (100%) relative humidity. The reported values are the average of the values obtained for at least three samples of each Example film. Since MVTR is inversely proportional to thickness, all values were normalized to a standard moisture barrier layer thickness of 25µ (microns) by multiplying the MVTR value by the ratio of moisture barrier layer thickness (being the sum of the moisture barrier and adhesive layer thicknesses, as reported in Table 3 herein) to 25µ. The oxygen transmission rates ($O_2TR$) and moisture vapor transmission rates (MVTR) for Examples 1-4 and 6 are reported in Table 6. These rates demonstrate good oxygen and moisture barrier properties for the Example films of the present invention.

TABLE 6

Oxygen transmission rates (O₂TR), as expressed in cc/m²/day-atmosphere, and moisture vapor transmission rates (MVTR), as expressed in g/m²/day-atmosphere, for Examples 1–4 and 6.

| Ex. No. | Ratio PP/PB (Wt %) | Casting Roll Temp. (°C.) | O₂TR (cc/m²/d-atm) | MVTR (g/m²/d-atm) |
|---|---|---|---|---|
| 1 | 100/0 | 10 | 2.0 | 13.8 |
| 2 | 80/20 | 10 | 2.2 | 14.5 |
| 3 | 50/50 | 10 | 1.5 | 16.4 |
| 4 | 20/80 | 10 | 2.1 | 14.9 |
| 6 | 50/50 | -1 | 2.0 | 18.3 |

COMPARISON EXAMPLES 11–16

Six, five-layered coextruded barrier films were made on a standard polyethylene type, blown-film processing line using a five-layer blown film die. The barrier films were coextruded at a thickness of 75μ. The construction of the five-layered barrier films was analogous to the multilayered barrier structure construction illustrated in FIG. 2 herein. In particular, each moisture barrier layer (hereinafter "layer A") comprised a 50/50 mixture by weight of polypropylene (PP) (pp 3150; melt index=0.8 g/10 min.; Fina Oil and Chemical Co.) and polybutylene (PB)(PB 200; melt index 1.8 g/10 min. for Comparison Examples 11–13; and PB 1710A; melt index 1.0 g/10 min. for Comparison Examples 14–16; Shell Chemical Co.). Each adhesive layer (hereinafter "layer B") comprised a polypropylene copolymer (Plexar™ 420; melt index=2.5 g/10 min.; Quantum Chemical Corp.). The gas barrier layer (hereinafter "layer C"), comprised an ethylene-vinyl alcohol polymer (EVOH) (EVAL™ E151B; melt index=1.6 g/10 min.; Evalca Co.). The PP/PB mesopolymer blends were precompounded before being melted and coextruded.

The six barrier film constructions of Comparison Examples 11–16 are given in Table 7. Each of the films was cross-sectioned, and individual layer thicknesses were determined by optical microscopy according to the same procedures as for Examples 1–4 and 6 and Comparison Examples 5 and 7–10. Extrusion processing conditions for each of the layers of the multilayered barrier films of Comparison Examples 11–16 are shown in Table 8. The films were made 0.24 m wide at a 21 meters per min. (mpm) line speed. None of Comparison Examples 11–16 were quenched after hot melt coextrusion. Thus, these samples did not include any discernable amount of mesomorphous polypropylene in the moisture barrier layers.

TABLE 7

Individual layer thicknesses in microns (μ) for the barrier film constructions of Comparison Examples 11–16.

| Comparison Example Number | Layer C Thickness (Microns) | Layer B × 2 Thickness (Microns) | Layer A × 2 Thickness (Microns) |
|---|---|---|---|
| 11 | 4 | 4 × 2 | 33 × 2 |
| 12 | 8 | 4 × 2 | 31 × 2 |
| 13 | 15 | 4 × 2 | 27 × 2 |
| 14 | 4 | 4 × 2 | 33 × 2 |
| 15 | 8 | 4 × 2 | 31 × 2 |
| 16 | 15 | 4 × 2 | 27 × 2 |

TABLE 8

Individual processing conditions for each of the layers of the multilayered barrier film constructions of Comparison Examples 11–16.

| Individual Layer Process Conditions | Comp. Ex. 11 | Comp. Ex. 12 | Comp. Ex. 13 | Comp. Ex. 14 | Comp. Ex. 15 | Comp. Ex. 16 |
|---|---|---|---|---|---|---|
| Layer C Extruder (4 cm) | | | | | | |
| Screw Speed (rmp) | 25 | 50 | 100 | 25 | 50 | 100 |
| Melt Temperature (°C.) | 219 | 219 | 220 | 222 | 220 | 223 |
| Amps | 12 | 15 | 19 | 11 | 15 | 19 |
| Layer B Extruder (4 cm) | | | | | | |
| Screw Speed (rmp) | 75 | 75 | 75 | 75 | 75 | 75 |
| Melt Temperature (°C.) | 217 | 217 | 217 | 219 | 219 | 219 |
| Amps | 14 | 14 | 14 | 14 | 14 | 14 |
| Layer A Extruder (6 cm) | | | | | | |
| Screw Speed (rmp) | 97 | 97 | 97 | 97 | 97 | 97 |
| Melt Temperature (°C.) | 238 | 238 | 238 | 256 | 254 | 257 |
| Amps | 102 | 102 | 102 | 108 | 108 | 108 |
| Die Temperature (°C.) | 216 | 216 | 216 | 216 | 216 | 216 |
| Blow Up Ratio | 2:1 | 2:1 | 2:1 | 2:1 | 2:1 | 2:1 |
| Frost Line (cm) | 61 | 61 | 61 | 61 | 61 | 61 |

The tensile properties of each of the six barrier films of Comparison Examples 11–16 were performed on an Instron 1122™ machine according to the same procedures as employed in Examples 1–4 and 6, and Comparison Examples 5 and 7–10. Yield strain, fracture strain, yield stress, fracture stress and Young's modulus was obtained for each of Comparison Examples 11–16, and are shown in Table 9. At least three samples of each of the Comparison Example films were measured for each value reported.

TABLE 9

Yield strain, fracture strain, yield stress, fracture stress, and Young's modulus in Mega Pascal (MPa) for each of Comparison Examples 11–16.

| Comp Ex. | Layer C Thickness (μ) | Yield Strain (%) | Fracture Strain (%) | Yield Stress (MPa) | Fracture Stress (MPa) | Modulus (MPa) |
|---|---|---|---|---|---|---|
| 11 | 4 | 21 | 364 | 23 | 25 | 584 |
| 12 | 8 | 22 | 370 | 26 | 25 | 638 |
| 13 | 15 | 20 | 370 | 35 | 32 | 806 |
| 14 | 4 | 25 | 380 | 24 | 25 | 564 |
| 15 | 8 | 26 | 325 | 25 | 24 | 608 |
| 16 | 15 | 20 | 372 | 32 | 27 | 810 |

Comparison Examples 11–16 illustrate that multilayered barrier films can be made on a blown film coextrusion line, and have properties similar to those produced via flat film coextrusion processing. For example, the modulus values for non-quenched Comparison Examples 12 and 15 are comparable to those of Comparison Examples 9 and 10.

Furthermore, since quenched multilayered barrier structures in accordance with the present invention can be made by flat film coextrusion, as shown in Examples 2–3 and 6, it is reasonable to expect that with appropriate modification to include quenching of the extrudate, that the blown film coextrusion processing disclosed in Comparison Examples 11–16 could also be utilized to form the multilayered barrier structures of the present invention.

EXAMPLES 17, 19, 21, 23, 25 and 27–31, and COMPARISON EXAMPLES 18, 20, 22, 24 AND 26

Fifteen, five-layered, coextruded barrier films were made according to the same procedures as for Examples 1–4 and 6, and Comparison Examples 5 and 7–10 herein. Layer A was made from 50/50 mixtures by weight of polypropylene and polybutylene based resins. The polypropylenes used were Nos. PP3374 (melt index=2.5 g/10 min.) and PP3576 (melt index=9 g/10 min.), (Fina Oil and Chemical Co.). The polybutylenes employed were Nos. PB 8310 (melt index=3 g/10 min.), DP1560 (melt index=4 g/10 min.), PB 300 (melt index=4 g/10 min.), PB 8340 (melt index=4 g/10 min.), and PB 400 (melt index=20 g/10 min.), (Shell Chemical Co.). Numbers PB 8310 and PB 8340 are polybutylene-ethylene copolymers, and No. DP1560 is a polybutylene-based special formulation (Shell Chemical Co.). Layer B was made of Plexar™ 420 (melt index=2.5 g/10 min.) (Quantum Chemical Co.). Layer C was made of EVOH, (EVAL™, E105A) (melt index 5.5 g/10 min.) (Evalca Co.) (Note: Examples 17 and 18 were made using a precompounded mixture of Fina PP3150 (melt index=0.8 g/10 min.), and PB1710A, melt index=1.0 g/10 min.).

The barrier film rolls were extruded onto casting rolls at either temperatures of 10° C. for Examples 17, 19, 21, 23, 25 and 27–31, or 66° C. for Comparison Examples 18, 20, 22, 24, and 26. All films were coextruded at the rate of 10 meters per minute (mpm). Accordingly, for those Comparison Example films cooled at 66° C., the crystalline phase of polypropylene was present, instead of the mesophase of polypropylene found in the Examples quenched at 10° C. The film coextrusion conditions employed for each of Examples and Comparison Examples are given in Table 10.

The tensile properties of the barrier films of the Examples and Comparison Examples were obtained as in Examples 1–4 and 6, and Comparison Examples 5 and 7–10. Yield strain, fracture strain, yield stress, fracture stress and Young's modulus, expressed in (MPa), for Examples 17, 19, 21, 23, 25, and 27–31 and Comparison Examples 18, 20, 22, 24 and 26 are shown in Table 11. At least three samples for each of the Example and Comparison Examples barrier film were measured for each value reported.

TABLE 10

Film coextrusion conditions and compositions employed for each layer of Examples 17, 19, 21, 23, 25 and 27–31, and for Comparison Examples 18, 20, 22, 24 and 26.

| Individual Layer Process Conditions | Ex. 17 | Comp. Ex. 18 | Ex. 19 | Comp. Ex. 20 | Ex. 21 | Comp. Ex. 22 | Ex. 23 |
|---|---|---|---|---|---|---|---|
| Layer A | | | | | | | |
| PP Type | 3150 | 3150 | 3374 | 3374 | 3374 | 3374 | 3374 |
| PB Type | 1710A | 1710A | 8310 | 8310 | 1560 | 1560 | 300 |
| Melt Temp. (°C.) | 223 | 222 | 221 | 222 | 221 | 221 | 221 |
| Screw Speed (RPM) | 26 | 26 | 26 | 26 | 26 | 26 | 26 |
| Layer B | | | | | | | |
| Plexar ™ Type | 420 | 420 | 420 | 420 | 420 | 420 | 420 |
| Melt Temp. (°C.) | 204 | 204 | 204 | 204 | 204 | 204 | 204 |
| Screw Speed (RPM) | 13 | 13 | 14 | 14 | 14 | 14 | 15 |
| Layer C | | | | | | | |
| EVOH Type | E105A | E105A | E105A | E105A | E105A | E105A | E105A |
| Melt Temp. (°C.) | 231 | 231 | 231 | 232 | 232 | 232 | 231 |
| Screw Speed (RPM) | 15 | 15 | 15 | 15 | 15 | 15 | 15 |
| Die Temp. (°C.) | 224 | 224 | 224 | 224 | 232 | 232 | 232 |
| Cast Roll Temp (°C.) | <10 | 66 | <10 | 66 | <10 | 66 | <10 |
| Film Thickness (microns) | 71 | 84 | 61 | 71 | 74 | 64 | 59 |

| Individual Layer Process Conditions | Comp. Ex. 24 | Ex. 25 | Comp. Ex. 26 | Ex. 27 | Ex. 28 | Ex. 29 | Ex. 30 | Ex. 31 |
|---|---|---|---|---|---|---|---|---|
| Layer A | | | | | | | | |
| PP Type | 3374 | 3374 | 3374 | 3576 | 3576 | 3576 | 3576 | 3374 |
| PB Type | 330 | 8340 | 8340 | 8310 | 300 | 8340 | 1560 | 400 |
| Melt Temp. (°C.) | 222 | 222 | 222 | 221 | 231 | 233 | 232 | 232 |
| Screw Speed (RPM) | 26 | 26 | 26 | 26 | 26 | 26 | 26 | 26 |
| Layer B | | | | | | | | |
| Plexar ™ Type | 420 | 420 | 420 | 420 | 420 | 420 | 420 | 420 |
| Melt Temp. (°C.) | 204 | 204 | 204 | 204 | 204 | 204 | 204 | 204 |
| Screw Speed (RPM) | 15 | 15 | 15 | 15 | 15 | 15 | 15 | 15 |

TABLE 10-continued

Film coextrusion conditions and compositions employed for each layer of
Examples 17, 19, 21, 23, 25 and 27–31, and for Comparison Examples 18, 20, 22, 24 and 26.

Layer C

| EVOH Type | E105A | E105A | E105A | E105A | E105A | E105A | E105A | E105A |
|---|---|---|---|---|---|---|---|---|
| Melt Temp. (°C.) | 231 | 231 | 231 | 232 | 231 | 231 | 237 | 242 |
| Screw Speed (RPM) | 14 | 14 | 14 | 14 | 14 | 14 | 14 | 14 |
| Die Temp. (°C.) | 232 | 232 | 232 | 232 | 232 | 232 | 232 | 232 |
| Cast Roll Temp (°C.) | 66 | <10 | 66 | <10 | <10 | <10 | <10 | <10 |
| Film Thickness (microns) | 53 | 66 | 58 | 69 | 64 | 69 | 64 | 48 |

TABLE 11

Yield strain, fracture strain, yield stress,
fracture stress and Young's modulus for
Examples 17, 19, 21, 23, 25 and 27–31 and
Comparison Examples 18, 20, 22, 24, and 26.

| Example | Yield Strain (%) | Fracture Strain (%) | Yield Stress (MPa) | Fracture Stress (MPa) | Modulus (MPa) |
|---|---|---|---|---|---|
| Ex. 17 | 18 | 430 | 16 | 28 | 454 |
| Comp. Ex. 18 | 8 | 447 | 21 | 32 | 572 |
| Ex. 19 | 20 | 426 | 14 | 23 | 380 |
| Comp. Ex. 20 | 21 | 411 | 17 | 25 | 450 |
| Ex. 21 | 16 | 429 | 16 | 24 | 492 |
| Comp. Ex. 22 | 18 | 406 | 23 | 28 | 620 |
| Ex. 23 | 17 | 418 | 15 | 25 | 446 |
| Comp. Ex. 24 | 23 | 345 | 20 | 26 | 496 |
| Ex. 25 | 18 | 462 | 15 | 27 | 426 |
| Comp. Ex. 26 | 22 | 387 | 23 | 32 | 572 |
| Ex. 27 | 17 | 473 | 14 | 25 | 416 |
| Ex. 28 | 15 | 427 | 17 | 24 | 468 |
| Ex. 29 | 17 | 420 | 16 | 24 | 454 |
| Ex. 30 | 15 | 468 | 17 | 26 | 508 |
| Ex. 31 | 14 | 470 | 15 | 25 | 444 |

The Example and Comparison Example films illustrate that multilayered barrier films can be made with outer layers comprised of blends of polypropylene of varying melt index combined with various polybutylene and polybutylene copolymers. The mechanical property data of Table 11 shows that those quenched multilayered barrier films made in accordance with the principles of the present invention (i.e., Example Nos. 17, 19, 21, 23, 25, and 27–31) have modulus values 10–26% less than their corresponding non-quenched films (i.e., Comparison Example Nos. 18, 20, 22, 24, and 26), and accordingly, are softer (less stiff) than the non-quenched films.

EXAMPLES 32–41

Ten, five-layered, coextruded barrier films were made using a flat film process consisting of three extruders as described in Examples 1–4 and 6. Layer A was made from mixtures of polypropylene (No. PP3576, melt index=9 g/10 min.; or No. PP3374, melt index=2.5 g/10 min.; Fina Oil and Chemical Co.) and polybutylene (No. PB400, melt index=20 g/10 min.; or No. PB8340, melt index=4 g/10 min., Shell Chemical Co.). Layer B was of Plexar™420 (melt index=2.5 g/10 min.; Quantum Chemical Co.) or Admer™ QF551A (melt index=5.7 g/10 min.; Mitsui Plastics, Inc.). Layer C was an EVOH copolymer (No. E105, melt index=5.5 g/10 min; or No. G115, melt index=14 g/10 min., or No. ES-G110, melt index=16, g/10 min.; Evalca Co.). The process conditions for each layer of Examples 32–41 are shown in Table 12. The films were all made at 12 meters per minute (mpm), and were quenched on a 14° C. casting roll to a 75µ thickness. The specific compositions of each film of Examples 32–41 are given in Table 13.

TABLE 12

Process conditions for each layer
of Example films 32–41

| Layer | Melt Temperature (°C.) | Screw Speed (RPM) |
|---|---|---|
| A | 227 | 59 |
| B | 227 | 14 |
| C | 231 | 10 |

TABLE 13

Compositions of each film of Examples 32–41
(all Example films were quenched at a
temperature of 14° C.).

| Example | Layer A PP | Layer B PB | PP:PB | Layer B Adhesive | Layer C EVOH |
|---|---|---|---|---|---|
| 32 | 3576 | 400 | 80/20 | PLEXAR ™ 420 | E105 |
| 33 | 3576 | 400 | 80/20 | PLEXAR ™ 420 | G115 |
| 34 | 3576 | 400 | 50/50 | PLEXAR ™ 420 | G115 |
| 35 | 3576 | 400 | 50/50 | PLEXAR ™ 420 | E105 |
| 36 | 3374 | 400 | 50/50 | PLEXAR ™ 420 | E105 |
| 37 | 3374 | 400 | 50/50 | PLEXAR ™ 420 | G115 |
| 38 | 3576 | 8349 | 20/80 | PLEXAR ™ 420 | G115 |
| 39 | 3576 | 8340 | 20/80 | PLEXAR ™ 420 | 3105 |
| 40 | 3374 | 8340 | 50/50 | ADMER ™ QF551A | E105 |
| 41 | 3374 | 8340 | 50/50 | ADMER ™ QF551A | ES-G110 |

The tensile properties of each of the Example barrier films were obtained as in Example and Comparison Example Numbers 11–31. Yield strain, fracture strain, yield stress, fracture stress and Young's modulus are shown for Examples 32–41 in Table 14. At least three samples for each of the Example barrier films were measured for each value reported.

TABLE 14

Yield strain, fracture strain, yield stress, fracture stress and modulus for Examples 32–41.

| Example | Yield Strain (%) | Fracture Strain (%) | Yield Stress (MPa) | Fracture Stress (MPa) | Modulus (MPa) |
|---|---|---|---|---|---|
| 32 | 16 | 634 | 18 | 34 | 532 |
| 33 | 16 | 831 | 17 | 37 | 476 |
| 34 | 17 | 755 | 14 | 33 | 360 |
| 35 | 17 | 618 | 13 | 30 | 384 |
| 36 | 19 | 665 | 15 | 39 | 412 |
| 37 | 20 | 703 | 14 | 37 | 354 |
| 38 | 20 | 605 | 12 | 37 | 268 |
| 39 | 20 | 455 | 12 | 31 | 282 |
| 40 | 20 | 704 | 14 | 41 | 352 |
| 41 | 19 | 631 | 14 | 14 | 354 |

Examples 32–41 illustrate that multilayered barrier films can be made with outer layers comprised of blends of varying ratio, of polypropylene with differing melt index in combination with polybutylene and polybutylene copolymers, and with a core layer of EVOH copolymers which have varying mole percents of ethylene in the copolymers (44% for E105, 48% for G115, and 53% for ES-G110). Examples 32–35 also show that modulus, and accordingly the softness of the barrier films, can be effectively controlled by changing the mesomorphous polypropylene (mPP) ratio in the blend. Specifically, as the percent mPP is decreased from 80% in Examples 32–33 to 50% in Examples 34–35, a corresponding drop in the modulus of 25–28% is observed.

EXAMPLES 42–43

Two, three-layered, coextruded barrier films analogous to the film constructions illustrated in FIG. 1 were made using a flat film process by blending polypropylene (No. PP3374, melt index 2.5 g/10 min.; Fina Oil and Chemical Co.) and polybutylene (No. PB8340; melt index 4.0 g/10 min.; Shell Chemical Co.) as layer A, blending EVOH (No. E105; melt index 5.5 g/10 min.; Evalca Co.) and ethylene vinyl acetate copolymer (EVA) (Elvax 660; Dupont, Inc.) for layer C, and eliminating adhesive layer B. The films were made at 12 meters per minute, and were quenched on a 14° C. casting roll to a 75μ thickness. The process conditions for each layer of Examples 42 and 43 are shown in Table 15. The specific compositions of each of the Example films are given in Table 16.

TABLE 15

Process conditions for each layer of Examples 42 and 43.

| Layer | Melt Temperature (°C.) | Screw Speed (RPM) |
|---|---|---|
| A | 227 | 59 |
| C | 231 | 10 |

TABLE 16

Compositions of Examples 42 and 43 films. (All Example films were quenched at a temperature of 14° C.)

| Example | Layer A PP | Layer A PP:PB | Layer C EVOH:EVA | Layer C EVOH:EVA |
|---|---|---|---|---|
| 42 | 3374 | 50/50 | E105/EVA660 | 49:1 |
| 43 | 3374 | 50/50 | E105/EVA660 | 19:1 |

The tensile properties for each of the Example barrier films were obtained as in Examples 1–4 and 6. Yield strain, fracture strain, yield stress, fracture stress and Young's modulus for Examples 42–43 are given in Table 17. At least three samples for each Example barrier film were measured for each value reported.

TABLE 17

Yield strain, fracture strain, yield stress, fracture stress and Young's modulus for Examples 42–43.

| Example | Yield Strain (%) | Fracture Strain (%) | Yield Stress (MPa) | Fracture Stress (MPa) | Modulus (MPa) |
|---|---|---|---|---|---|
| 42 | 21 | 617 | 14 | 39 | 346 |
| 43 | 20 | 619 | 14 | 35 | 308 |

Examples 42 and 43 illustrate that three-layer multilayered barrier films in accordance with the present invention can be formed by blending EVA copolymer along with EVOH in the gas barrier layer of the present invention. When such a gas barrier layer is coextruded along with the mesopolymer blends employed in the moisture barrier layer (s), a multilayered barrier film in accordance with the present invention can be formed without the need to resort to optional adhesive layers.

EXAMPLE 44 AND COMPARISON EXAMPLE 45

Multilayered barrier films of sixty-five (65) layers were made on a multilayer coextrusion line utilizing three extruders. The 65-layered construction consisted of opposing, outer moisture barrier layers (hereinafter layer "A"), each of which was followed by an adhesive layer (hereinafter layer "B"), and then a gas barrier layer (hereinafter layer "C"). Thereafter, the structure alternated layers as follows: layer B, layer A, layer B, layer C, layer B, layer A, layer B, layer C, etc. Layer A comprised polypropylene No. PP3014 (melt index=12 g/10 min.); Exxon, Inc.). Layer B comprised Admer™ QF 551A (melt index=5.7 g/10 min.; Mitsui Plastics, Inc.). While, layer C comprised an EVOH copolymer, No. EVAL F101 (melt index=1.6 g/10 min.; Evalca Co.).

The Example and Comparison Example barrier films were cast on a temperature-controlled casting roll at a temperature of 81° C. for Comparison Example 45, and 5° C. for Example 44. Wide-angle X-ray diffraction (WAXD) measurements of each of the films showed that the Comparison Example 45 film contained undesirable crystalline polypropylene of the isotactic I structure, while the quenched film of Example 44 was of mesomorphous polypropylene structure. The films were irradiated using electron-beam ionizing radiation and stored at room temperature for prolonged periods of time. The mechanical properties, including elongation to break, for the aging Example and Comparison films, were measured utilizing an Instron™ Model 1122 machine according to ASTM D882-31, with a strain rate of 100% per minute. Table 18 contains the percent elongation to break data for irradiated films of Example 44 and Comparison Example 45 over time.

TABLE 18

Percent elongation to break data for irradiated films of Example 44 and Comparison Example 45.
(Mon. = month; Q = quenched; NQ = non-quenched)

| Example Number | E-Beam Dosage (kGy) | % Elong. to Break | | | | | Percent Retention (3 Mons.) |
|---|---|---|---|---|---|---|---|
| | | Zero Week | One Week | One Mon. | Two Mon. | Three Mon. | |
| Ex. 44 (Q) | 0 | 393 | 393 | — | 386 | 380 | 97% |
| | 50 | 393 | 321 | 338 | 302 | 340 | 87% |
| | 100 | 393 | 317 | 338 | 392 | 293 | 75% |
| Comp. Ex. 45 (NQ) | 0 | 302 | 302 | — | 363 | 350 | 116% |
| | 50 | 302 | 268 | 204 | 68 | 46 | 15% |
| | 100 | 302 | 178 | 150 | 22 | 17 | 6% |

As the results in Table 18 illustrate, the quenched multilayered barrier film of Example 44, which contained mesomorphous polypropylene, retained excellent mechanical properties (i.e., percent elongation to break), even at three months after irradiation at 100 kGy (10 Mrad) dosages. In contrast, the non-quenched, crystalline polypropylene containing film of Comparison Example 45 is non-functional three months after irradiation.

EXAMPLES 46–50, AND COMPARISON EXAMPLES 51–55

Multilayer barrier films corresponding in construction to Examples 1–4 and 6, and Comparative Examples 5, and 7–10 (Example films 1–4 and 6 were used for Examples 46–50; Comparison Example films 5 and 7–10 were used for Comparison Example 51–55) were electron beam irradiated at a dosage of 50 kGy (5 Mrads) and then immediately placed in liquid nitrogen. Electron paramagnetic resonance (EPR) analysis was performed by first warming the films to room temperature, cutting them to 1.3 cm×7.6 cm in size, weighing, and then mounting the film strips in tubes. This technique allows reproducible sample positioning in the EPR cavity. Radical peak heights were recorded for each sample as a function of elapsed time from the initial measurement using a Varian™ model 4502 spectrometer with a 23 cm magnet operating in the "X"-band. Fremy's salt was used as the magnetic field reference. Peak height represents radical concentration as measured in spins/gram. Initial runs were used to estimate radical concentration, and the declining numbers are proportional to the initial number. Since different instrument settings were used for some samples, all numbers were normalized. Spin concentration was calibrated against the National Bureau of Standards No. 261 Ruby Standard.

Figure 18:
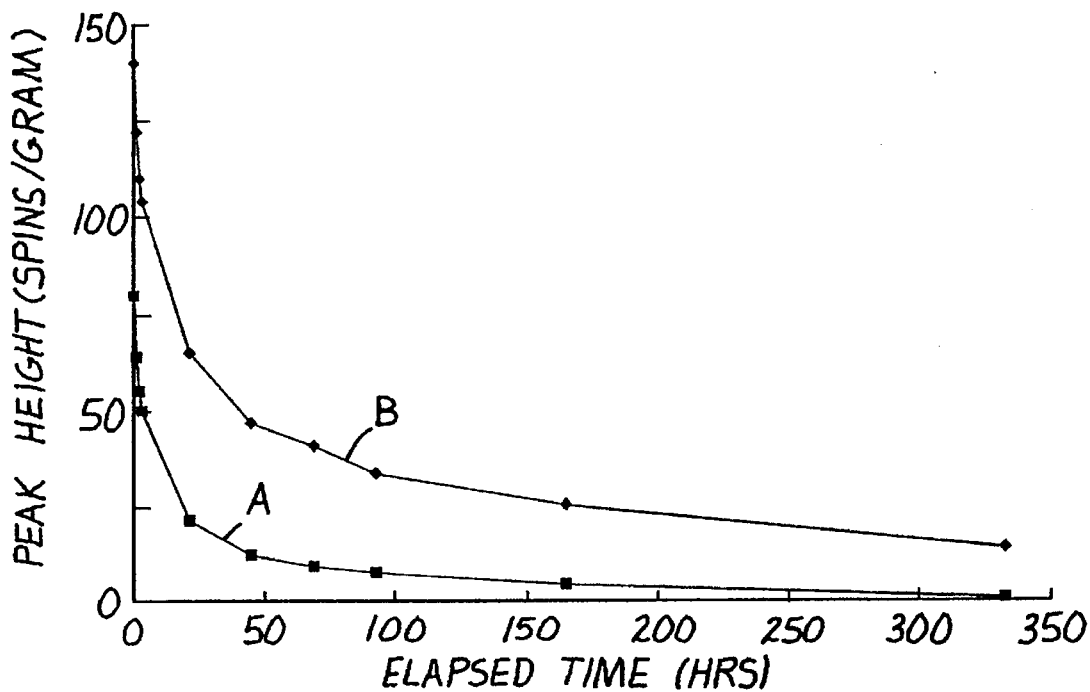
FIG. 18 is a graph comparing the radical decay as measured in normalized radical peak height in spins/gram as a function of elapsed time in hours for the multilayer barrier structures of Example 46 (line A) and Comparison Example 52 (line B) after exposure to a 50 kGy dosage of electron beam radiation.
Figure 19:
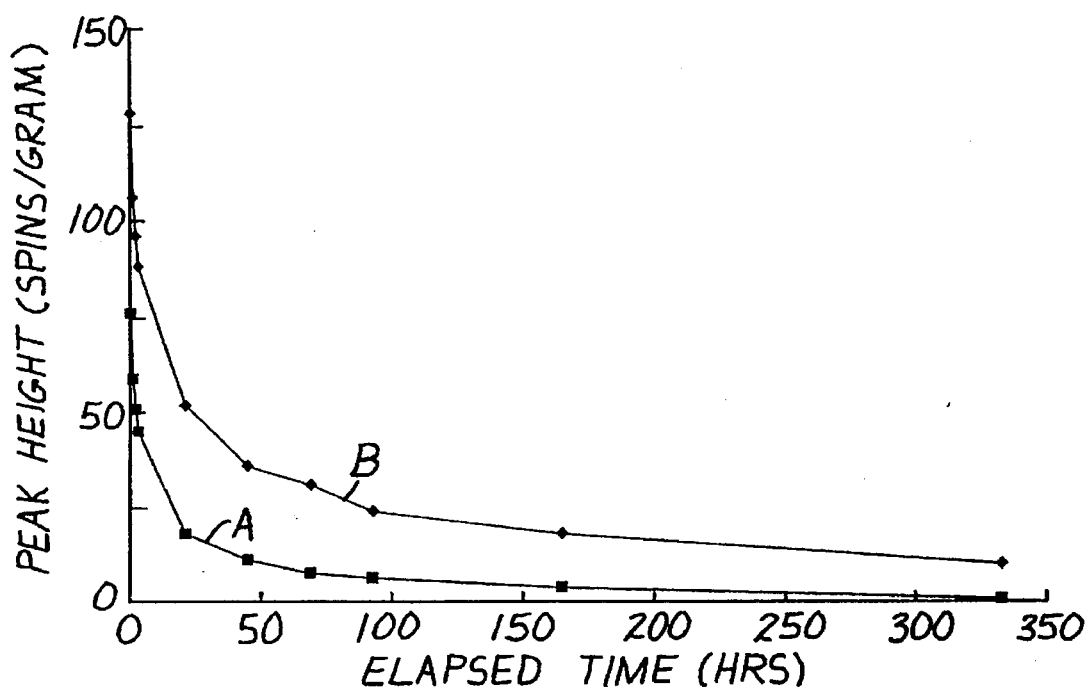
FIG. 19 is a graph comparing the radical decay as measured in normalized radical peak height in spins/gram as a function of elapsed time in hours for the multilayered barriers structures of Example 47 (line A) and Comparison Example 53 (line B) after exposure to a 50 kGy dosage of electron beam radiation.
Figure 20:
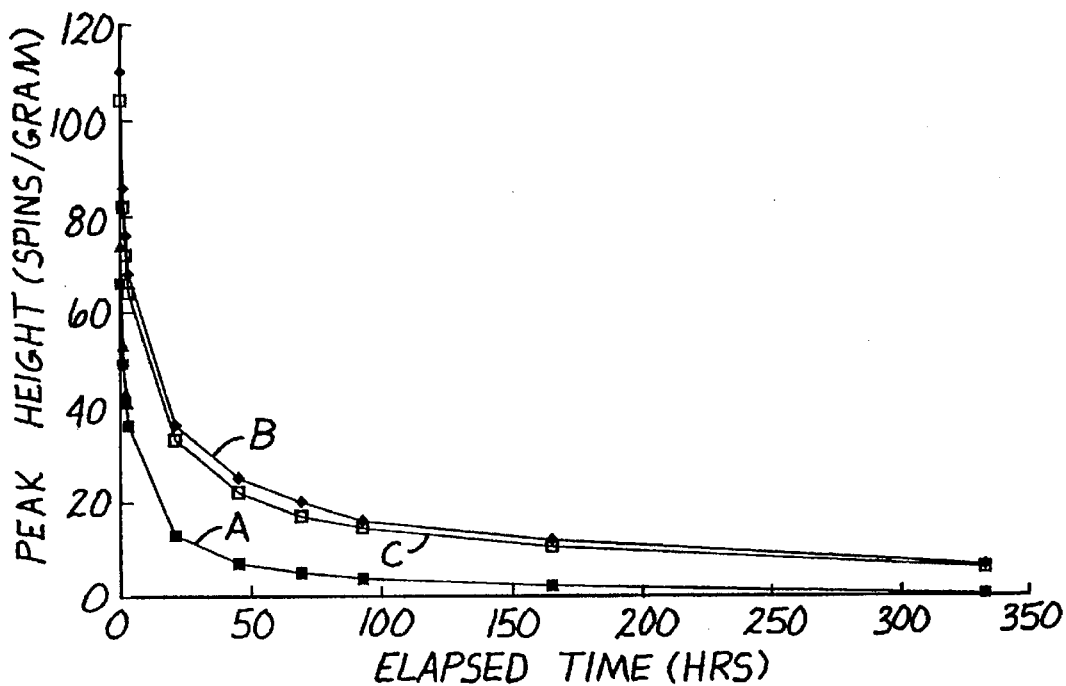
FIG. 20 is a graph comparing the radical decay as measured in normalized radical peak height in spins/gram as a function of elapsed time in hours for the multilayered barrier structures of Examples 48 and 50 (line A) and Comparison Examples 54 (line B) and 55 (line C) after exposure to a 50 kGy dosage of electron beam radiation.
Figure 21:
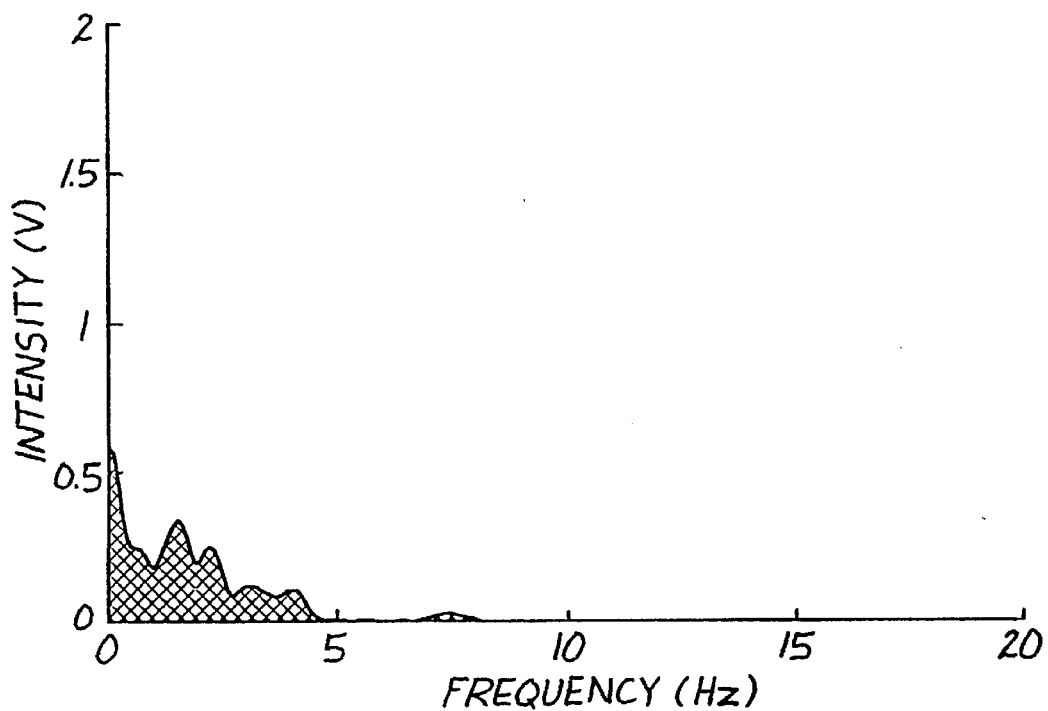
FIG. 21 is a graph of the noise spectra intensity (V) versus frequency (Hz) of the multilayered barrier structure of Example 1.
Figure 22:
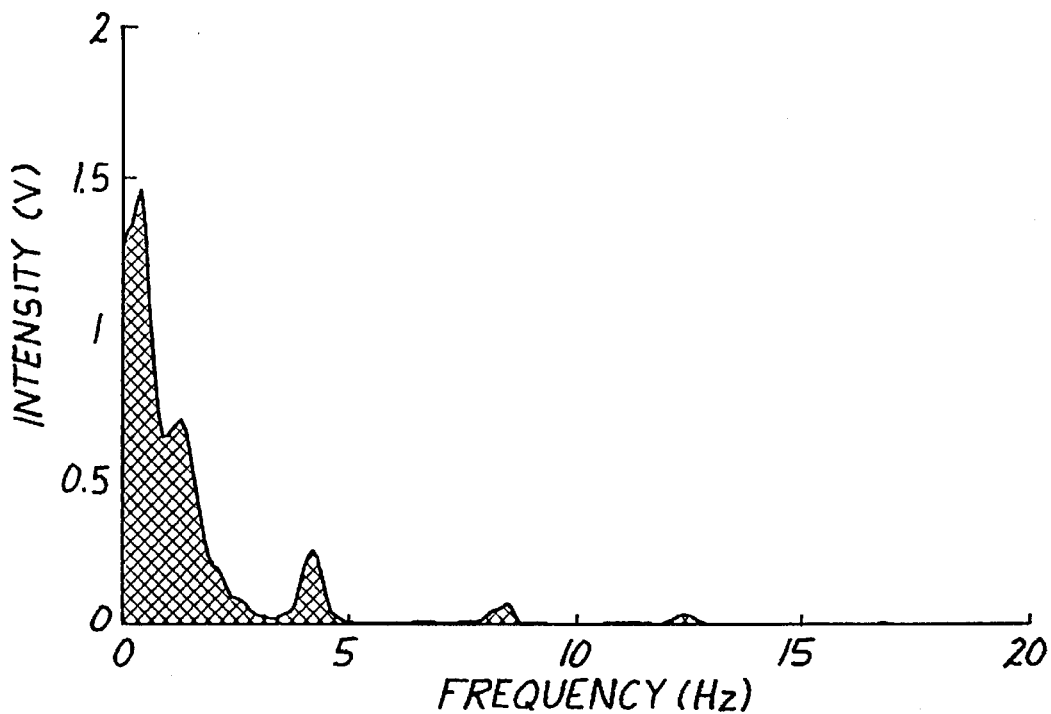
FIG. 22 is a graph of the noise spectra intensity (V) versus frequency (Hz) of the multilayered barrier structure of Comparison Example 7.
Figure 23:
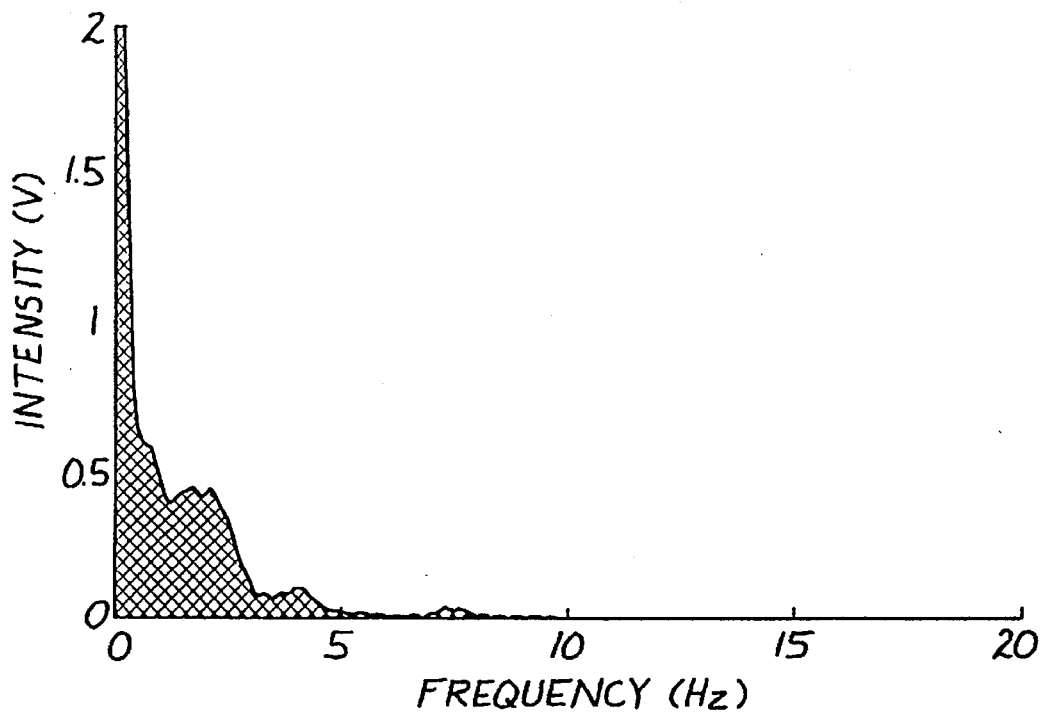
FIG. 23 is a graph of the noise spectra intensity (V) versus frequency (Hz) of the multilayered barrier structure of Example 2.
Figure 24:
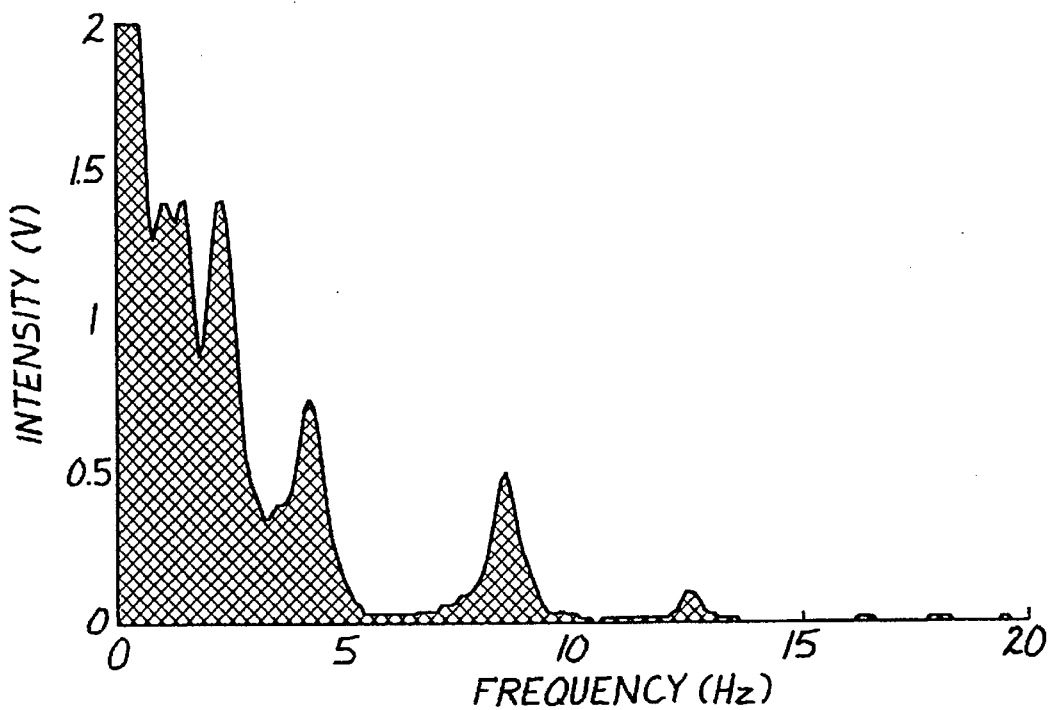
FIG. 24 is a graph of the noise spectra intensity (V) Versus frequency (Hz) of the multilayered barrier structure of Comparison Example 8.
Figure 25:
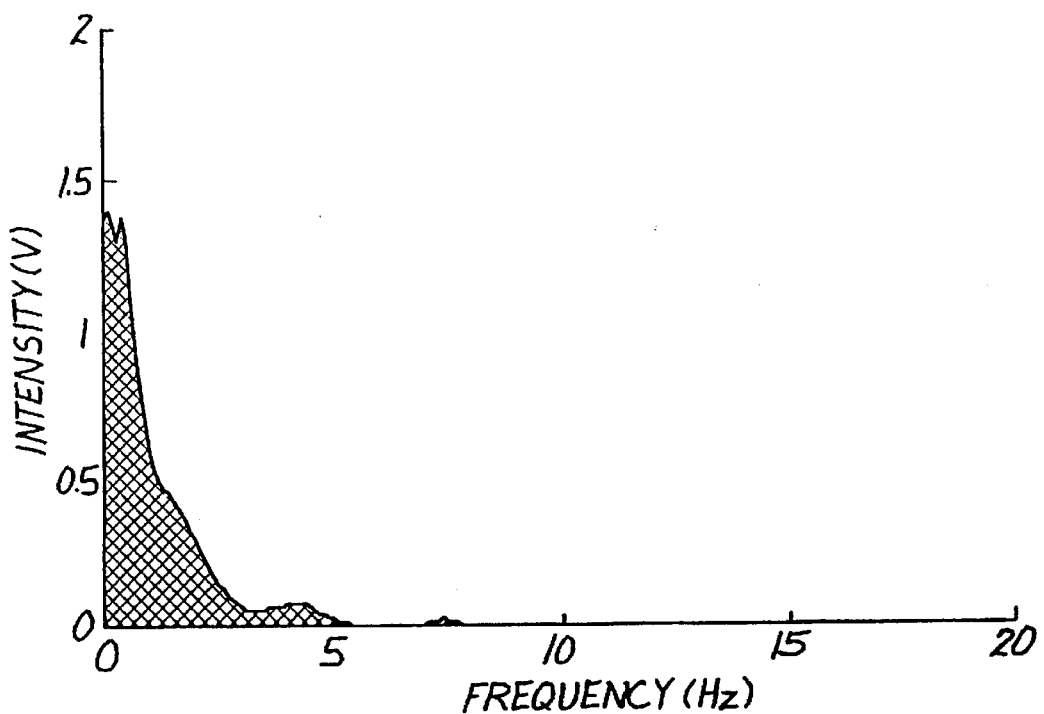
FIG. 25 is a graph of the noise spectra intensity (V) versus frequency (Hz) of the multilayered barrier structure of Example 6.
Figure 26:
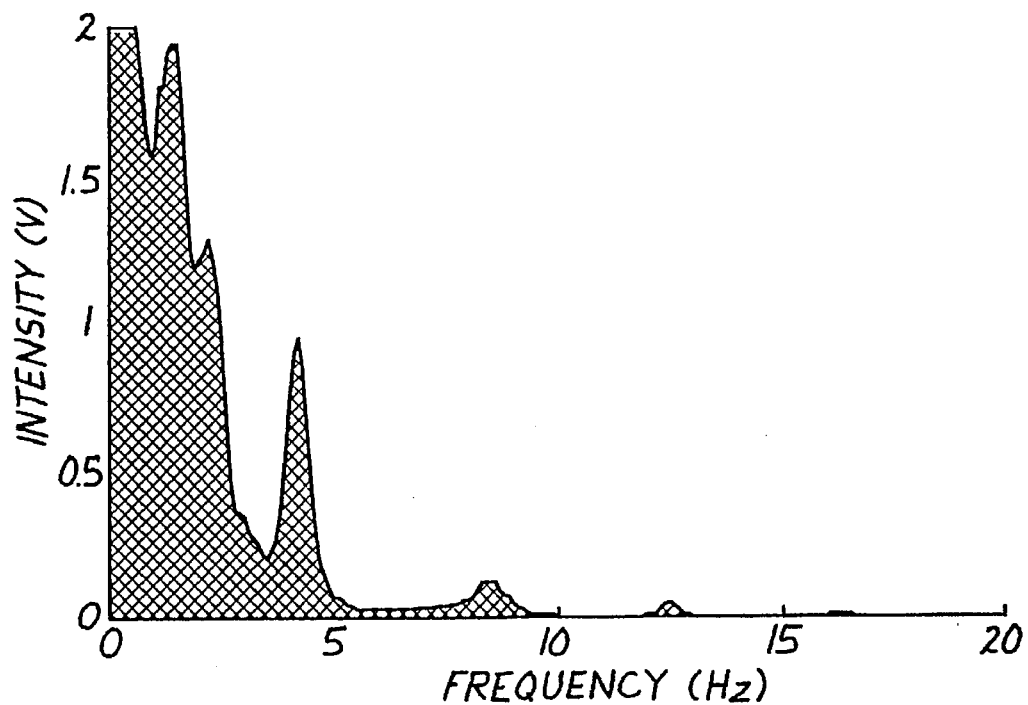
FIG. 26 is a graph of the noise spectra intensity (V) versus frequency (Hz) of the multilayered barrier structure of Comparison Example 9.
Figure 27:
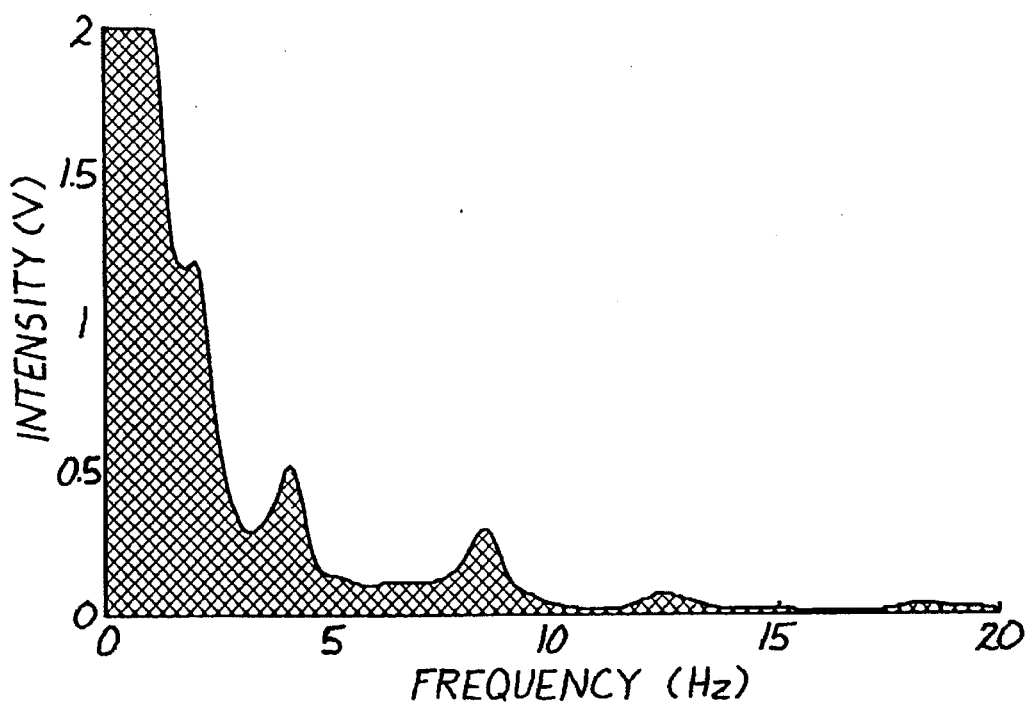
FIG. 27 is a graph of the noise spectra intensity (V) versus frequency (Hz) of the multilayered barrier structure of Example 57.
Figure 28:
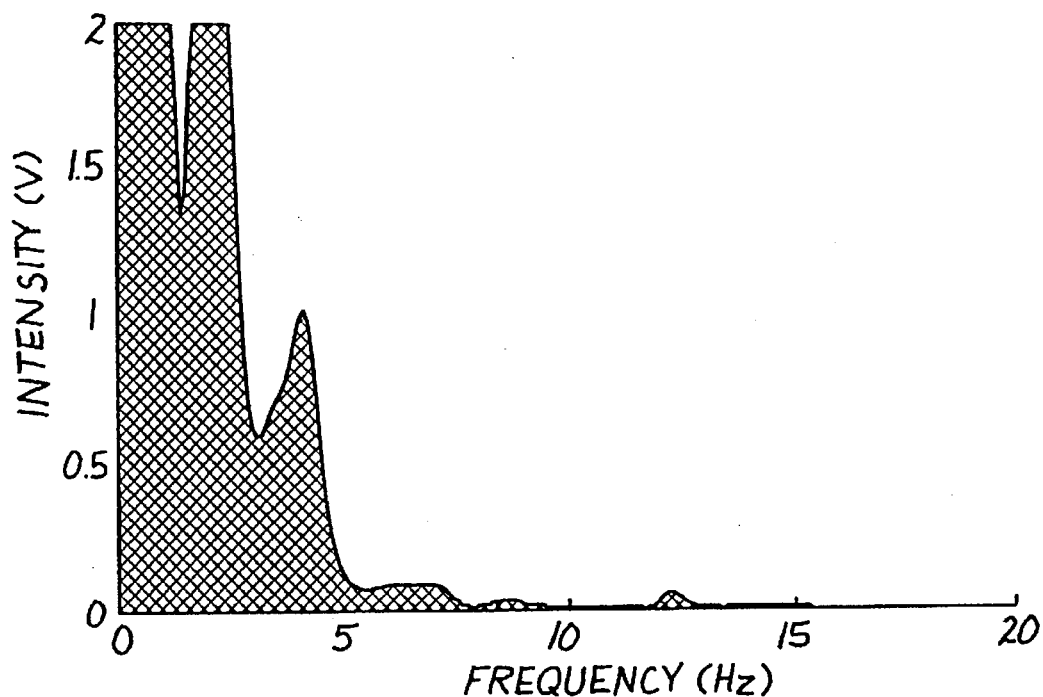
FIG. 28 is a graph of the noise spectra intensity (V) versus frequency (Hz) of the multilayered barrier structure of Comparison Example 73.
Figure 29:
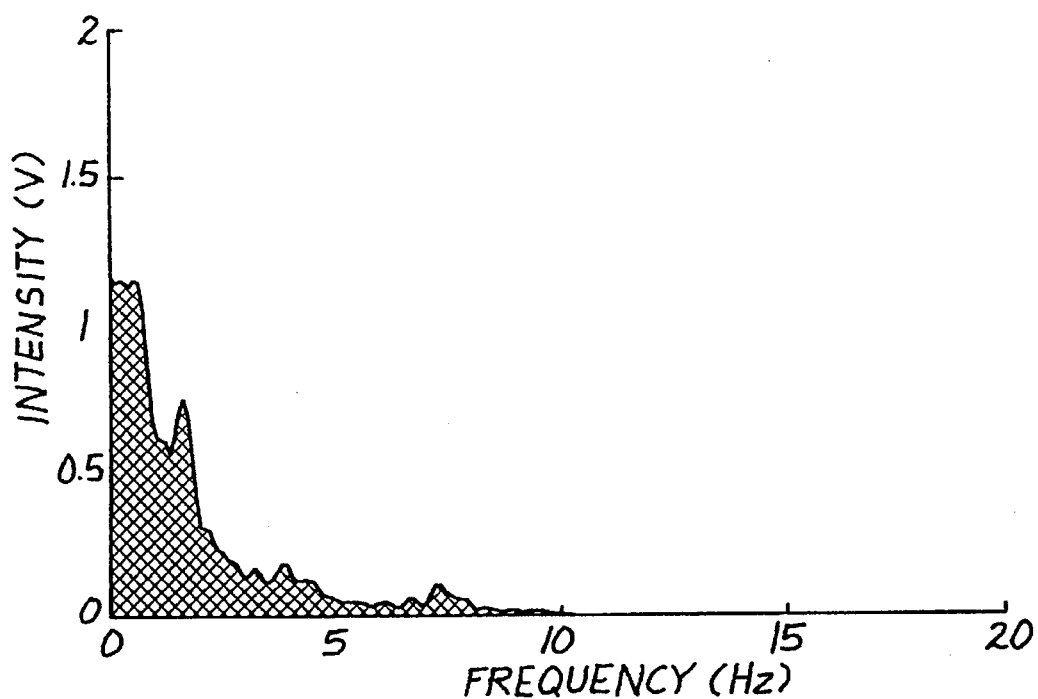
FIG. 29 is a graph of the noise spectra intensity (V) versus frequency (Hz) of the multilayered barrier structure of Example 63.
Figure 30:
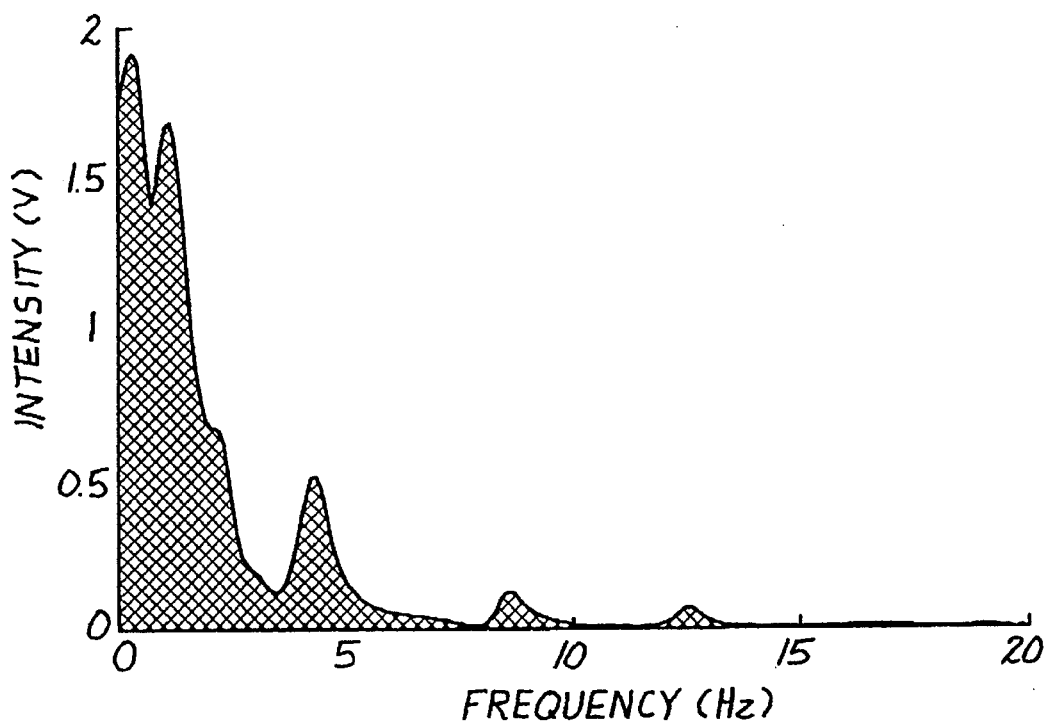
FIG. 30 is a graph of the noise spectra intensity (V) versus frequency (Hz) of the multilayered barrier structure of Comparison Example 78.
Figure 31:
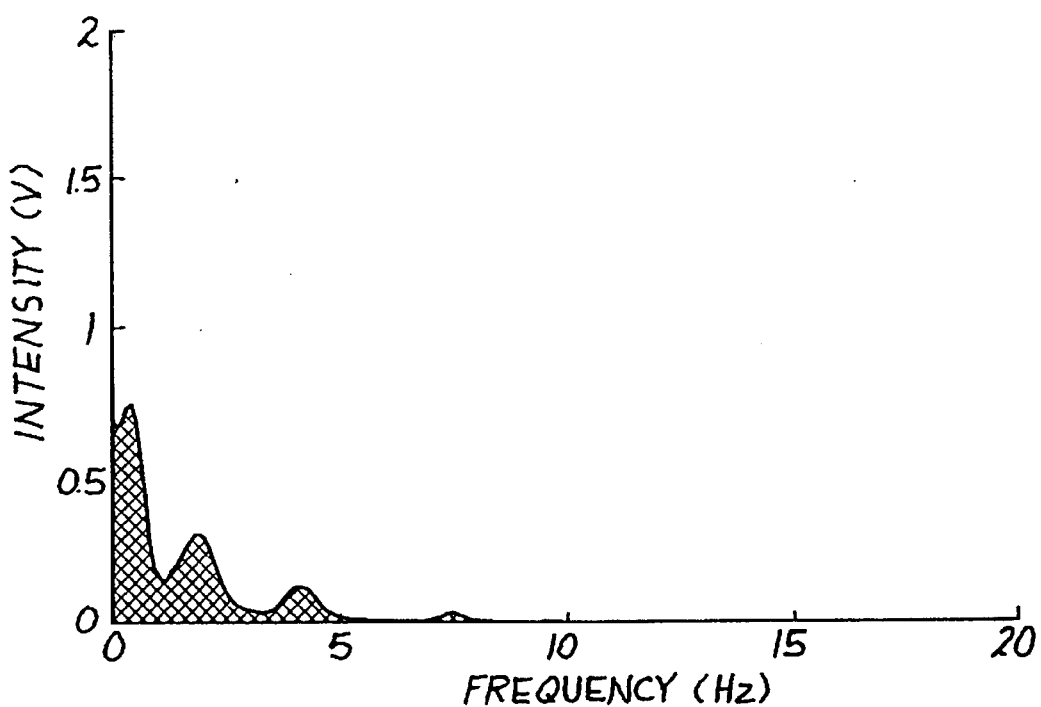
FIG. 31 is a graph of the noise spectra intensity (V) versus frequency (Hz) of the multilayered barrier structure of Example 64.
Figure 32:
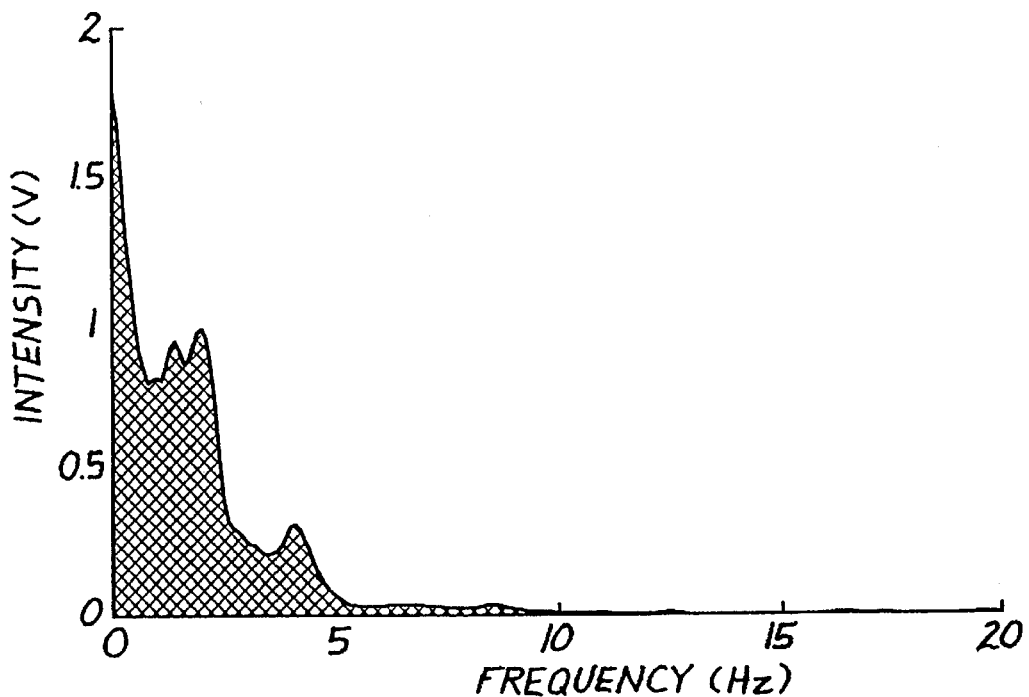
FIG. 32 is a graph of the noise spectra intensity (V) versus frequency (Hz) of the multilayered barrier structure of Example 79.
Figure 33:
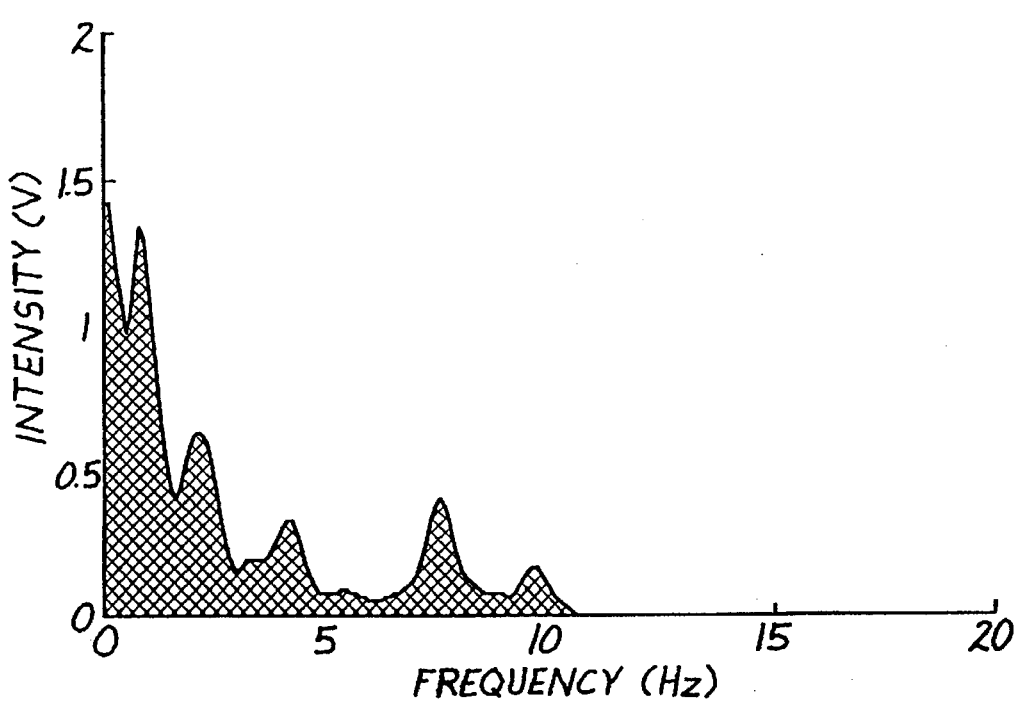
FIG. 33 is a graph of the noise spectra intensity (V) versus frequency (Hz) of the multilayered barrier structure of Example 66.
Figure 34:
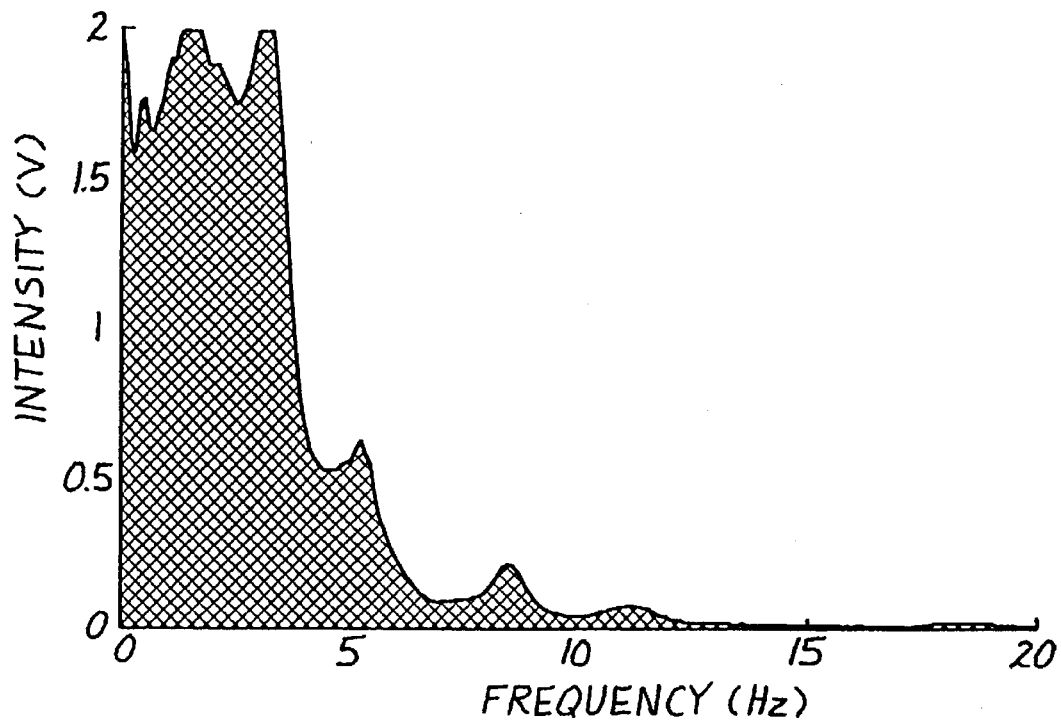
FIG. 34 is a graph of the noise spectra intensity (V) versus frequency (Hz) of the multilayered barrier structure of Comparison Example 81.
Figure 35:
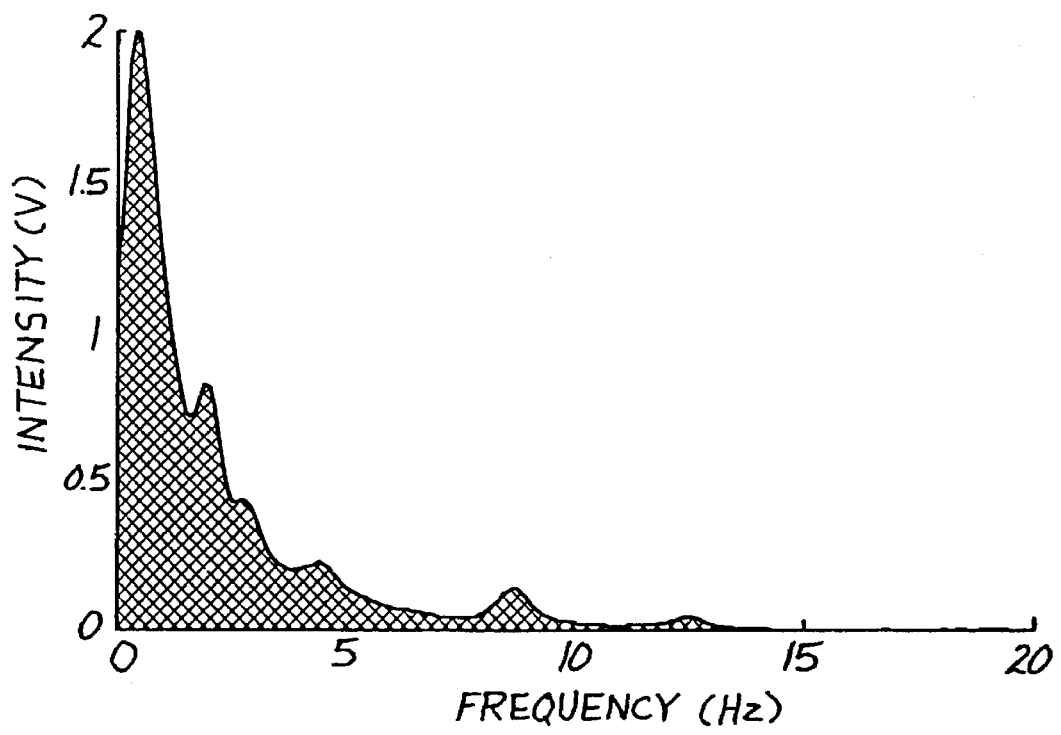
FIG. 35 is a graph of the noise spectra intensity (V) versus frequency (Hz) of the multilayered barrier structure of Example 69.
Figure 36:
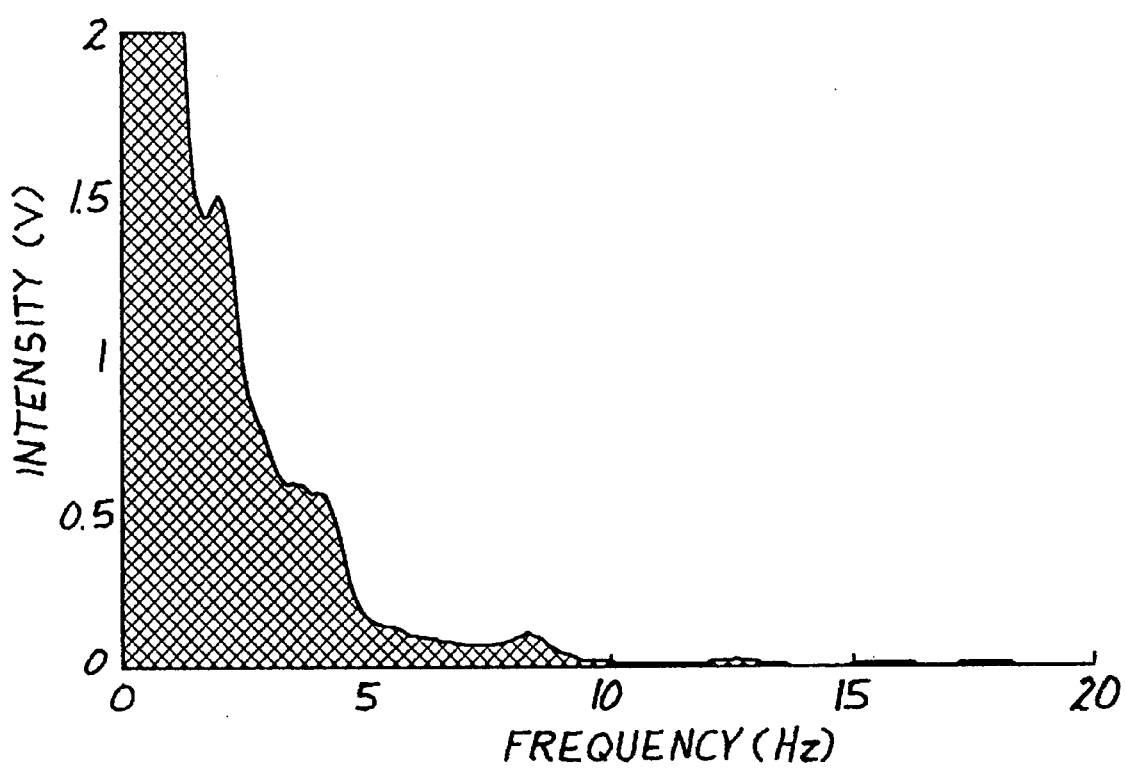
FIG. 36 is a graph of the noise spectra intensity (V) versus frequency (Hz) of the multilayered barrier structure of Comparison Example 84.

Normalized radical peak height in spins/gram is shown in Table 19 as a function of elapsed time (hours) for Examples 46–50 and Comparison Example 51–55. In all cases, radial decay occurs in the quenched films (Examples 46–50) at a much faster rate than in the comparison non-quenched films (Comparison Example 51–55). This is more clearly demonstrated in FIGS. 18–20 where normalized radical peak height is plotted against elapsed time. For example, as FIG. 18 illustrates, radical decay occurs at consistently faster rate for the quenched film of Example 46 (line A) in comparison to the non-quenched film of Comparison Example 52 (line B). Likewise, analogous results are shown with the quenched film of Example 47 (line A) and Comparison Example 53 (line B) in FIG. 19. Furthermore, excellent reproducibility of the data is demonstrated in FIG. 20 where values for quenched film Examples 48 and 50 (line A) fall on the same general curve as for the non-quenched films of Comparison Examples 54 (line B) and 55 (line C). Thus, the quenched films containing mesomorphous polypropylene are expected to maintain their integrity and properties to a greater extent than their non-quenched counterparts since the radicals available for degradation are reduced more rapidly in the quenched films than in the non-quenched films.

TABLE 19

Normalized radical peak height in spins for grams as a function of elapsed time in hours after exposure of the multilayer barrier films of Examples 46–50 and Comparison Examples 51–55 to electron beam radiation.

| Elapsed Time (Hrs.) | Example No. 46 | Example No. 47 | Example No. 48 | Example No. 49 | Example No. 50 | Comp. Example No. 51 | Comp. Example No. 52 | Comp. Example No. 53 | Comp. Example No. 54 | Comp. Example No. 55 |
|---|---|---|---|---|---|---|---|---|---|---|
| 0 | 79 | 76 | 66 | 98 | 74 | 122 | 140 | 128 | 110 | 104 |
| 1 | 63 | 59 | 49 | 73 | 53 | 88 | 122 | 106 | 86 | 82 |
| 2 | 54 | 51 | 41 | 58 | 43 | 70 | 110 | 96 | 76 | 72 |
| 3 | 49 | 45 | 36 | 48 | 36 | 58 | 104 | 88 | 68 | 64 |
| 21 | 21 | 18 | 13 | 14 | 13 | 17 | 64 | 52 | 36 | 33 |
| 45 | 12 | 11 | 7 | 6.3 | 7 | 7 | 46 | 36 | 25 | 22 |
| 69 | 9 | 8 | 5 | 4 | 5 | 4 | 40 | 31 | 20 | 17 |
| 93 | 8 | 6 | 4 | 3 | 4 | 1 | 33 | 24 | 16 | 15 |
| 165 | 4 | 4 | 2 | 1 | 2 | 2 | 25 | 18 | 12 | 11 |
| 333 | 0.9 | 0.8 | 0.4 | 0.3 | 0.4 | 0.4 | 14 | 10 | 7 | 6 |

EXAMPLES 56–71 AND COMPARISON EXAMPLES 72–84

Sixteen, five-layered coextruded barrier films were made using a flat film process as described in Examples 1–4 and 6 and, thirteen, five-layered coextruded barrier films were made as described for Comparison Examples 5 and 7–10. The barrier films were generally coextruded at a film thickness of about 75 μ, with each moisture barrier layer (hereinafter layer "A") being about 31μ thick, each adhesive layer (hereinafter layer "B") being about 4μ thick, and the gas barrier layer (hereinafter layer "C") being about 8μ thick. The construction of the five-layer barrier films of Examples 56–71 and Comparison Examples 72–84 corresponded to the multilayered constructions illustrated in FIG. 2 herein.

Layer A comprised mixtures by weight of polypropylene resin (PP) (PP3576; melt index=9 g/10 min; Fina Oil and Chemical Co.) with ethylene vinyl acetate copolymer resin (EVA) (No. UE656; melt index=5.4 g/10 min.; 12% vinyl acetate content; Quantum Chemical Corp.), or with ethylene acrylic acid copolymer resin (EAA) (Primacor 3340; melt index=9 g/10 min.; 6.5% acrylic acid comonomer content; Dow Chemical Co.), or with both polybutylene resin (PB) (PB400; melt index=20 g/10 min.; Shell Chemical Co.) and EVA, or with both PB and EAA. Layer B comprised a polypropylene based adhesive layer of Admer™ QF551A resin (melt index=5.7 g/10 min.); Mitsui Plastics, Inc.). Layer C was made of an ethylene vinyl alcohol copolymer (EVOH)(E105A, melt index=5.5 g/10 min.; Evalca Co.).

The blended mixtures were dry blended before being melted and coextruded. The films for Examples 56–71 and Comparison Examples 72–84 were extruded at a melt temperature of 221° C. for layer A, and 232° C. for layers B and C. Table 20 lists specific constructions for Examples 56–71 and Comparison Examples 72–84. Temperature for the quench roll for Examples 56–71 was maintained at 10° C. in order to control the mesomorphous structure of the polypropylene in the mesopolymer blend, while a quench temperature of 66° C. was utilized with Comparison Examples 72–84, thereby resulting in crystalline polypropylene being present in the polymer blends. Adhesive and gas barrier layer constructions were kept constant across all the Examples and Comparison Examples.

TABLE 20

Film constructions and Young's Modulus values (MPa) for Examples 56–71 and Comparison Examples 72–84.

| Ex. No./ Comp. Ex. No. | Composition | Blend Ratio (Wt %) | Quench Temp. (°C.) | Young's Modulus Ex./Comp. Ex. |
|---|---|---|---|---|
| 56/72 | mPP:EVA | 100/0 | 10/66 | 772/994 |
| 57/73 | mPP:EVA | 75/25 | 10/66 | 674/810 |
| 58/74 | mPP:EVA | 50/50 | 10/66 | 536/608 |
| 59/75 | mPP:EVA | 25/75 | 10/66 | 378/508 |
| 60/— | mPP:EVA | 0/100 | 10/66 | 356/— |
| 61/76 | mPP:PB:EVA | 50/50/0 | 10/66 | 482/618 |
| 62/77 | mPP:PB:EVA | 37.5/37.5/25 | 10/66 | 460/526 |
| 63/78 | mPP:PB:EVA | 25/25/50 | 10/66 | 346/454 |
| 64/79 | mPP:PB:EVA | 12.5/12.5/75 | 10/66 | 316/410 |
| 65/80 | mPP:EAA | 75/25 | 10/66 | 662/828 |
| 66/81 | mPP:EAA | 50/50 | 10/66 | 578/694 |
| 67/82 | mPP:EAA | 25/75 | 10/66 | 462/548 |
| 68/— | mPP:EAA | 0/100 | 10/66 | 352/— |
| 69/83 | mPP:PB:EAA | 37.5/37.5/25 | 10/66 | 480/582 |
| 70/84 | mPP:PB:EAA | 25/25/50 | 10/66 | 456/488 |
| 71/— | mPP:PB:EAA | 12.5/12.5/75 | 10/66 | 384/— |

Tensile properties were performed on an Instron™ model 1122 machine according to the same procedures as disclosed in Examples 1–4 and 6, and Comparison Examples 5 and 7–10 herein. In each case, at least three samples of each Example and Comparison Example were measured for each value reported.

Figure 15:
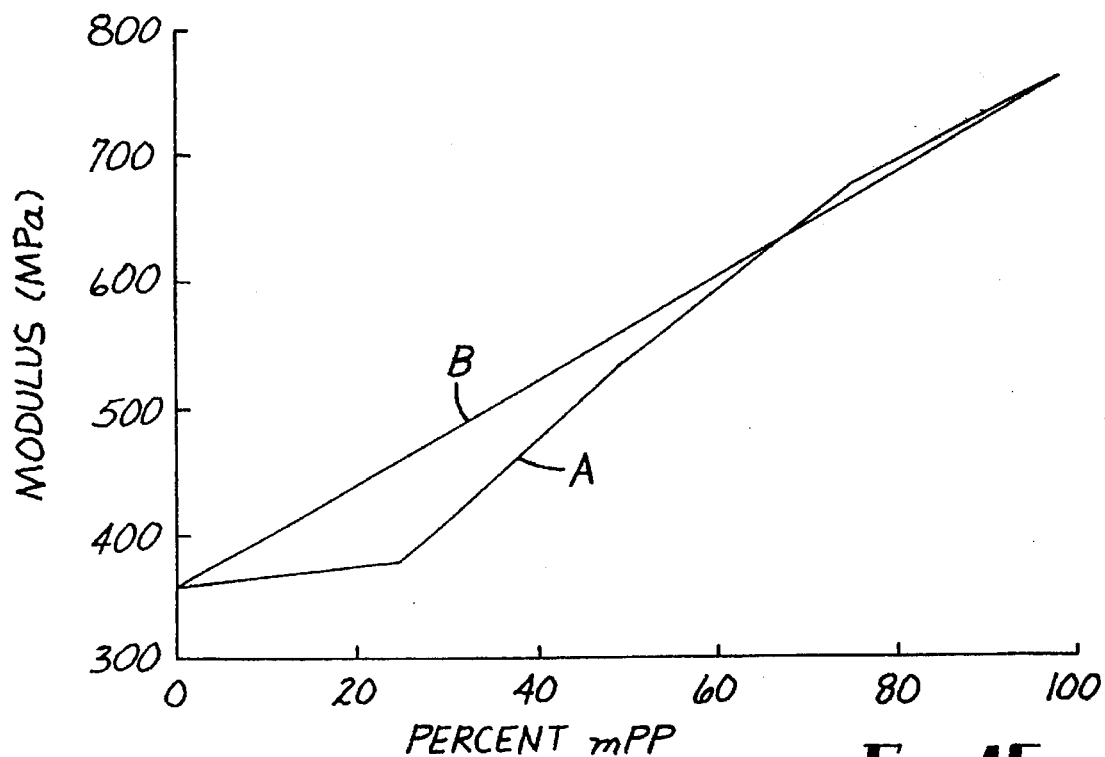
FIG. 15 is a graph comparing Young's modulus of the multilayered barrier structures of Examples 56–60 (line A) with hypothetical linear values for Examples 56–60 (line B)
Figure 16:
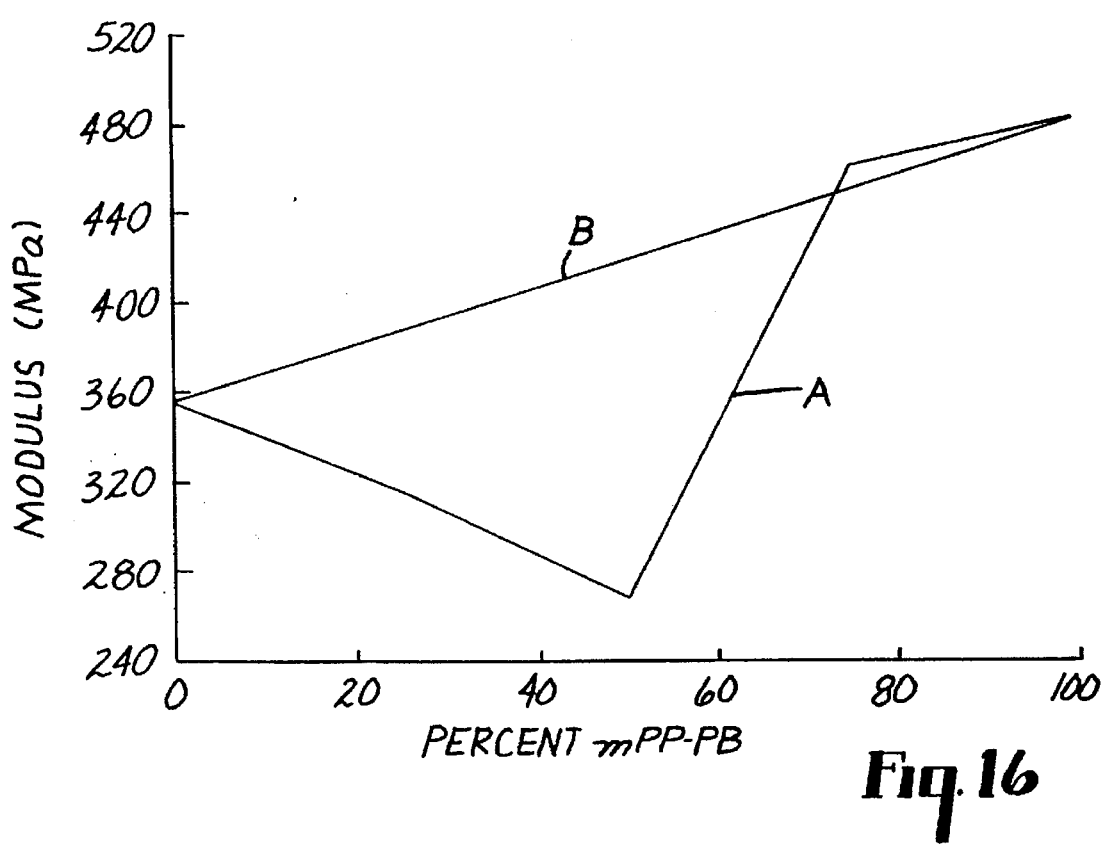
FIG. 16 is a graph comparing Young's modulus of the multilayered barrier structures of Examples 60–64 (line A) with hypothetical linear values for Examples 60–64 (line B)

The effect of the amount of mesomorphous polypropylene (mPP) in the moisture barrier layer (layer A) on the modulus (Young's modulus) for the multilayered barrier films of Examples 56–71 (in comparison to the effect of crystalline polypropylene in Comparison Examples 72–84 is shown in Table 20. In all cases, the modulus for the quenched films of Examples 56–71 is 6.5%–41% lower than for the non-quenched films of Comparison Examples 72–84. A more detailed analysis for the effect of mPP on barrier film modulus for Examples 56–60 is shown in FIG. 15. For mPP concentrations of less than about 70% (or EVA concentrations in the mesopolymer blend of greater than 30%) the multilayered barrier films became less stiff (i.e. softer). As can be seen in FIG. 15, modulus values for the multilayered barrier films with mesopolymer blend concentrations in this range (line A) (i.e., less than 70% mPP) are lower than would be expected from the Rule of Mixtures (line B), as that term is defined herein. Similar effects on modulus are shown in FIG. 16 for the multilayered barrier films of Examples 60–64 with mPP:PB:EVA mesopolymer blend concentrations of less than about 70% of mPP and PB (or EVA concentrations in the mesopolymer blend greater than 30%). As with Examples 56–60, modulus values for the multilayered barrier films with mesopolymer blend concentrations in this range (line A) (i.e., less than 70% mPP:PB) are lower than would be expected from the Rule of Mixtures (line B). Thus, adding EVA to mPP or mPP:PB resins forming the moisture barrier layer of the multilayered barrier films synergistically results in multilayered barrier films which are less stiff than would-be expected for mPP or mPP:PB mesopolymer blends in the concentration range of about 0% to 70%.

Figure 17:
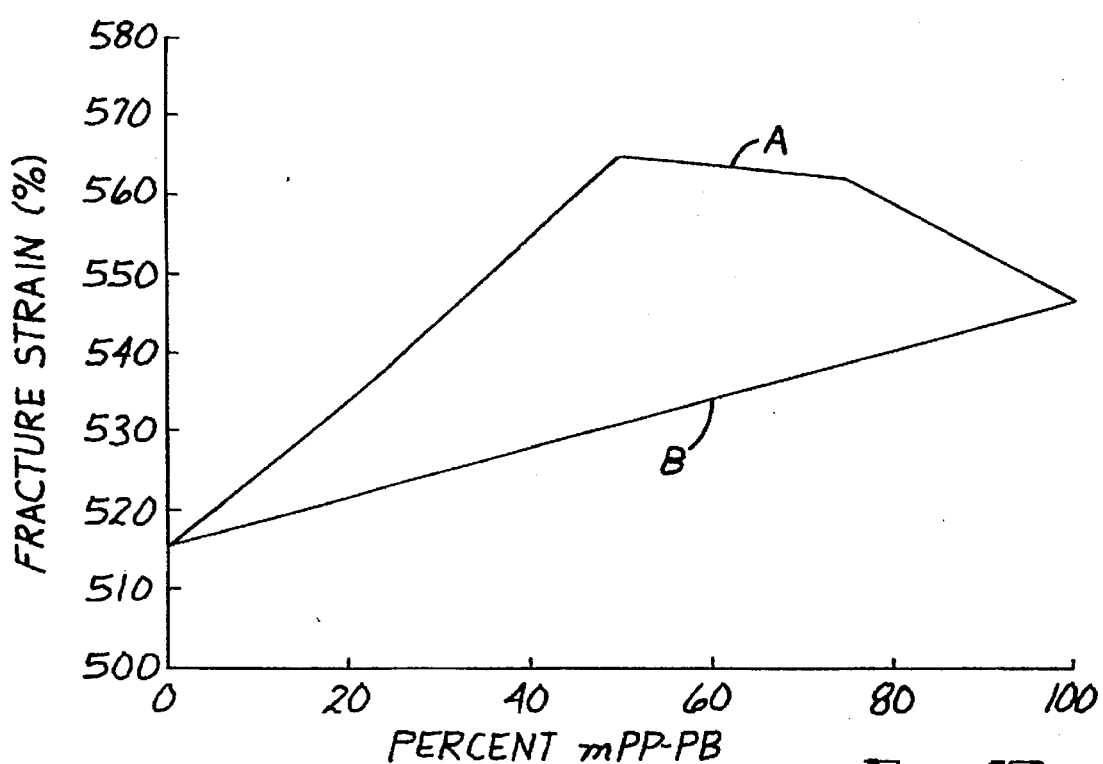
FIG. 17 is a graph comparing the fracture strain of the multilayered barrier structures of Examples 51 and 58–6 (line A) with hypothetical linear values for Example 51 and 58–61 (line B)

Synergy in fracture strain, as shown in FIG. 17, was also observed for Examples 61 and 68–71, where the moisture barrier, layer of the multilayered barrier films comprised a mesopolymer blend of mPP:PB:EAA. That is, fracture strains were greater than would be expected (line A) than under the Rule of Mixtures (line B), as that term is defined herein. Thus, using mPP:PB:EAA mesopolymer blends in the moisture barrier layers of the multilayered barrier films results in films which are surprisingly tougher (i.e. display a greater stain to fracture) than would be expected.

Oxygen transmission rate ($O_2$TR) data was collected for the films of Examples 58, 63, 66 and 70 according to the same procedures and utilizing the same equipment as described for Examples 1–4 and 6 herein. The results were normalized to a 25μ thick film, and reported in cc/m²/day-atmosphere at 25° C. and 0% relative humidity as per Examples 1–4 and 6. The $O^2$TR data for Examples 58, 63, 66 and 70 are reported in Table 21. The results indicate that mesopolymer blends of mesomorphous polypropylene (mPP) and ethylene vinyl acetate (EVA) and ethylene acrylic acid (EAA), either alone or in combination with polybutylene (PB), demonstrate comparable $O_2$TR values to the mPP:PB compositions reported in Table 6 herein.

TABLE 21

Oxygen transmission rates ($O_2$TR), as expressed in cc/m²/d-atm, for Examples 58, 63, 66, and 70.

| Ex. No. | Composition | Ratio (wt %) | $O_2$TR (cc/m²/d-atm) |
|---|---|---|---|
| 58 | mPP:EVA | 50/50 | 3.3 |
| 63 | mPP:PB:EVA | 25/25/50 | 3.4 |
| 66 | mPP:EAA | 50/50 | 3.0 |
| 70 | mPP:PB:EAA | 25/25/50 | 3.0 |

Examples 85–94

Five multilayered tubes and five multilayered pouches were formed from the multilayer barrier films of Examples 3, 58, 63, 66 and 70. To make the tubes, the films were curved into a cylinder and heat sealed on one edge using a heat sealer (Sentinel™, Inc.). The pouches were made by either folding the Example film over on itself, and then heat sealing two-sides, or by using two films, placing one on top of the other, and then heat sealing three of the sides. The tube and pouch dimensions, along with compositions of the moisture barrier layers of the films, are shown in Table 22 for the tubes of Examples 85-89, and in Table 23 for the pouches of Examples 90-94.

TABLE 22

Overall tube dimensions and composition of the moisture barrier layers of the multilayered tubings of Examples 85-89.

| Example Number | Original Example Number | Moisture Barrier Layer Composition | Tube Radius (cm) | Tube Wall Thickness (microns) |
|---|---|---|---|---|
| 85 | 3 | PP:PB (50/50) | 1.9 | 102 |
| 86 | 58 | PP:EVA (50/50) | 1.3 | 74 |
| 87 | 63 | PP:PB:EVA (25/25/50) | 1.1 | 64 |
| 88 | 66 | PP:EAA (50/50) | 1.4 | 89 |
| 89 | 70 | PP:PBP:EAA (25/25/50) | 1.3 | 76 |

TABLE 23

Overall pouch dimensions and composition of the moisture barrier layers of the multilayered pouches of Examples 90-94.

| Example Number | Original Example Number | Moisture Barrier Layer Composition | Pouch Length (cm) | Pouch Width (cm) | Pouch Thickness (microns) |
|---|---|---|---|---|---|
| 90 | 3 | PP:PB (50/50) | 8 | 14 | 102 |
| 91 | 58 | PP:EVA (50/50) | 7 | 12 | 74 |
| 92 | 63 | PP:PB:EVA (25/25/50) | 6 | 11 | 64 |
| 93 | 66 | PP:EAA (50/50) | 8 | 11 | 89 |
| 94 | 70 | PP:PB:EAA (25/25/50) | 7 | 11 | 76 |

EXAMPLES 95-102, AND COMPARISON EXAMPLES 103-110

To determine noise generated by a film during wrinkling, an apparatus capable of flexing a film sample in a cyclic and repeatable manner was constructed in accordance with the teaching of U.S. Pat. No. 4,376,799, the disclosure of which is herein incorporated by reference. Samples of Example films were cut to 8.8 cm by 8.8 cm in size. One end of the film was wrapped around a stationary cylinder of 2.5 cm diameter and the other end to a second, rotatable cylinder displaced 5 cm parallel from the stationary cylinder. Thus, the film formed a cylinder which connected the stationary cylinder to the rotatable cylinder. Noise was generated by the film when the motor was engaged and the rotatable cylinder and attached film were rotated 15° in a forward direction and then 15° in the reverse direction at a frequency of 1.2 cycles per second. A microphone inserted in the stationary cylinder was used to pick up noise and generate an electrical signal which was used for further analysis. The signal from the microphone Was processed through a preamplifier which measured sound level in decibels over a range of 0 to 20 kHz. The signal was then routed to a frequency analyzer which measured the intensity of generated sound in volts as a function of its frequency. These values were then recorded and used for noise data analysis. Background noise, that is, noise in the room as well as noise generated by the operating apparatus without an attached film, was subtracted from the film noise spectrum to produce a spectrum characteristic of the film only. All tests were performed in an anechoic chamber.

Noise can be measured both in terms of its frequency and intensity. In general, sounds of high intensity and frequency seem louder to the human ear than sounds of lower intensity and frequency. Thus, a "quite" film should exhibit a low frequency, low intensity noise spectrum.

Noise spectra for quenched and non-quenched multilayer barrier films of Examples 95-102 and Comparison Examples 103-110 were generated. Noise data for both quenched films and the corresponding non-quenched films are shown in FIGS. 21-36. Table 24 correlates the FIG. number with the Example and Comparison Example number, casting roll temperature and film composition. In all cases, the quenched multilayer barrier films are quieter than the non-quenched films of the same, but non-quenched, composition.

TABLE 24

Film constructions and correlation to FIG. No. for films of Examples 95-102 and Comparison Examples 103-110 (EN = Example Number; CEN = Comparison Example Number; ON = Original Example Number; OCN = Original Comparison Example Number).

| EN/CEN | ON/OCN | FIG. No. | Casting Roll Temp. (°C.) | Moisture Layer Comp. | Component Weight Ratio |
|---|---|---|---|---|---|
| 95/103 | 1/7 | 21/22 | 10/66 | PP:PB | 100:0 |
| 96/104 | 2/8 | 23/24 | 10/66 | PP:PB | 80:20 |
| 97/105 | 6/9 | 25/26 | 10/66 | PP:PB | 50:50 |
| 98/106 | 57/73 | 27/28 | 10/66 | PP:EVA | 75:25 |
| 99/107 | 63/78 | 29/30 | 10/66 | PP:PB:EVA | 25:25:50 |
| 100/108 | 64/79 | 31/32 | 10/66 | PP:PB:EVA | 12.5:12.5:75 |
| 101/109 | 66/81 | 33/34 | 10/66 | PP:EAA | 50:50 |
| 102/110 | 69/84 | 35/36 | 10/66 | PP:PB:EAA | 37.5:37.5:25 |

Comparative Examples 111-112 and Examples 113-114

Samples of the multilayered barrier film of Example 3 were coated with acrylic acid (AA) monomer (Example 113) or dimethylacrylamide (DMA) monomer (Example 114). These coated films were then irradiated using an electron beam at a dosage of 50 kGy (5 Mrads) in an inert nitrogen atmosphere, resulting in the grafting of these monomers to the surfaces of the coated films. In addition, two control films were produced. The first control film comprised an uncoated and non-radiated sample of the Example 3 film (Comparative Example 111). The second control film comprised an uncoated film irradiated at a dosage of 50 kGy (Comparative Example 112) according to the same procedure as for Examples 113 and 114.

To assess the strength of the grafted layer, 180° peel adhesion measurements were performed according to the following procedure. A 2.5 cm wide, 20.3 cm long strip of pressure-sensitive adhesive tape (Scotch™ brand tape no.

8411; 3M Company) was adhered to a 10.1 cm wide, 15.2 cm long sheet of each of the Example and Comparative Example films, with a free end of the tape extending beyond the end of each film. The sample films were then rolled twice with a 1.35 kg hard rubber roller to ensure contact between the adhesive and the sample films. The samples were then aged at room temperature (22° C.) for 24 hours, after which the free end of the tape was removed from the samples at a rate of 15.2 cm/min using a slip/peel testing machine (Instrumentors, Inc., Strongsville, Ohio). The graft monomers employed, electron beam radiation dosage employed, and the peak peel adhesion force measured in grams/2.5 cm for the sample films of Comparative Examples 111 and 112, and Examples 113 and 114 are shown in Table 25.

TABLE 25

Graft monomers used, electron beam radiation dosage employed, and peak peel adhesion measured in grams/2.5 cm for the sample films of Comparative Examples 111 and 112, and Examples 113 and 114.

| Ex. No. | Graft Monomer | E-beam Dose (kGy) | Peak Peel Force (g/2.5 cm) |
| --- | --- | --- | --- |
| Comp. Ex. 111 | none | 0 | 5.9 |
| Comp. Ex. 112 | none | 50 | 7.8 |
| Ex. 113 | AA | 50 | 12.1 |
| Ex. 114 | DMA | 50 | 14.5 |

The data of Table 25 show that barrier films of the present invention with an additional monomer layer grafted thereto have higher peel strength than the same films lacking in the additional monomer layer, and when not exposed to electron beam radiation in an inert atmosphere. Thus, adhesion promoting layers, as well as other layers, can be added to the barrier films of the present invention utilizing the above techniques.

While in accordance with the patent statutes, description of the preferred weight fractions, processing conditions, and product usages have been provided, the scope of the invention is not to be limited thereto or thereby. Various modifications and alterations of the present invention will be apparent to those skilled in the art without departing from the scope and spirit of the present invention. The examples described in this application are illustrative of the possibilities of varying the amounts and types of polymeric materials in the multilayered barrier structures to achieve properties for specific purposes.

Consequently, for an understanding of the scope of the present invention, reference is made to the following claims.

What is claimed is:

1. A method for forming a multilayered structure comprising:
   (a) coextruding a propylene-based material along with a non-chlorine containing organic polymer which is substantially impermeable to oxygen gas to form a multilayered extrudate;
   (b) quenching the multilayered extrudate immediately after extruding to provide a multilayered structure with a core layer of the non-chlorine containing organic polymer and at least one layer of a mesophase propylene-based material proximate the core layer; and
   (c) grafting a graft layer to at least a portion of the multilayered structure through exposure to a dosage of ionizing radiation.

2. A method for forming a multilayered structure according to claim 1, wherein the graft layer enhances one or more properties of the multilayered structure, including surface adhesion, coefficient of friction, oxygen permeability, moisture permeability, or combinations thereof.

3. A method for forming a multilayered structure according to claim 1, wherein the dosage of ionizing radiation comprises a dosage of electron beam radiation at from about 5 kGy to about 200 kGy.

4. A method for forming a multilayered structure according to claim 1, wherein the coextruding step further comprises coextruding a functionalized olefin polymer along with the propylene-based material and the non-chlorine containing organic polymer to form the multilayered extrudate, the functionalized olefin polymer upon being quenched, forming one or more adhesive layers disposed between the core layer and the mesophase propylene-based material layer.

5. A method for forming a multilayered structure according to claim 1, further comprising, after the quenching step, fabricating the multilayered structure into a container, an ostomy pouch, a transdermal drug-delivery patch, a tape, a film, a tube, or a packaging material.

6. A method for forming a multilayered structure according to claim 1, wherein the non-chlorine containing organic polymer is selected from the group consisting of a vinyl-alcohol-containing polymer, polyacrylonitrile, polystyrene, polyester, nylon, and combinations thereof.

7. A method for forming a multilayered structure according to claim 1, wherein the non-chlorine containing organic polymer exhibits a permeability to oxygen gas of less than about 100 cc/m$^2$/d-atm at 25° C. and 0% relative humidity.

8. A method for forming a multilayered structure according to claim 1, wherein the mesophase propylene-based material is selected from the group consisting of mesomorphous polypropylene, a mesopolymer blend, a mesocopolymer, and combinations thereof.

9. A method for forming a multilayered structure according to claim 1, wherein the graft layer comprises a surface adhesion layer formed by affixing to the multilayered structure a compound selected from the group consisting of acrylic acid, dimethylacrylamide, N-vinyl-2-pyrrolidone, a copolymer of N-vinyl-2-pyrrolidone and trimethylolpropanetriacrylate, glycidyl acrylate, hydroxyethyl acrylate, hydroxymethyl acrylate, 2-vinyl pyridine, sulfoethyl methacrylate, diisopropylacrylamide, N,N-diethylamino acrylate, and combinations thereof.

10. A method for forming a multilayered structure according to claim 1, wherein the multilayered structure further comprises one or more adhesive layers disposed between said propylene-based material and said non-chlorine containing organic polymer comprising a functionalized olefin polymer selected from the group consisting of an anhydride of a polyolefin, an acid of a polyolefin, an acid/anhydride of a polyolefin, and combinations thereof.

11. A method for forming a multilayered structure according to claim 1, wherein the multilayered structure further comprises one or more adhesive layers of a functionalized mesocopolymer disposed between said propylene-based material and said non-chlorine containing organic polymer.

12. A method for forming a multilayered structure according to claim 1, wherein said multilayered structure resists degradation after exposure to ionizing radiation dosages up to 200 kGy.

13. A method for forming a multilayered structure according to claim 12, wherein the radiation resistant article comprises a film, a fiber, a micro fiber, a tube, an ostomy pouch, a tape, a transdermal drug delivery patch, or a packaging material.

14. A method for forming a multilayered structure according to claim 1, wherein said multilayered structure further comprises a tempering additive selected from the group consisting of ethylene copolymers, polybutylene, and polybutylene copolymers.

15. A method for forming a multilayered structure according to claim 1, further comprising laminating said multilayered structure to a fabric backing.

16. A method for forming a multilayered structure according to claim 1, further comprising the step of orienting said structure at a temperature less than 60° C.

17. A method for forming a multilayered structure according to claim 1, wherein said multilayered structure is in the form of a multilayered film having a thickness between about 6 and 625 μm and said quenching step comprises naming said coextruded structure over a quench roll or drum until solidified, wherein said quench roll or drum is positioned within about 5 cm from the die used to coextrude said structure and is maintained at a temperature of less than about 38° C.

18. A method for forming a multilayered structure according to claim 1, wherein said multilayered structure is in the form of a multilayered film having a thickness between about 6 and 625 μm and said quenching step comprises plunging said coextruded structure into a quench bath, wherein said quench bath is positioned within about 13 cm from the die used to coextrude said structure and is maintained at a temperature of less than about 4° C.

19. A method for forming a multilayered structure comprising:

coextruding a propylene-based material along with a non-chlorine containing organic polymer which is substantially impermeable to oxygen gas to form a multilayered extrudate;

quenching the multilayered extrudate immediately after extruding to provide a multilayered structure with a core layer of the non-chlorine containing organic polymer and at least one layer of a mesophase propylene-based material proximate the core layer;

grafting a graft layer to at least a portion of the multilayered structure through exposure to a dosage of ionizing radiation; and fabricating the multilayered structure into a container, an ostomy pouch, a transdermal drug-delivery patch, a tape, a film, a tube, or a packaging material, wherein said multilayered structure exhibits a permeability to oxygen gas of less than about 100 $cc/m^2/d$-atm at 25° C. and 0% relative humidity and resists degradation after exposure to ionizing radiation dosages up to 200 kGy.

20. A method for forming a multilayered structure comprising:

coextruding a propylene-based material, an adhesive, and a non-chlorine containing organic polymer which is substantially impermeable to oxygen gas to form a multilayered extrudate, wherein said adhesive is disposed between said propylene-based material and said non-chlorine containing organic polymer and comprises a functionalized olefin polymer;

quenching the multilayered extrudate immediately after extruding to provide a multilayered structure with at least one layer of a mesophase propylene-based material, wherein the mesophase propylene-based material is selected from the group consisting of mesomorphous polypropylene, a mesopolymer blend, a mesocopolymer, and combinations thereof;

grafting a graft layer to at least a portion of the multilayered structure through exposure to a dosage of ionizing radiation; and fabricating the multilayered structure into a container, an ostomy pouch, a transdermal drug-delivery patch, a tape, a film, a tube, or a packaging material, wherein the graft layer comprises a surface adhesion layer formed by affixing to the multilayered structure a compound selected from the group consisting of acrylic acid, dimethylacrylamide, N-vinyl-2-pyrrolidone, a copolymer of N-vinyl-2-pyrrolidone and trimethylolpropanetriacrylate, glycidyl acrylate, hydroxyethyl acrylate, hydroxymethyl acrylate, 2-vinyl pyrridine, sulfoethyl methacrylate, diisopropylacrylamide, N,N-diethylamino acrylate, and combinations thereof.

* * * * *

UNITED STATES PATENT AND TRADEMARK OFFICE
CERTIFICATE OF CORRECTION

PATENT NO.: 5,643,375

DATED: July 1, 1997

INVENTOR(S): Debra L. Wilfong and Richard J. Rolando

It is certified that error appears in the above-identified patent and that said Letters Patent is hereby corrected as shown below:

Col. 8, line 44, "6" should read -- 61 --.

Col. 21, line 8, "114 4" should read -- 1-4 --.

Col. 41, line 16, "naming" should read -- running --.

Signed and Sealed this

Eighth Day of December, 1998

Attest:

BRUCE LEHMAN

Attesting Officer  Commissioner of Patents and Trademarks